(12) United States Patent
Landis et al.

(10) Patent No.: US 8,777,933 B2
(45) Date of Patent: Jul. 15, 2014

(54) RESPIRATORY SECRETION RETENTION DEVICE, SYSTEM AND METHOD

(75) Inventors: Robert M. Landis, Mountainside, NJ (US); Charles A. Lewis, Carrabelle, FL (US); Angelo Caruso, Boca Raton, FL (US); Bruce Sher, Lighthouse Point, FL (US); Louis Javier Collazo, Pompano Beach, FL (US); Sanjay Chandran, Boca Raton, FL (US); Norman Hansen, Highland Beach, FL (US)

(73) Assignee: Mergenet Medical, Inc., Coconut Creek, FL (US)

( * ) Notice: Subject to any disclaimer, the term of this patent is extended or adjusted under 35 U.S.C. 154(b) by 916 days.

(21) Appl. No.: 12/648,033

(22) Filed: Dec. 28, 2009

(65) Prior Publication Data

US 2010/0154797 A1 Jun. 24, 2010

Related U.S. Application Data

(63) Continuation-in-part of application No. 12/431,069, filed on Apr. 28, 2009.

(60) Provisional application No. 61/104,597, filed on Oct. 10, 2008.

(51) Int. Cl.
*A61M 1/00* (2006.01)

(52) U.S. Cl.
USPC ....... 604/540; 604/317; 604/403; 128/207.14

(58) Field of Classification Search
USPC ............. 604/317, 319, 540–542; 128/205.12, 128/205.27, 205.29
See application file for complete search history.

*Primary Examiner* — Melanie Hand
(74) *Attorney, Agent, or Firm* — Adam C. Underwood

(57) ABSTRACT

A novel and non-obvious apparatus, system, and method for managing respiratory secretions and fluids in sections of artificial airways. In an embodiment of the invention, a respiratory secretion retention (RSR) device configured to fluidly connect to an artificial airway can be provided. The respiratory secretion retention (RSR) device can include a housing that defines a passageway for the flow of respiratory gases, a chamber defined by the housing with a portion of the chamber configured to retain exhaled respiratory particulate and liquid, a patient side port coupled with the housing, which is in fluid communication with an artificial airway and at least one access port coupled with the housing were the at least one access port includes a control valve. In an aspect of this embodiment, the housing further can include an instillation port.

43 Claims, 32 Drawing Sheets

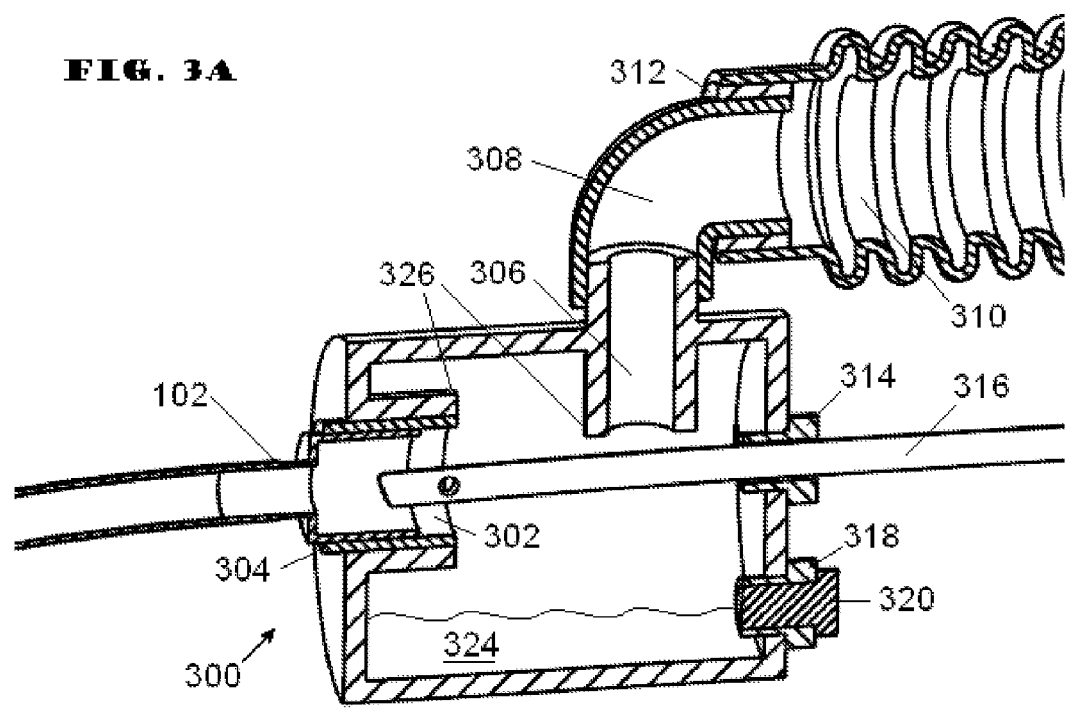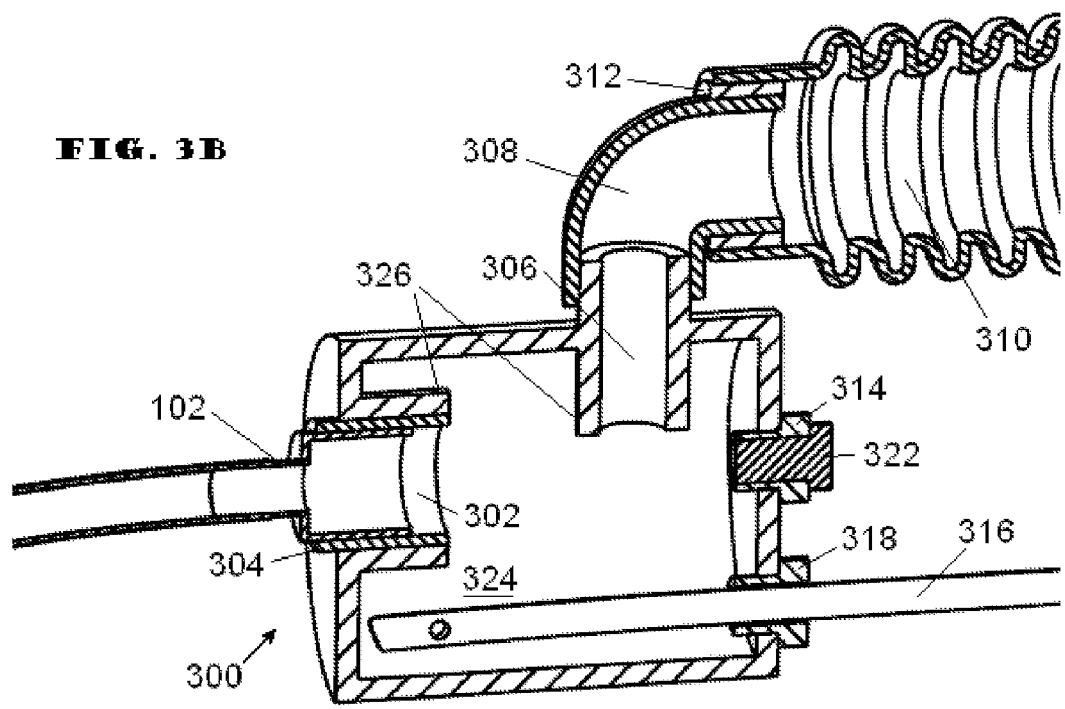

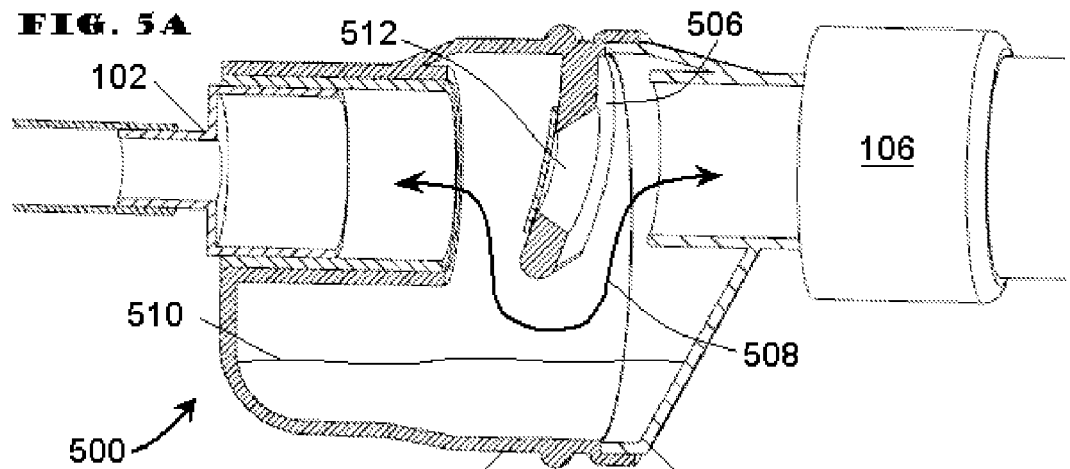
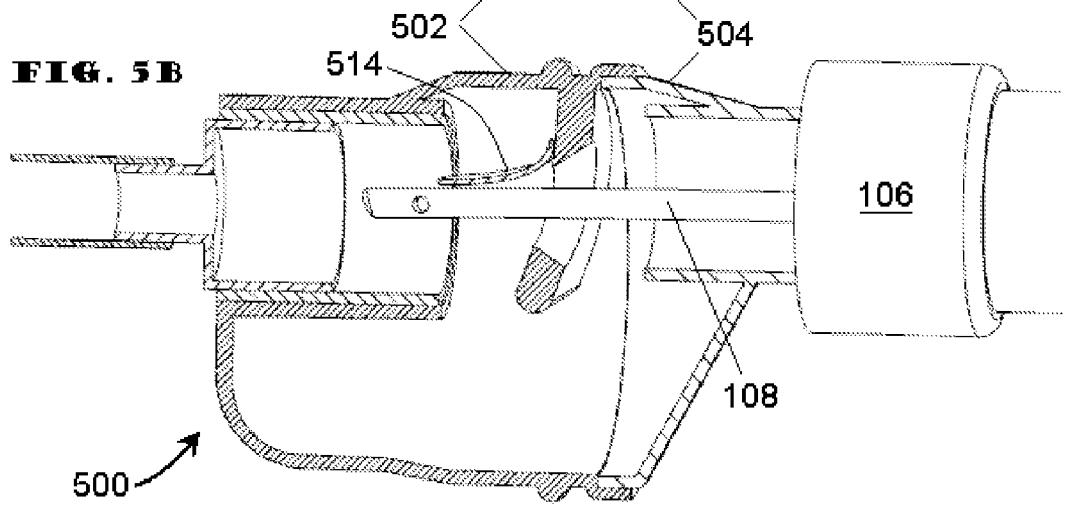
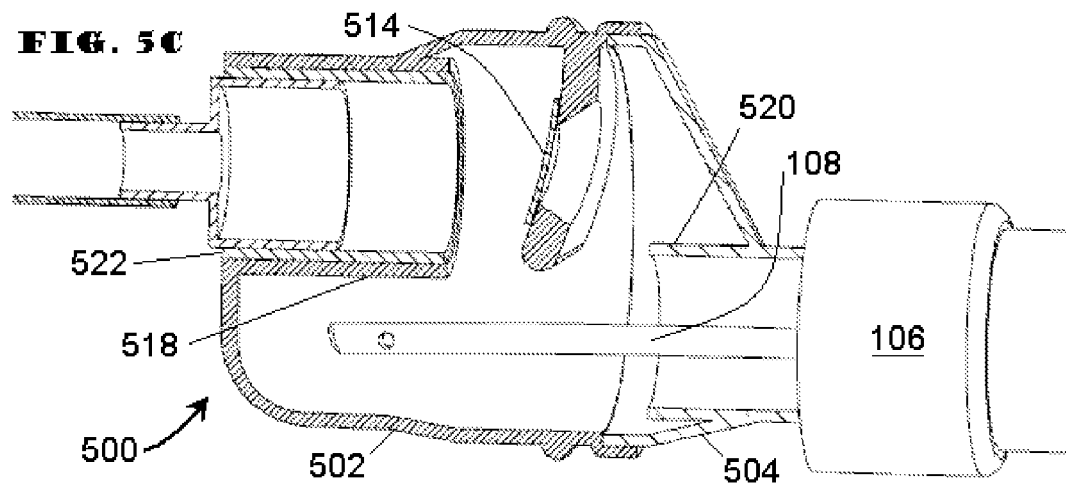

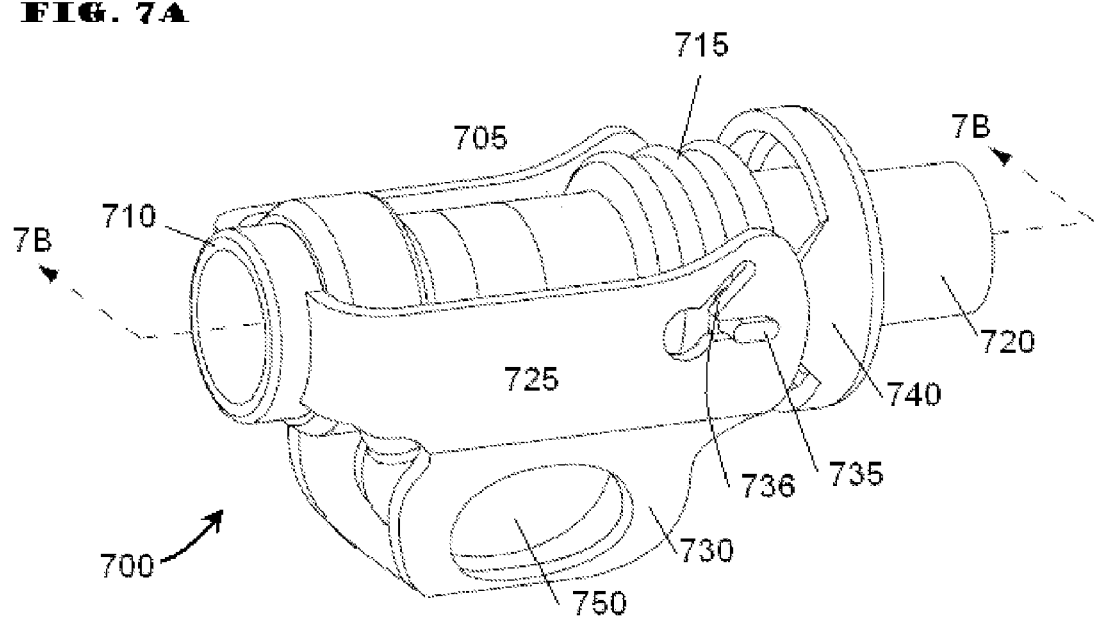
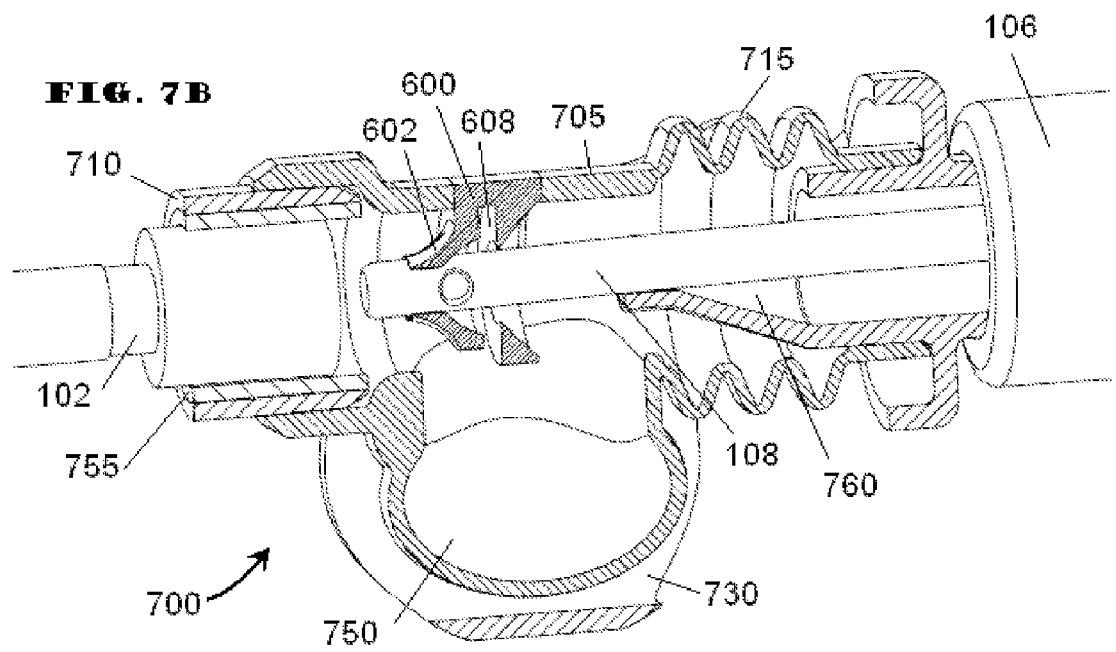

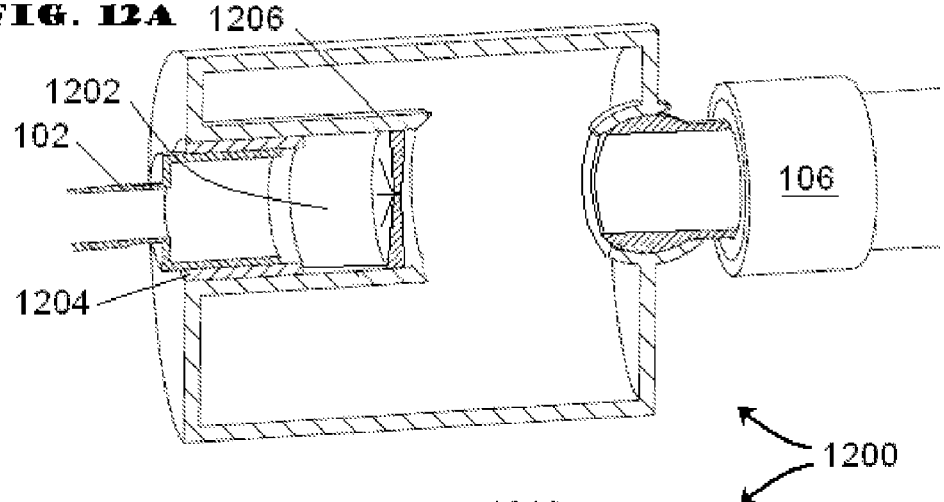
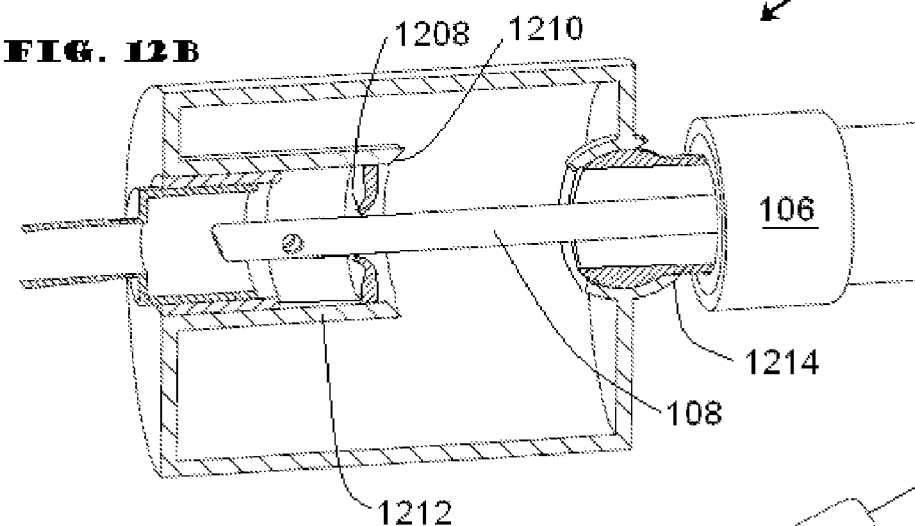
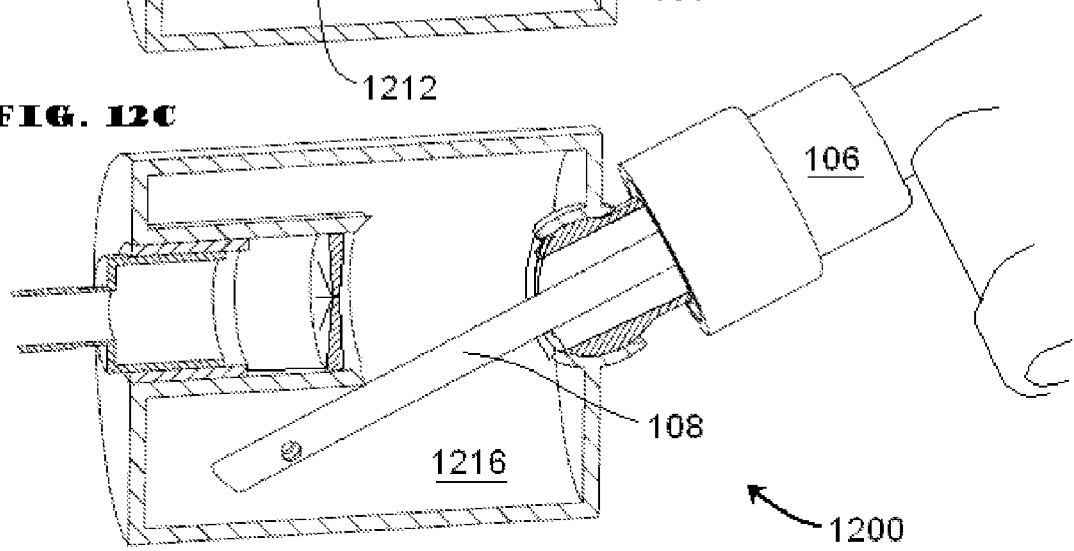

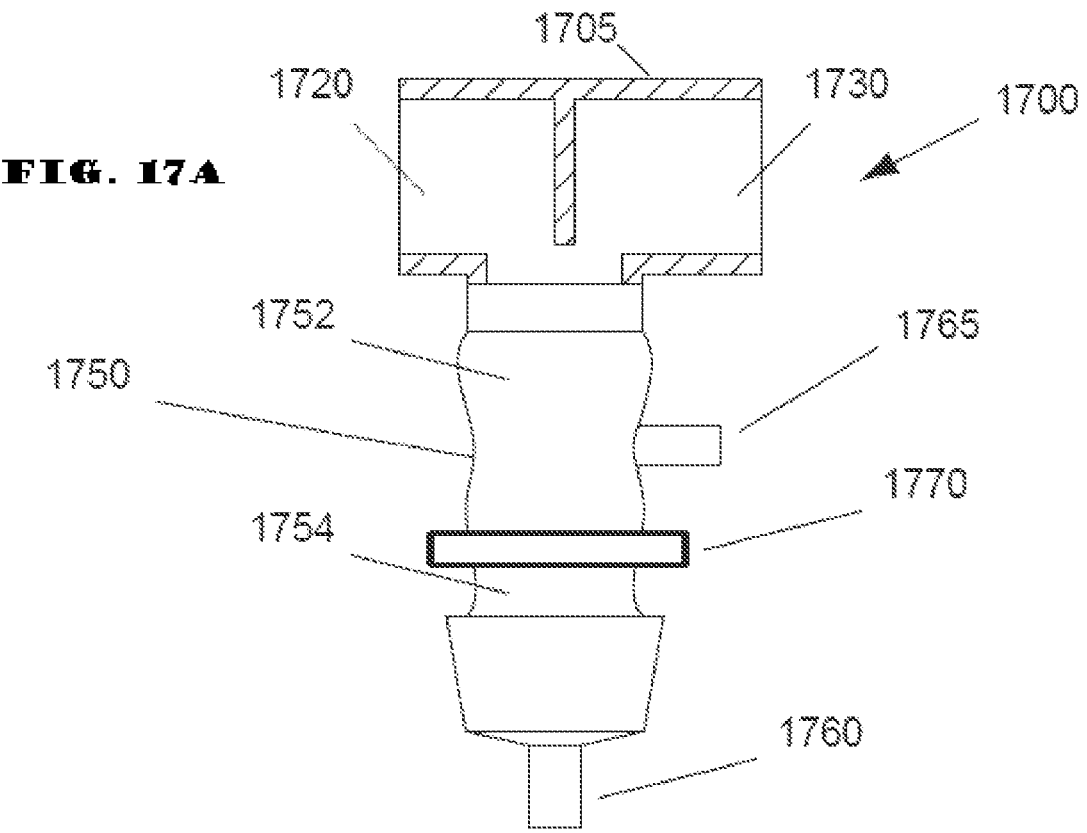
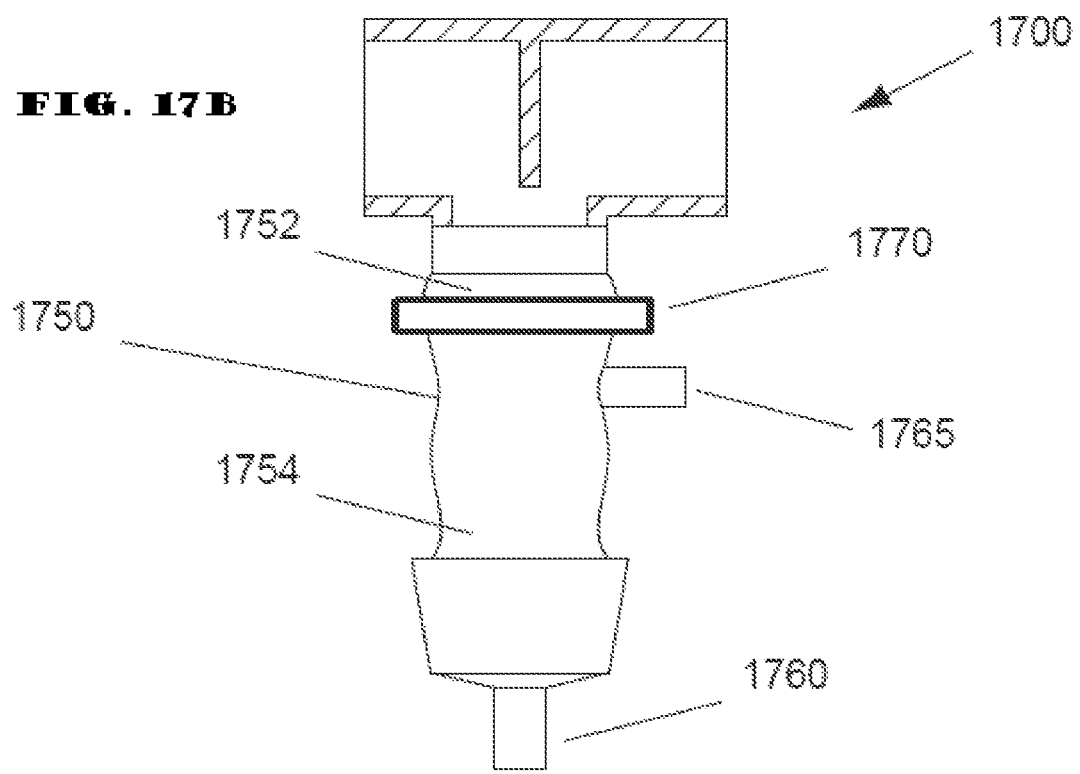

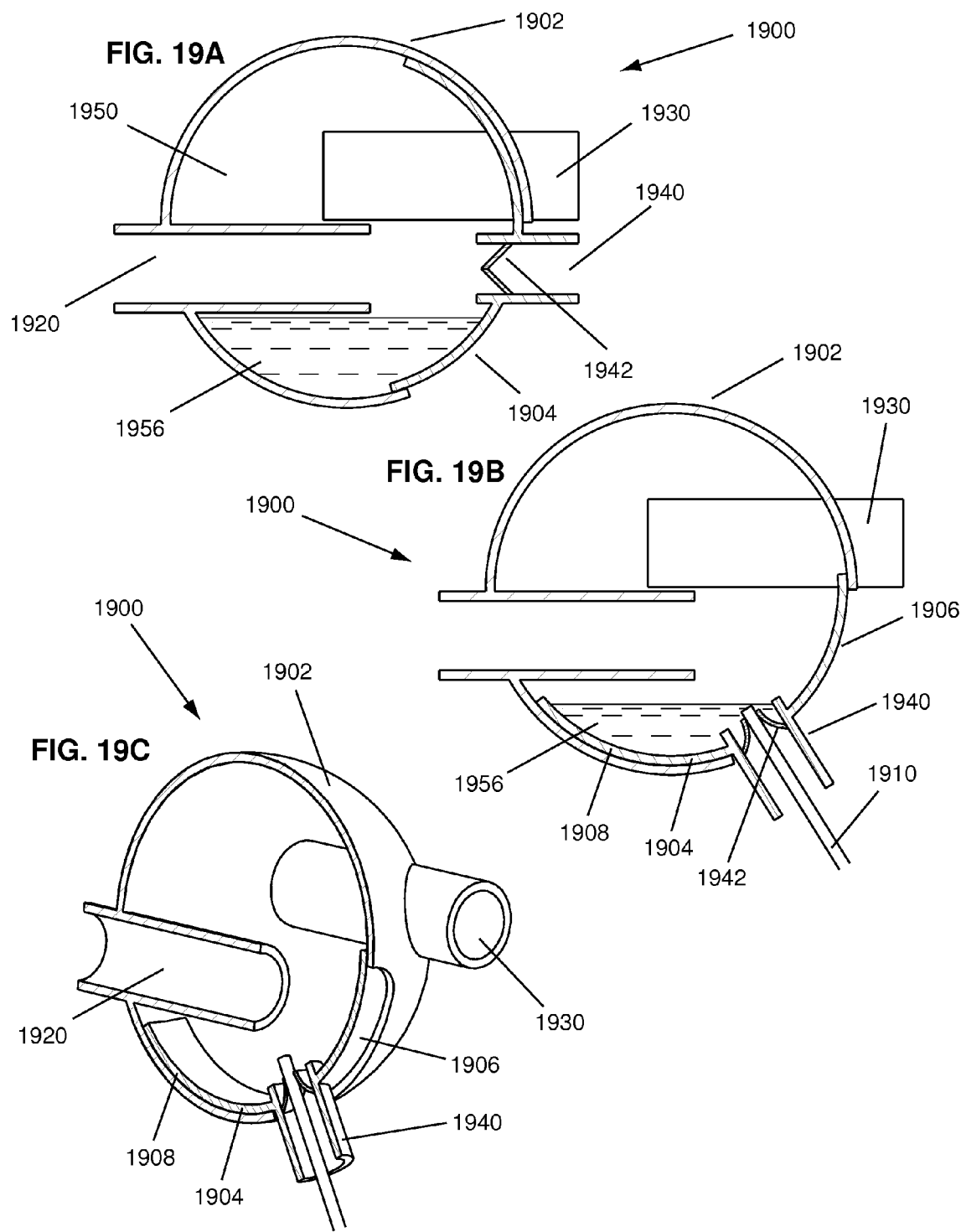

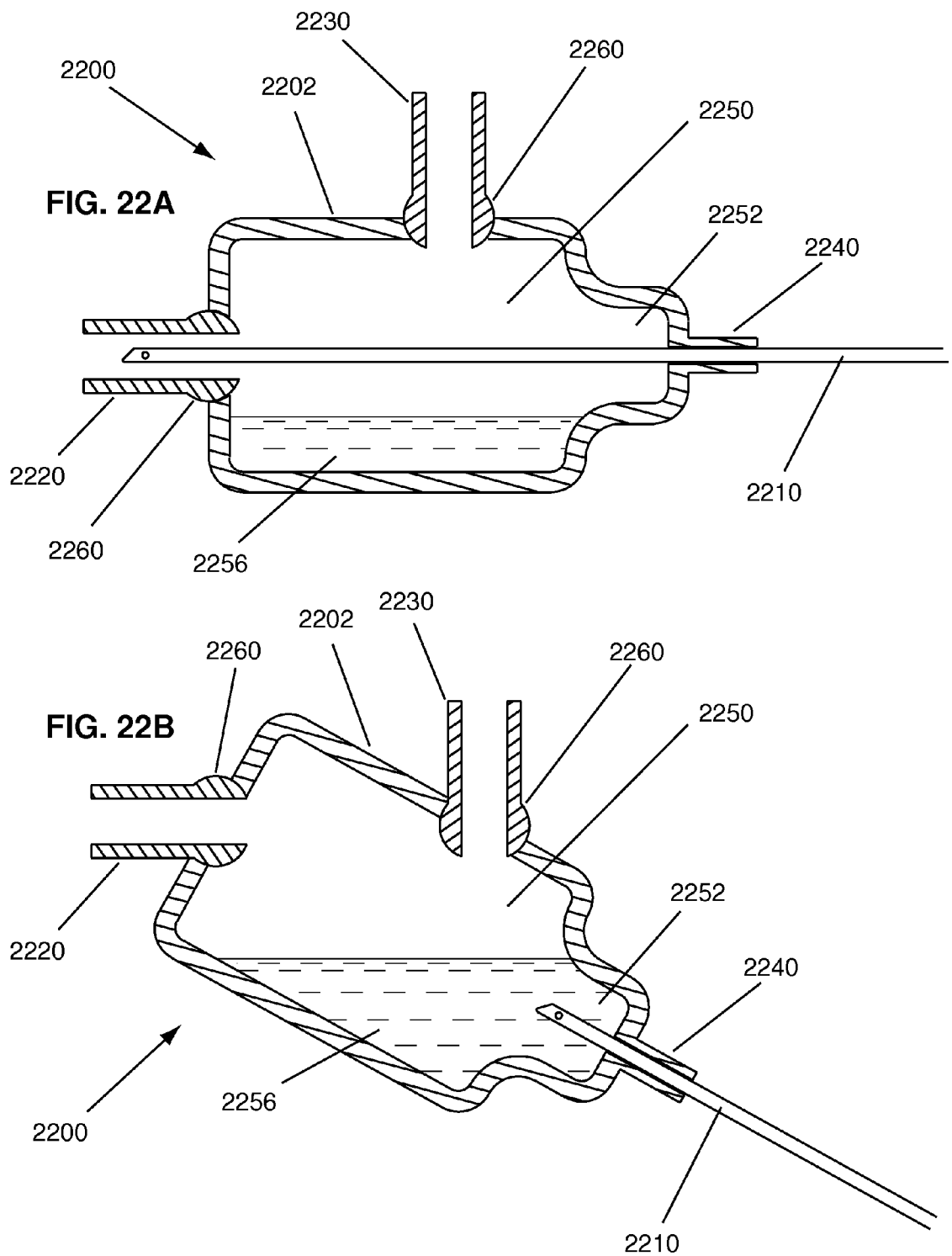

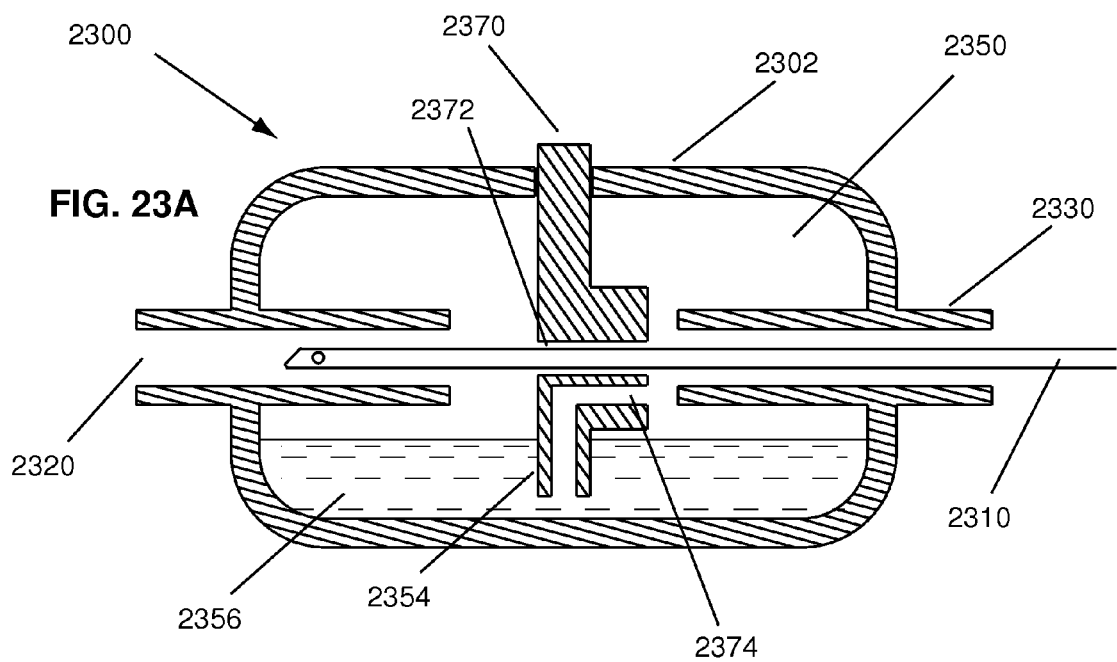
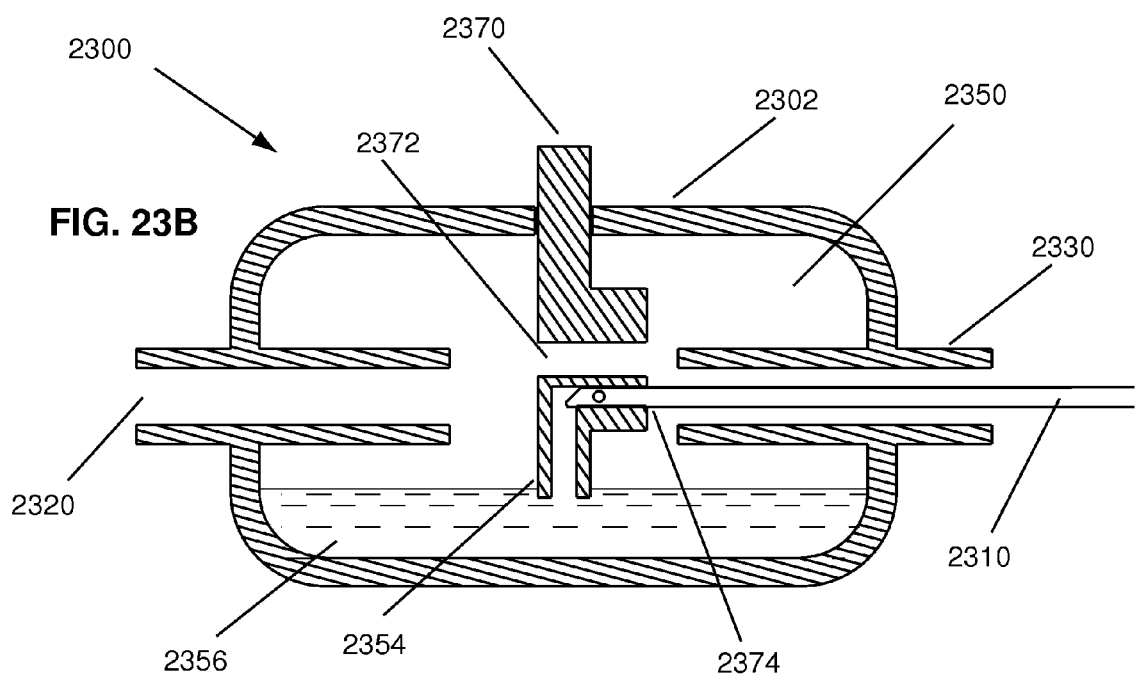

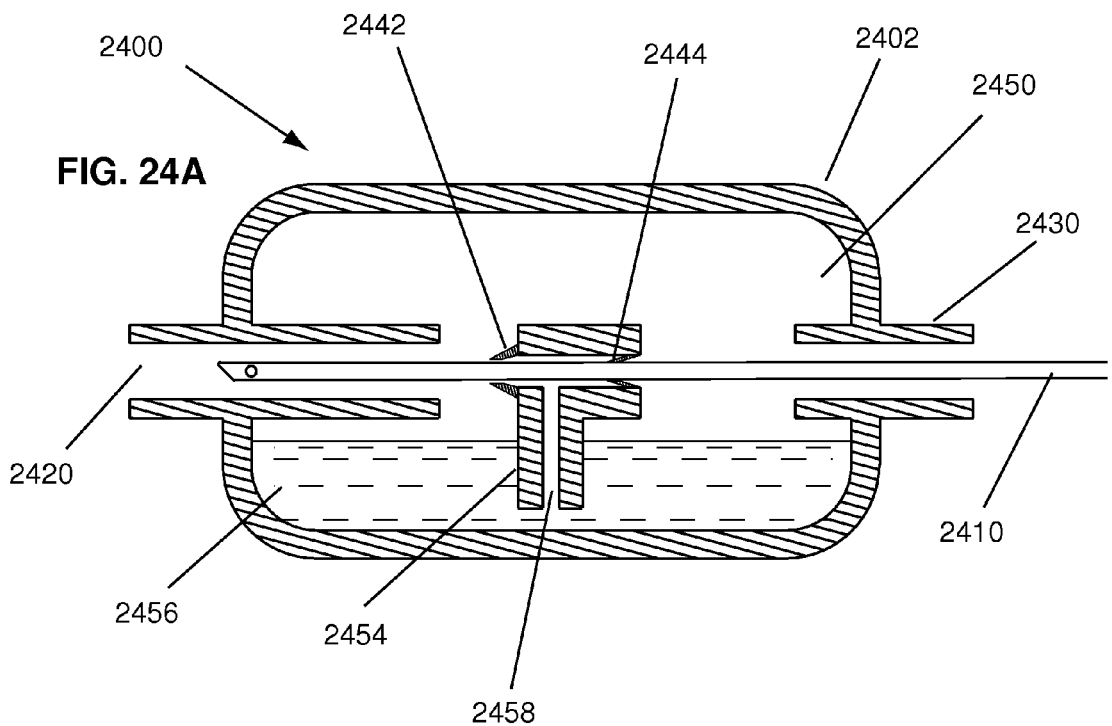
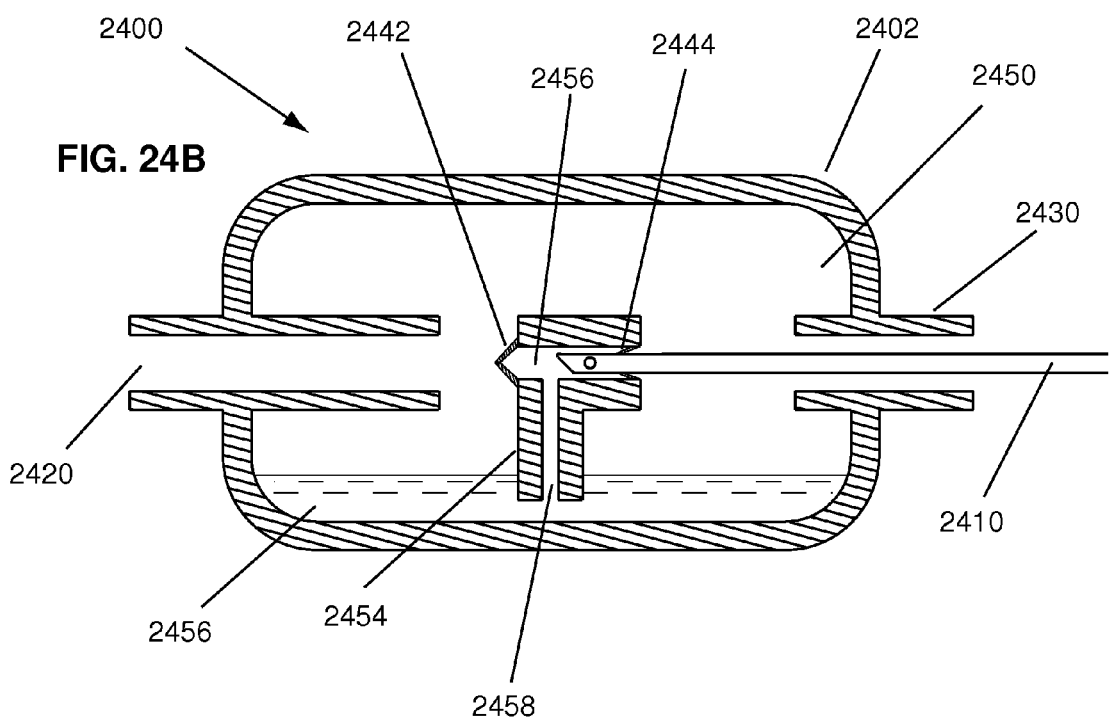

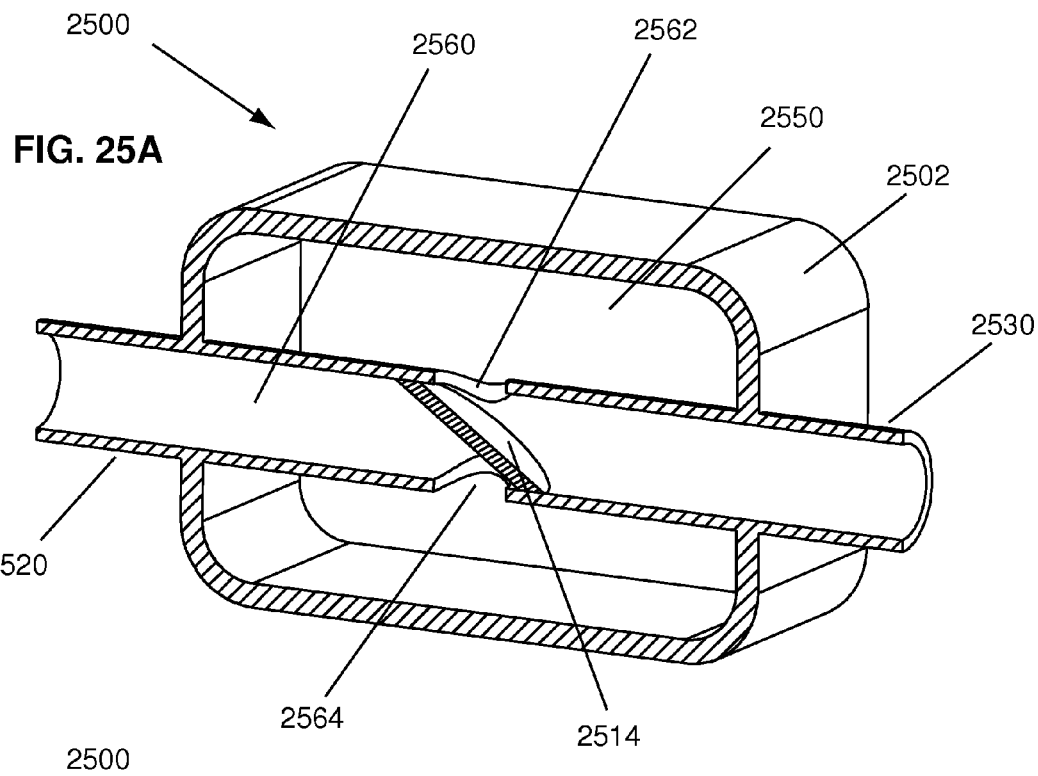
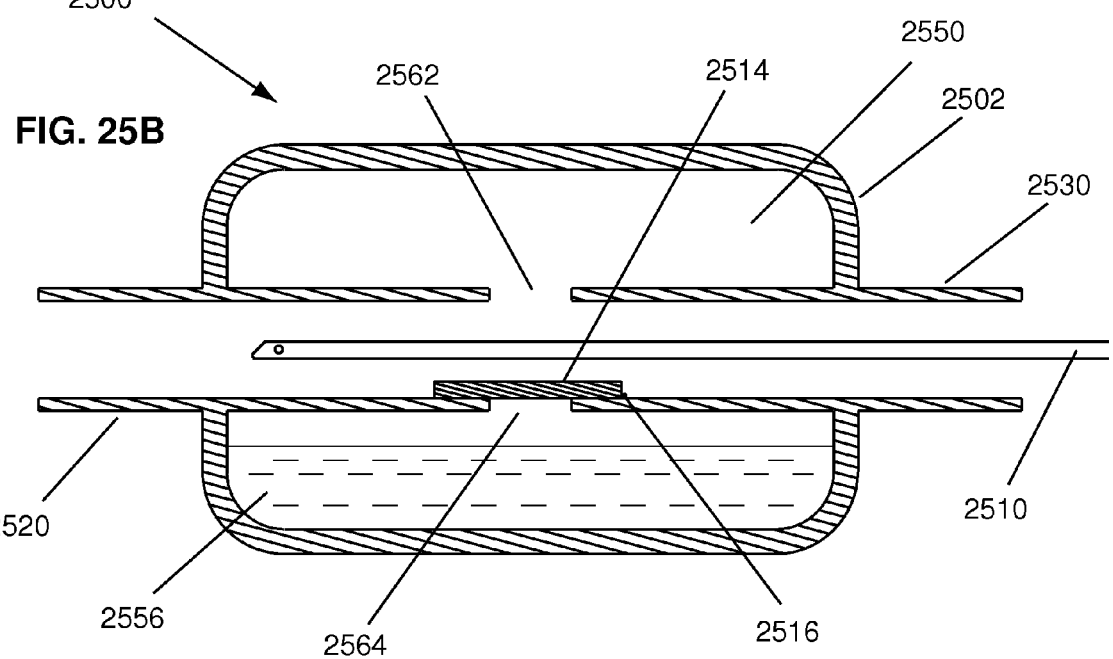

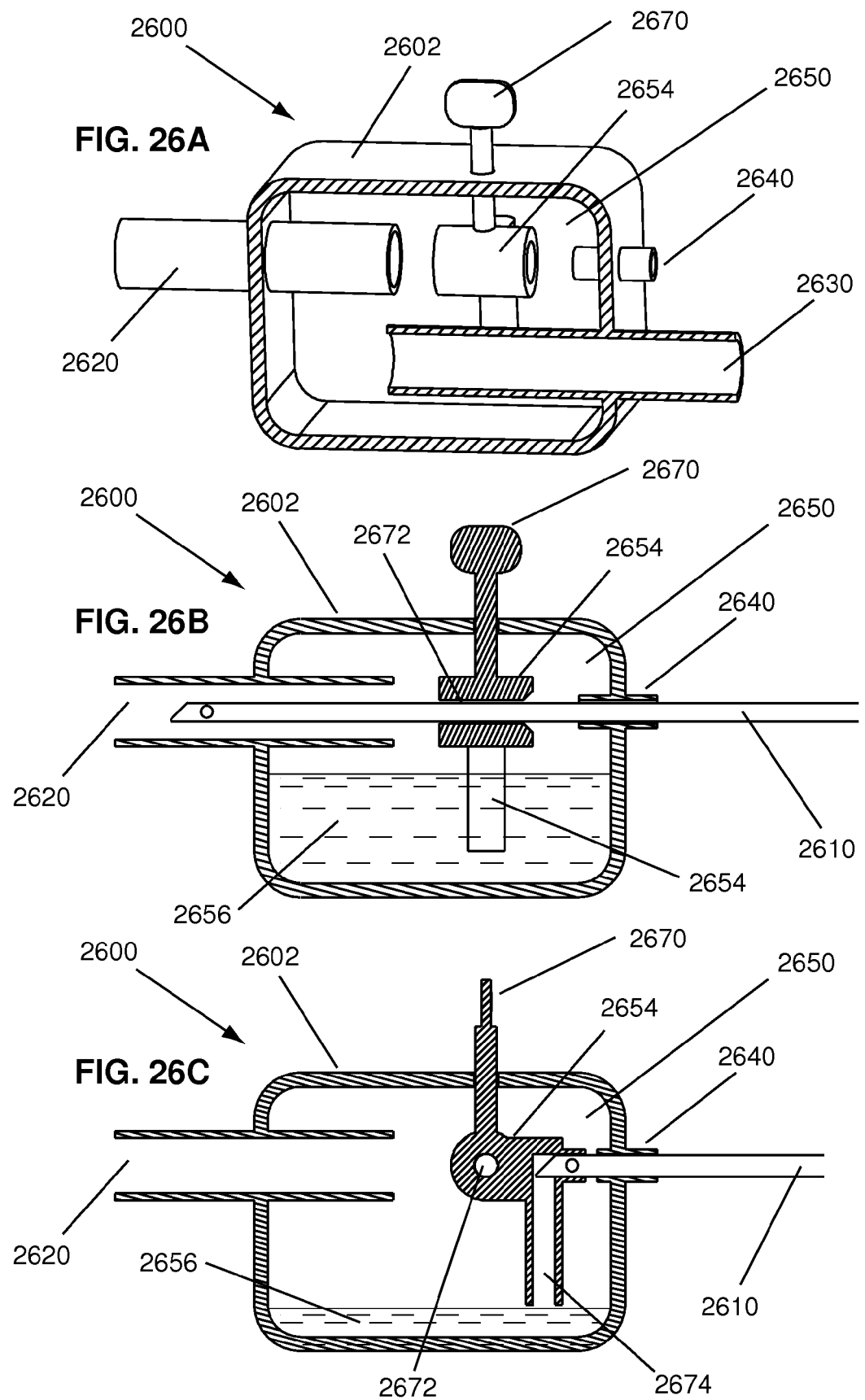

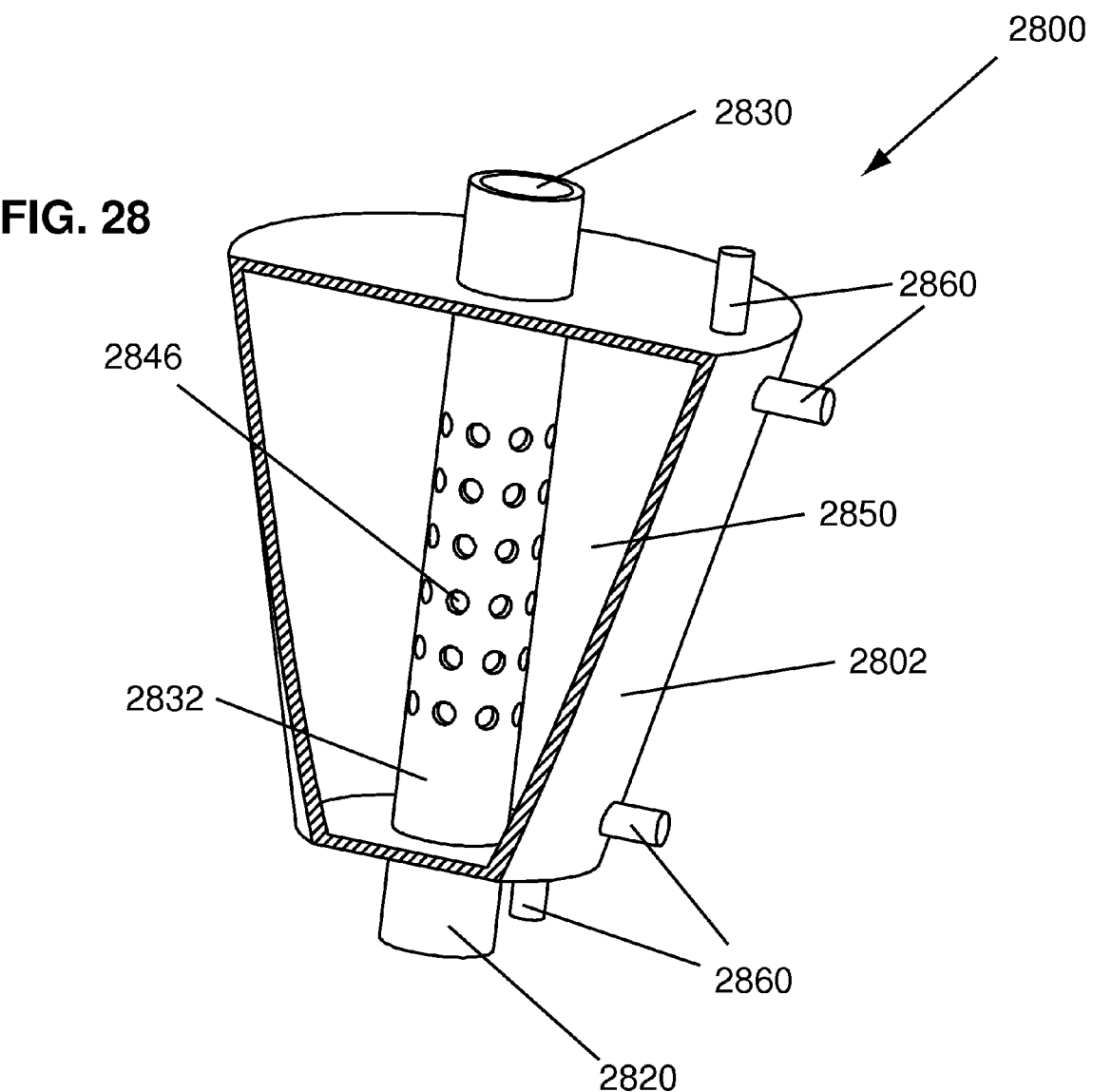

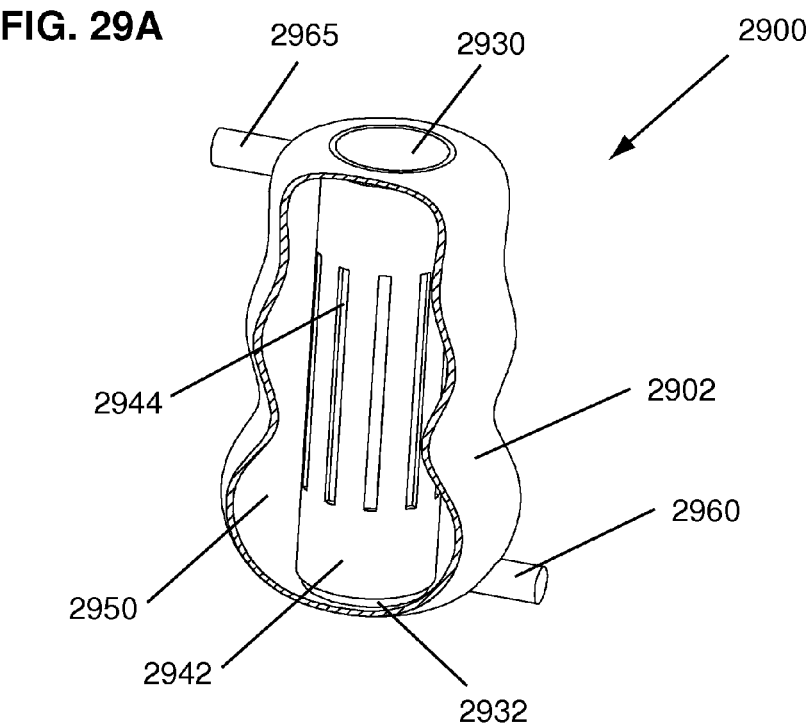
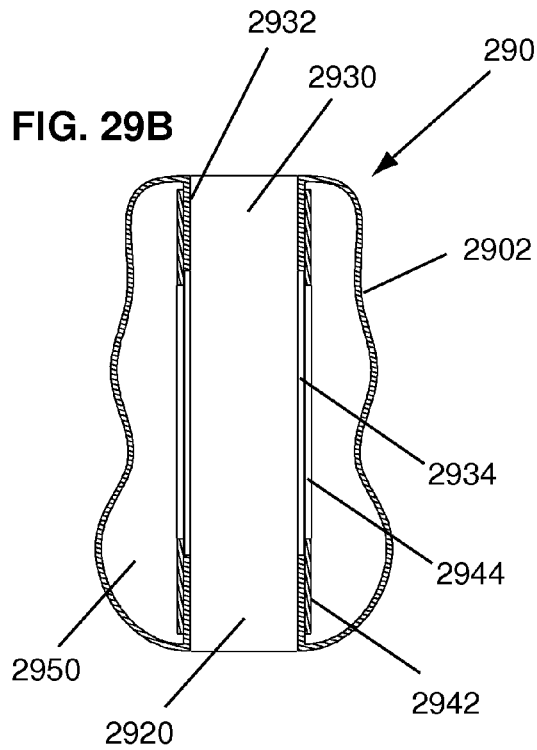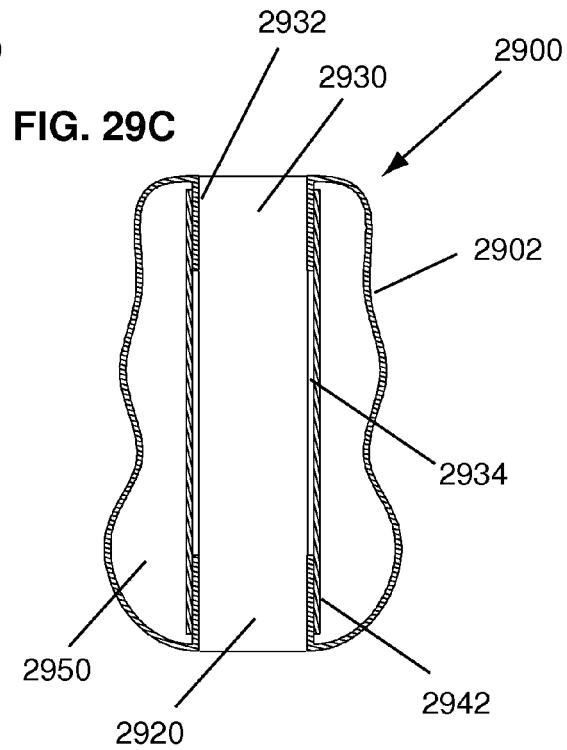

RESPIRATORY SECRETION RETENTION DEVICE, SYSTEM AND METHOD

RELATED APPLICATIONS

This application is a continuation-in-part of pending U.S. application Ser. No. 12/431,069 filed Apr. 28, 2009 to Robert M. Landis, et al., entitled RESPIRATORY SECRETION RETENTION DEVICE, SYSTEM AND METHOD, which application claims benefit and priority from U.S. Provisional Patent Application Ser. No. 61/104,597, filed Oct. 10, 2008, the entire contents of all of which are incorporated herein by reference.

BACKGROUND OF THE INVENTION

1. Statement of the Technical Field

The present invention relates to artificial airways and more particularly to an airway device for controlling respiratory secretions in artificial airways, and associated devices such as respiratory gas delivery devices.

2. Discussion of the Related Art

The use of artificial airways is a common method of maintaining an open airway for patients who require some type of respiratory assistance. Artificial airways come in a variety of options depending on the patient and level of respiratory intervention required. Large numbers of artificial airways have three common features. First, the artificial airway will be a flexible tube that extends into the patient's trachea. Second, most artificial airways will have an inflatable cuff near the distal end of the tube. The inflatable cuff can be used to make an airtight seal, e.g., for nasal tracheal, oral tracheal and tracheostomy tubes where the entire breath of the patient is directed through the tube. Third, the standard artificial airway has a 15 mm fitting on the external opening of the tube to which respiratory gas delivery devices and instruments can be attached compliant with the ISO 5356; Anesthetic and Respiratory Equipment—Conical Connectors standard.

One of the common issues with having the patient breathe through these artificial airways is that respiratory secretions, which would normally enter the pharynx and be swallowed, expectorated or coughed out through the mouth, are forced to egress through the lumen of the artificial airway. The presence of the tube, being a foreign object in the airway can also stimulate respiratory secretions.

Keeping the tube and airway clear of secretions is a procedure performed by clinicians, which requires training and vigilance. Depending on the condition of the patient, the frequency of clearing the airway with a suction catheter varies greatly. When secretions accumulate in the tube there is added resistance to breathing and when the patient is strong enough, a forceful exhalation sends the secretions out through the tube and into the room or into any device attached to the tube.

Some fluid trap devices for use between an artificial airway and respiratory gas delivery devices, such as a ventilator circuit, have a fill volume substantially independent of orientation of the trap within the fluid circuit. Such fluid trap devices are disadvantageous as they impose unnecessary and excessive dead-space (e.g., exhaled air that is re-breathed) to achieve the independent orientation.

Typically, when a ventilator circuit or an instrument is detached from an artificial airway, the patient coughs and respiratory secretions and fluids are sprayed into the room. In addition, it is common for a patient on a ventilator to have secretions accumulate inside an artificial airway, such as endotracheal (ET) tube, with no place to go but up the tube, down the tube or into whatever breathing instrument is attached to the ET tube.

In the last decade, the use of "closed suction" devices with ventilator breathing circuits has become a standard at many medical facilities. A closed suction device allows for access to the airway with a suction catheter without detaching or removing the treatment device from the artificial airway. Closed suction systems add additional support to clinicians by greatly reducing the time and effort necessary for clearing the airway. A closed suction device for example, can allow a catheter to advance into the artificial airway for suctioning and then be withdrawn into a protective sheath where it is protected from contamination when the catheter is not in use. The closed suction catheter may be used multiple times without opening the device to the atmosphere, and is usually used for one to several days. A closed suction system allows access to the ventilator breathing circuit connected with the patient to remain "closed" as opposed to methods that require it to be "opened" to the atmosphere for access. Closed suction also reduces risk of microbial contamination of the artificial airway during suctioning thereby protecting the patient's airway from infection. In numerous medical institutions, the infection control departments have made the use of closed suction a standard of practice by requiring that all intubated patients in the intensive care unit (ICU) have a closed suction system installed.

Most clinicians find that there are a significant number of instances when it is necessary to detach a ventilator circuit or respiratory instrument (i.e. "open the circuit"), and having protection from patient secretions entering the environment during these occasions is most desirable.

There are three main problems with secretions in the tube of an artificial airway. First, when the ventilator circuit is disconnected, secretions can be sprayed into the room if the patient coughs. Second, secretions in the artificial airway result in compromised breathing. Third, when secretions are forced out into the attached ventilator circuit, these secretions can foul the attached instruments, such as a heat and moisture exchange (HME) device, and the like.

SUMMARY OF THE INVENTION

Embodiments of the present invention address deficiencies of the art in respect to artificial airways and respiratory secretions management and provide a novel and non-obvious apparatus, system, and method for managing respiratory secretions and fluids in a section of an artificial airway, ventilator circuit system. In an embodiment of the invention, a respiratory secretion retention (RSR) device configured for fluidly connecting to an artificial airway can be provided. A respiratory secretion retention device configured for fluidly connecting to an artificial airway comprising a housing that defines a passageway for the flow of respiratory gases, a chamber defined by the housing with a portion of the chamber configured to retain exhaled respiratory particulate and liquid, a patient side port coupled with the housing, which is in fluid communication with an artificial airway and at least one access port configured to provide access to the chamber and the patient port. In another aspect of this embodiment, the at least one access port can include a control valve, where the control valve can be located in a downstream position of a passage of the access port to control access from the access port to the chamber.

In another embodiment of the invention, a respiratory secretion retention (RSR) device configured for fluidly connecting to an artificial airway can be provided. The respiratory secretion retention (RSR) device can include a housing that defines a passageway for the flow of respiratory gases, a chamber defined by the housing with a portion of the chamber configured to retain exhaled respiratory particulate and liquid, a patient side port coupled to the housing, which is in fluid communication with an artificial airway, a suction tube subassembly coupled to the housing, which defines a medical instrument passage and a suction tube portion and at least one access port configured to provide access to the chamber and the patient side port. In another aspect of this embodiment the suction tube subassembly is coupled to a actuation mechanism that provides for repositioning of the suction tube subassembly with respect to the housing.

In yet another embodiment of the invention, a respiratory secretion retention (RSR) device configured for fluidly connecting to an artificial airway can be provided. The respiratory secretion retention (RSR) device can include a housing that defines a passageway for the flow of respiratory gases, a chamber defined by the housing with a portion of the chamber configured to retain exhaled respiratory particulate and liquid, a patient port defined by the housing, which is in fluid communication with an artificial airway, at least one access port configured to provide access to the chamber and the patient port and a tube coaxially aligned and coupled to the access port and the patient port, to define a passage between the access port and the patient port. In another aspect of this embodiment, the tube includes a diverter in the passage. In yet another aspect of this embodiment, the diverter is rotatably hinged on a wall of the tube. In still yet another aspect of this embodiment, the RSR device can include a sleeve surrounding the tube portion that includes a plurality of first apertures and the tube portion includes at least one second aperture.

In yet another embodiment of the invention, a respiratory secretion retention (RSR) device configured for connecting to an artificial airway can include a housing that defines a passageway for the flow of respiratory gases, a chamber defined by the housing where a portion of the chamber is configured to retain exhaled respiratory particulate and liquid, a patient port defined by the housing that is in fluid communication with an artificial airway, an access port opposite the patient port that is configured to provide access to the chamber and the patient port and a tube coaxially aligned and coupled to the access port and the patient port, the tube defining a passage between the access port and the patient port. In another aspect of this embodiment, the tube can include a diverter in the passage. In yet another aspect of this embodiment, the diverter is rotatably hinged on a wall of the tube. In still yet another aspect of this embodiment, the tube can include a first aperture and a second aperture.

In an embodiment of the invention the RSR device may include a port for instilling fluids, such as saline or medication. Medication may be aerosolized for delivery of medication to the airway.

In still another embodiment of the invention, a respiratory secretion retention (RSR) device configured to connect to an artificial airway can be provided. The respiratory secretion retention (RSR) device can include a housing that defines a passageway for the flow of respiratory gases, a chamber that is defined by the housing, where a portion of the chamber is configured to retain exhaled respiratory particulate and liquid, and an expiratory port of the housing, wherein the expiratory port is not parallel to a gas delivery port of the housing during some phase of use of the device. In an aspect of this embodiment, the housing is configured to provide for repositioning of the gas delivery port with respect to the expiratory port.

In still yet another embodiment of the invention, a respiratory secretion retention (RSR) device configured to connect to an artificial airway can be provided. The respiratory secretion retention (RSR) device can include a housing that defines a passageway for the flow of respiratory gases, a chamber that is defined by the housing, where a portion of the chamber is configured to retain exhaled respiratory particulate and liquid, and a clip coupled to the reservoir and configured to limit the volume, and therefore deadspace, of the reservoir to the area of the reservoir above the clip. In an aspect of this embodiment, the reservoir has an access port for the removal of the retained secretions.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, herein:

FIGS. 3A and 3B are cross-sectional schematic illustrations of yet another RSR device according to a certain embodiment of the present invention;

FIG. 5 shows schematic illustrations of yet another RSR device according to a certain embodiment of the present invention;

FIG. 7 shows schematic illustrations of yet another RSR device according to a certain embodiment of the present invention;

FIG. 12 shows cross-sectional schematic illustrations of variations of the RSR device shown according to a certain embodiment of the present invention;

FIG. 17 shows front schematic illustrations of variations of the RSR device shown according to a certain embodiment of the present invention;

FIG. 19 shows cross-sectional schematic illustrations of variations of the RSR device shown according to a certain embodiment of the present invention;

FIG. 22 shows cross-sectional schematic illustrations of variations of the RSR device shown according to a certain embodiment of the present invention;

FIG. 23 shows cross-sectional schematic illustrations of variations of the RSR device shown according to a certain embodiment of the present invention;

FIG. 24 shows cross-sectional schematic illustrations of variations of the RSR device shown according to a certain embodiment of the present invention;

FIG. 25 shows cross-sectional schematic illustrations of variations of the RSR device shown according to a certain embodiment of the present invention;

FIG. 26 shows cross-sectional schematic illustrations of variations of the RSR device shown according to a certain embodiment of the present invention;

FIG. 28 shows a cross-sectional schematic illustration of variations of the RSR device shown according to a certain embodiment of the present invention;

FIG. 29 shows cross-sectional schematic illustrations of variations of the RSR device shown according to a certain embodiment of the present invention;

DETAILED DESCRIPTION OF THE INVENTION

Figure 1A:
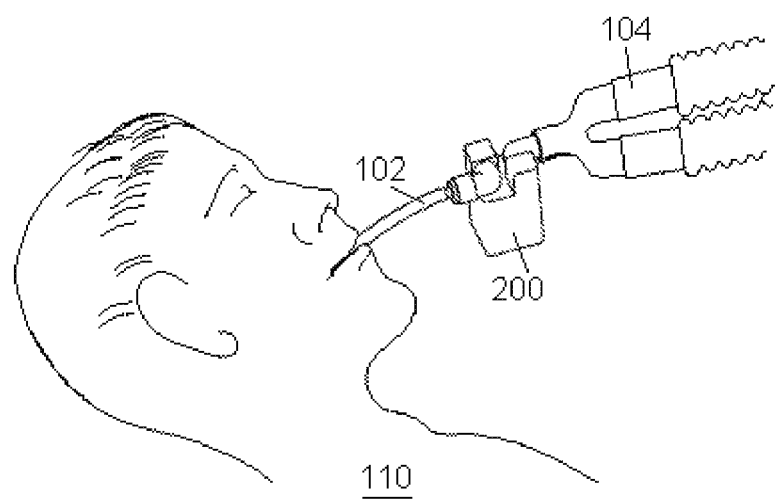
FIGS. 1A and 1B are schematic illustrations of the placement of an RSR device showing its attachment to an artificial airway in an intubated patient, where the RSR device is also connected to a ventilator circuit in FIG. 1A and wherein an RSR device is connected to a closed suction catheter in FIG. 1B.

During the exhalation phase of respiration, fluid is expelled from the lower respiratory tract. Most of the fluid is in the form of gases, but liquid and particulate matter (respiratory secretions) are also expelled. The RSR acts to separate the "respiratory secretions" from the respiratory gasses. For purposes of this disclosure, "respiratory secretions" may include sputum, mucus, mucus plugs, and/or other all other nongaseous matter which may be conveyed out of the lower respiratory tract and the like.

Embodiments of the present invention address deficiencies of the art in respect to artificial airways and respiratory secretion management, and provide a novel and non-obvious apparatus, system, and method for managing respiratory secretions and fluids in artificial airways. For purposes of this disclosure "artificial airway" may include any portion of the breathing conduit that connects to a patient's airway. In an embodiment of the invention, a Respiratory Secretion Retention (RSR) device for connecting to an artificial airway can be provided. A respiratory secretion retention device configured for connecting to an artificial airway comprising a housing that defines a passageway for the flow of respiratory gases, a chamber defined by the housing with a portion of the chamber configured to retain exhaled respiratory particulate and liquid, a patient port defined by the housing, which is in fluid communication with an artificial airway and at least one access port configured to provide access to the chamber and the patient port. In another aspect of this embodiment, the at least one access port can include a control valve, the control valve located in a downstream position of a passage of the access port to control access from the access port to the chamber.

In another embodiment of the invention, a respiratory secretion retention (RSR) device can include a housing that defines a passageway for the flow of respiratory gases, a chamber defined by the housing with a portion of the chamber configured to retain exhaled respiratory particulate and liquid, a patient port defined by the housing, which is in fluid communication with an artificial airway, a suction tube subassembly coupled to the housing, which defines a medical instrument passage and a suction tube portion and at least one access port configured to provide access to the chamber and the patient port. In another aspect of this embodiment the suction tube subassembly is coupled to a knob that provides for translation repositioning of the suction tube subassembly with respect to the housing.

In yet another embodiment of the invention, a respiratory secretion retention (RSR) device configured for fluidly connecting to an artificial airway can be provided. The respiratory secretion retention (RSR) device can include a housing that defines a passageway for the flow of respiratory gases, a chamber defined by the housing with a portion of the chamber configured to retain exhaled respiratory particulate and liquid, a patient side port coupled with the housing, which is in fluid communication with an artificial airway, at least one access port configured to provide access to the chamber and the patient port and a tube coaxially aligned and coupled to the access port and the patient port, to define a passage between the access port and the patient port. In another aspect of this embodiment, the tube includes a diverter in the passage. In yet another aspect of this embodiment, the diverter is rotatably hinged on a wall of the tube. In still yet another aspect of this embodiment, the RSR device can include a sleeve surrounding the tube that includes at least one first aperture and the tube includes at least one second aperture.

In illustration, FIG. 1A is a schematic illustration of an RSR device 200 attached to an endotracheal (ET) tube 102 in an intubated a patient 110. The RSR device 200 also can be attached to a ventilator circuit 104. The patient 110 is shown at an approximately 45-degree angle from level as this position as recommended by the Centers for Disease Control (CDC) for prevention of ventilator associated pneumonia. This illustration shows the relationship of the RSR device 200 used in association with a ventilator circuit 104. The device can also be used in association other ventilation tubes such as with a tracheostomy tubes, pharyngeal airway, or nasotracheal tubes. RSR 200 can be used alone with an artificial airway 102 without a ventilator 104, such as in a spontaneously breathing patient.

Figure 1B:
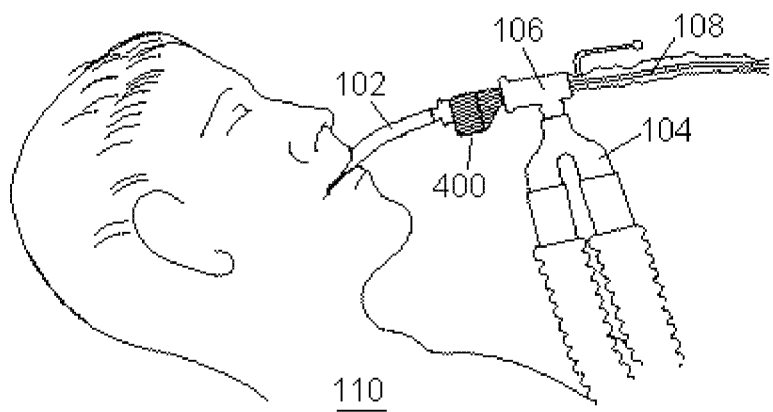

FIG. 1B illustrates a closed suction device 106 that can be connected between the RSR device 400 and the ventilator circuit 104. Certain embodiments of the present invention allow for the use of closed suction, and allow a suction catheter 108 of the closed suction device 106 to pass through RSR device 400 and into and through the patient's artificial airway in accordance with an embodiment of the present invention.

Figure 2A:
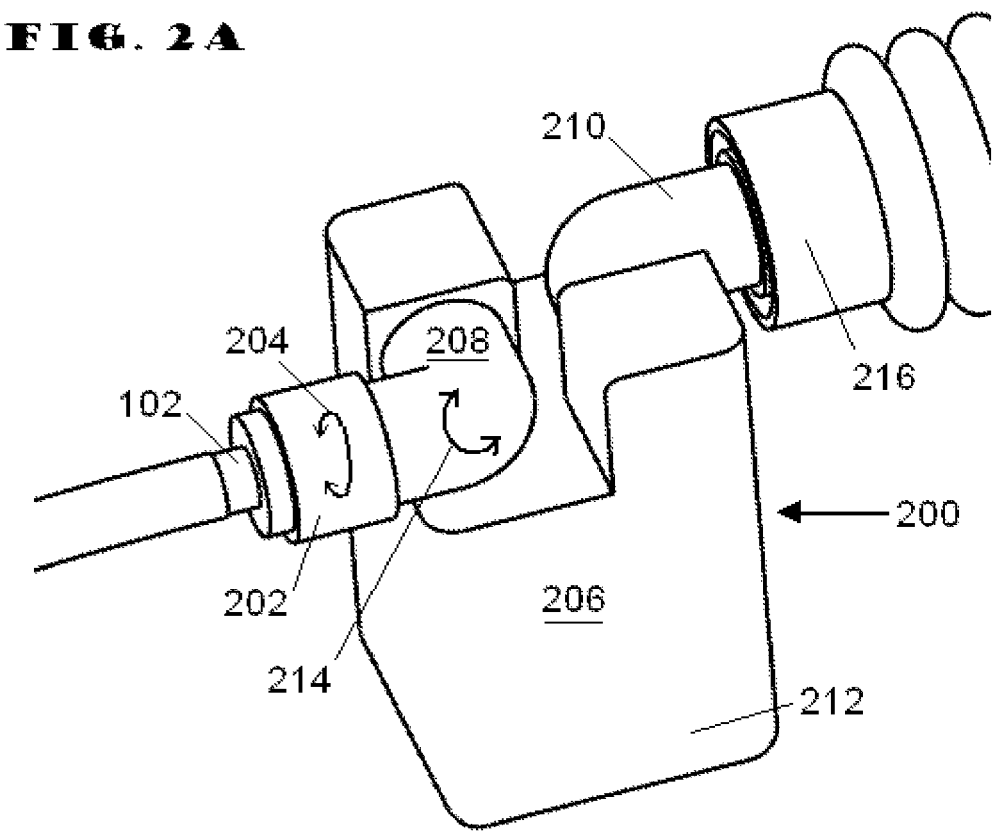
FIGS. 2A and 2B are schematic illustrations of an RSR device according to a certain embodiment of the present invention.

FIG. 2A is a schematic illustration of an RSR device 200 showing detail of its attachment to the endotracheal tube 102 and to the ventilator circuit. The RSR device can be applied so that gravity pulls secretions into a dependent area of the housing configured to retain the respiratory secretions. In embodiments, swivels can be added to the RSR to articulate the device in order to adjust it into a dependent position with respect to the collection of respiratory secretions, so that gravity pulls the secretions into a dependent area of the housing configured to retain the respiratory secretions.

The typically male fitting of the artificial airway 102 (as illustrated in FIG. 2A) fits into the typically female 15 mm fitting 202 which in preferred embodiments of this invention is configured as a swivel fitting. The rotation of this fitting is indicated by arrow 204. Fitting 202 can be connected to the RSR main body 206 with tube 208. Tube 208 can be straight or tube 208 may be angled and/or rotatable. A second tube 210 can be located on the ventilator side of the RSR device 200. Tube 210 can be straight or tube 210 can be angled and rotatable. In embodiments, tube 208 and tube 210 can swivel to allow the reservoir area of main body 206 to be placed in a dependent orientation while allowing the patient to be placed in a variety of positions. RSR device 200 can be designed to be used where its reservoir area 212 is placed below the artificial airway 102. Arrows 214 show the possible articulation of the angled and rotatable tubes in one embodiment in relation to the main body 206. Tube 210 is shown connected to a female ventilator connection 216 which also can contain a swivel. Thus, the main body 206 of the RSR 200 may move in two axes and the reservoir area 212 can be oriented in a dependent position with respect to gravity.

Figure 2B:
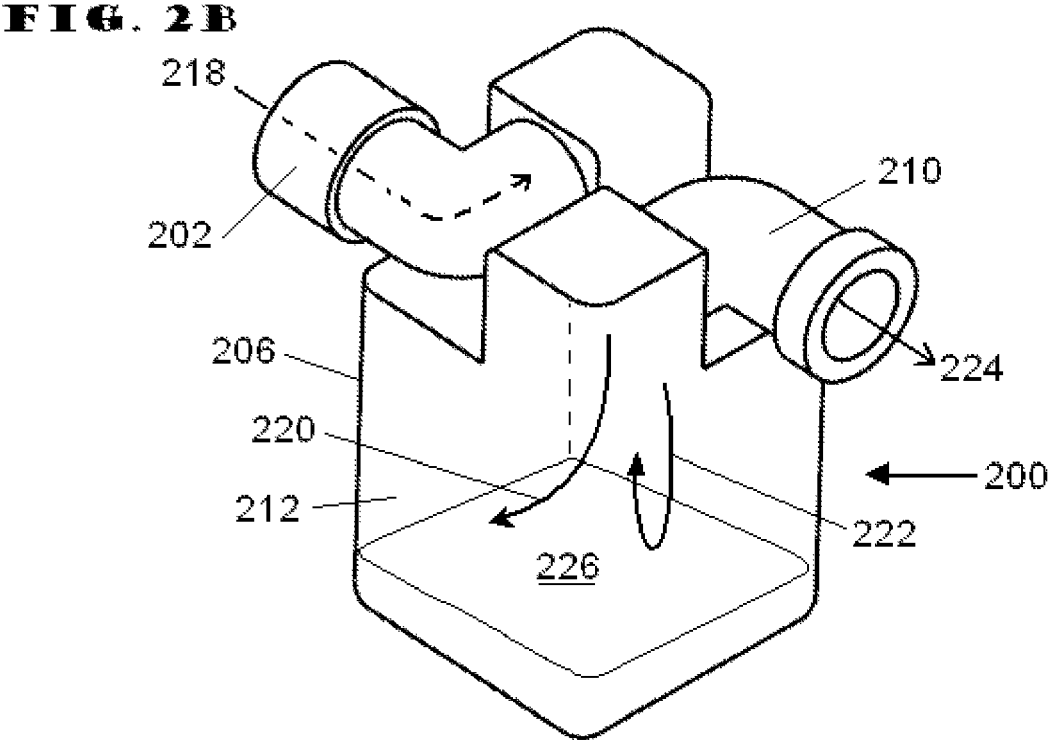

FIG. 2B further illustrates the air flow path of RSR device 200, illustrating its function. When the patient exhales, the flow enters connector 202 through the artificial airway into the RSR device 200 as shown by arrow 218. The momentum of the heavier fluids (respiratory secretions) causes them to both impact the interior surfaces of the RSR device and to fall out of the gas flow when the flow channel widens in the RSR and gas flow slows. This occurs in the RSR main body 206, and flow is indicated by arrows 220 and 222. Outflow of expiratory gasses is shown by arrows 224. On inhalation the gases reverse the flow direction in this embodiment of the invention. A fluid level of trapped respiratory secretions 226 is shown.

FIG. 2B shows RSR device 200 according to an embodiment of this invention which allows for control of the orientation of the reservoir area for collection of respiratory secretions. In order to retain the secretions, it is important that these secretions are unlikely to exit the reservoir area of the main housing 206 and unlikely to drain back into the patient's airway. Thus the ability to position the reservoir in a dependent orientation is an important feature of this invention. As the patient may be moved, it is advantageous to have a device which allows the orientation of the reservoir to move without disconnecting the device which would open the airway and allow possible contamination of the airway. A sputum trap that is insensitive to orientation has the disadvantage of an increased dead air space, and thus creates an added burden for $CO_2$ removal during respiration.

FIG. 3A illustrates others embodiment of an RSR device according to an embodiment of the present invention. In FIG. 3A, RSR device 300 is shown as a cross-sectional schematic. Patient airway port 302 allows for connection to artificial airway 102 typically with a 15 mm male connector via swivel connector 304. Ventilation source port 306 is shown with a 90 degree angled arm 308, which can rotate according to one configuration of the present invention, and is shown linked to a corrugated tubing 310 via swivel fitting 312. Ventilation source port 306 also can have a swivel.

Suction access ports 314 and 318 are plugged when not in use, as shown by plug 320 which seals port 318 in FIG. 3A, and plug 322 sealing port 314 in FIG. 3B. Access port 314 allows for the introduction of a suction catheter 316 that may suction the artificial airway 102 as illustrated in FIG. 3A, or may be used for the introduction of another instrument such as a bronchoalveolar lavage tube. Access port 318 allows for introduction of a suction catheter 316 as shown in FIG. 3B or for the introduction of another instrument such as a needle for example for removal of collected respiratory secretions which may collect in the reservoir area 324. In a variation of this device (such as described in FIG. 11A) a fitting for closed suction may be attached. Swivel connectors 304 and 312 allow for control of orientation of the RSR device 300.

FIGS. 3A and 3B also illustrate spill guards 326, which extend from the inner wall of the RSR device 300, and help prevent unintended emptying of the liquid contents of the reservoir back into the artificial airway or into the gas delivery limb in the case of movement or change in position.

Figure 4A:
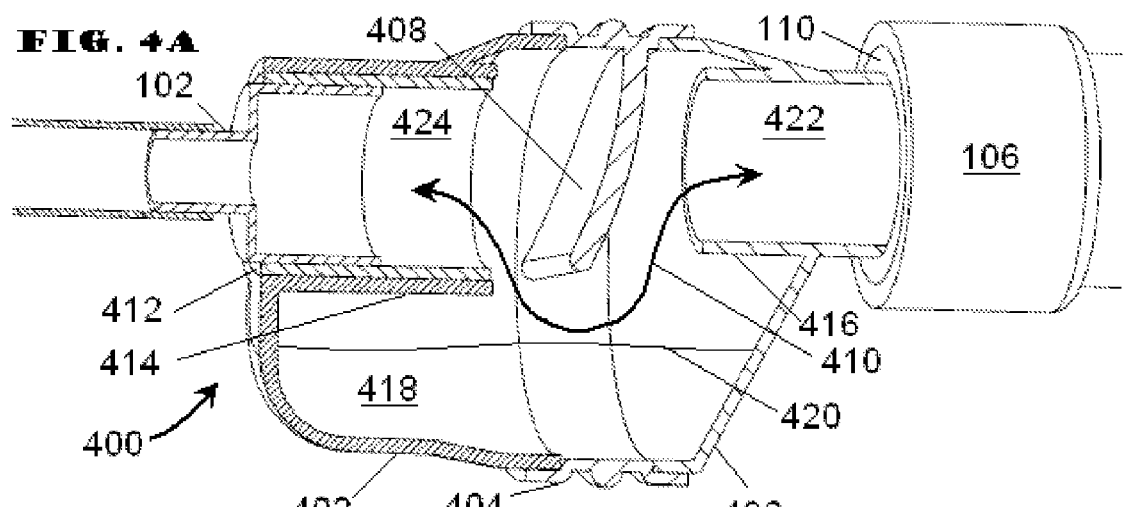
FIG. 4 shows cross-sectional schematic illustrations of yet another RSR device according to a certain embodiment of the present invention.
Figure 4B:
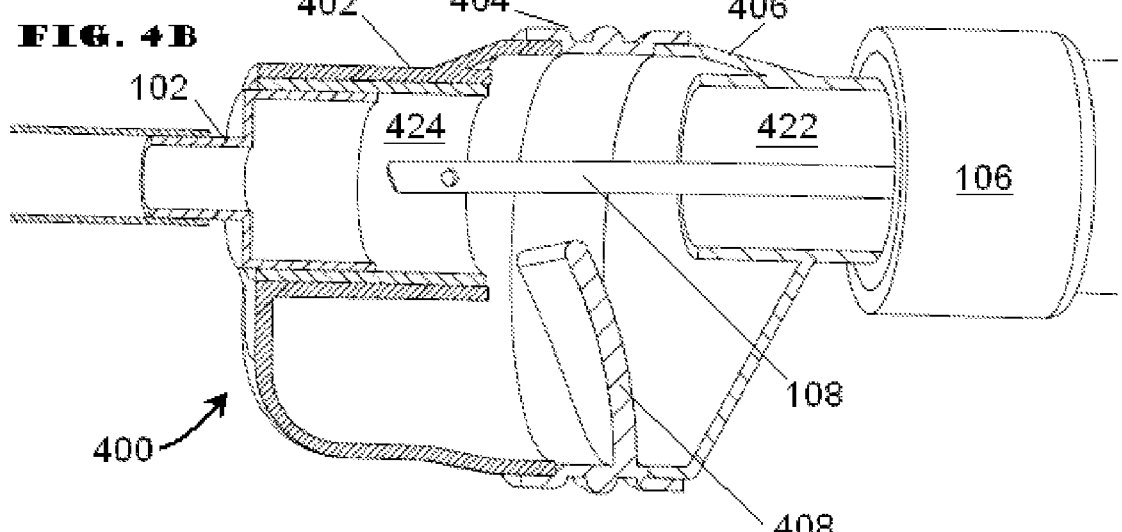
Figure 4C:
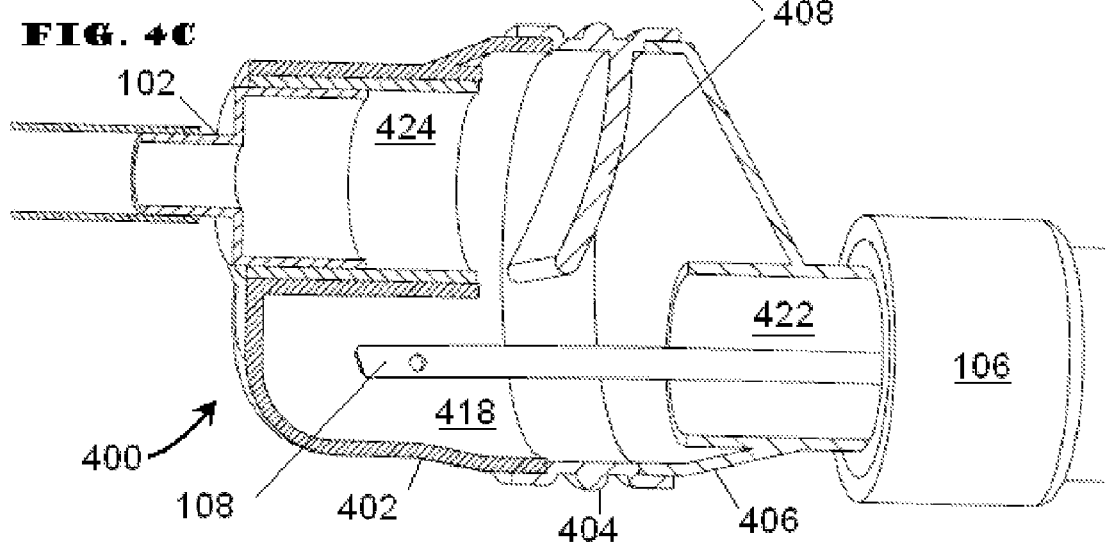

FIGS. 4A, 4B and 4C show cross-sectional schematic illustrations of another RSR device according to a certain embodiment of this invention, and each illustration shows a different conformational position of RSR device 400.

FIG. 4A is a cross sectional view of an RSR device 400 having a 3 sections which can rotate in reference to each other. RSR device 400 includes a patient interface section 402, a middle section 404 with a diverter 408, and a ventilation source section 406. FIG. 4A shows RSR sections 402, 404 and 406 in their typical use conformational orientation. RSR device 400 changes its conformation by changing the rotation positions of the sections 402, 404 and 406. RSR device 400 is configured so that the interior walls form a gas flow chamber, and a reservoir area for retained respiratory secretions.

The diverter 408 is configured to redirect the gas flow and to separate respiratory secretions that may be expelled during exhalation. Diverter 408 is disposed substantially perpendicular to the inflow path of the artificial airway 102. The diverter acts as an obstacle in the expiratory fluid pathway. As the respiratory secretions have more mass, and thus more momentum, they do not flow around the tortuous flow path created by the diverter as easily as the lighter gases in the exhalation, and are more likely to impact the surface of the diverter and the interior of the housing, to lose velocity and thus be separated from the gas flow. The fluid flow through the RSR devices also slows as a result of the widening of the cross-section of the flow path within the housing where the flow chamber is formed. This also decreases the momentum and acts to separate the respiratory secretions from the gases in the exhalation, and helps to retain these secretions within the chamber. A simplified gas flow path for the RSR device 400 when in the typical use position is illustrated by arrow 410.

The orientation of the reservoir area 418 helps retain the heavier fluids in the body of the RSR device 400. A fluid line 420 is shown to help illustrate fluid in the reservoir area. The dependent area 418 forms a reservoir for respiratory secretions. Swivel 412 in artificial airway port 424 allows for orientation of the RSR in relation to the artificial airway 102. An RSR device may also be configured with a swivel on the ventilator source section; however a swivel is not usually required on the ventilation source end of the RSR device 400 where it attaches to ventilation port 424 for use with a closed suction device 106, as the closed suction device typically contains its own swivel 110.

Also illustrated are spill guards 414 and 416, which show that the inlets to the connection ports from the inner housing of the RSR are configured to prevent the efflux of the retained secretions. Spill guards 414 and 416 advantageously prevent respiratory secretions and liquids from leaving the RSR device 400 and entering the HME, the breathing circuit and/or the artificial airway. Accordingly, the spill guards 414 and 416 help prevent egress of collected airway fluids into respiratory instruments when the patient turns or moves for example, and makes the device less susceptible to egress of retained fluids with movement of the patient.

In FIG. 4B, middle section 404 is shown rotated 180 degrees in relation to the typical use conformational position of sections 402 and 406. This allows diverter 408 to move out of a direct path between the ventilation source port 422 and the artificial airway port 424. As further illustrated in FIG. 4B, this conformational positioning allows the suction catheter 108 of the closed suction device 106 attached to the ventilation source port 422 to be advanced through the body of RSR 400 and into the artificial airway 102 for suctioning. After suctioning of the artificial airway, catheter 108 can be withdrawn into the closed suction device 106 and the RSR device 400 can be returned to it typical use conformational alignment. Other instruments such as a bronchial alveolar lavage device may also be passed through the RSR device in a similar manner.

In FIG. 4C, the ventilation source section 406 of RSR device 400 is shown rotated 180 degrees with relation to the typical use position of sections 402 and 404. This allows the suction catheter 108 of the closed suction device 106 to be advanced into the reservoir area 418 of the body of RSR device 400 for suctioning and evacuation of retained fluids. After clearing the retained respiratory secretions from the reservoir area, catheter 108 can be withdrawn into the closed suction device 106 and the RSR device 400 can be returned to it typical use position conformational alignment.

FIG. 5A is a schematic illustration of another RSR device according to a certain embodiment of this invention that illustrates a diverter 506 placed in the path of the gas flow, which allows for the passage of a suction catheter through the diverter 506. The arrow 508 in FIG. 5A shows the flow pattern of respiratory gasses through the chamber formed by the housing of RSR device 500 when it is in its typical conformational position for use for retaining respiratory secretions from exhaled respiration. Respiratory secretions are indicated by fluid line 510 where the housing of RSR device 500 acts as a reservoir area. The housing of device 500 has two main chamber sections. The patient interface section 502 is on the artificial airway side, and the ventilation source section 504 is on the ventilation source side. These two sections may have a circular cross section and are configured so that they are rotatably connected to one another.

In FIG. 5A section 502 is shown with a respiratory gas diverter 506 attached to a portion of the inner wall of device 500. Diverter 506 features an orifice 512. Orifice 512 is shown with a funnel shape which can act as an instrument guide for helping pass an instrument, such as suction catheter (108) through this orifice as shown in FIG. 5B. A valve 514, shown here as a flap valve, closes orifice 512 and limits expiratory flow from passing through the orifice 512, but allows the passage of an instrument as shown in FIG. 5B. In alternative embodiments, a valve may not be required as orifice 512 may be sized small enough such that it limits the passing of expiratory flows and secretions FIG. 5B illustrates RSR device 500 during the use of an instrument intended to enter the artificial airway. Valve 514 is shown in the open position, held open by suction catheter instrument 108, extending from a closed suction device 106. Other instruments such as a bronchial alveolar lavage catheter may also be used.

FIG. 5C illustrates RSR device 500 in a second conformational position. The two main chamber sections 502 and 504 are shown rotated 180 degrees in relationship to each other. This conformational arrangement allows the suction catheter 108 to be used to remove retained fluids and other respiratory secretions from the RSR device 500 which have collected in the reservoir area.

FIG. 5B further illustrates spill guards 518 and 520, which can be included in RSR devices according to certain configurations of this invention. The spill guards 518, 520 advantageously prevent respiratory secretions and liquids from leaving the RSR device 500 and entering the HME, breathing circuit, or the patient's artificial airway. Accordingly, the spill guards 518 and 520 help prevent egress of collected airway fluids into respiratory instruments or into the artificial airway, for example when the patient turns or moves. FIG. 5C also marks a swivel 522 in the artificial airway port connector.

Figure 6A:
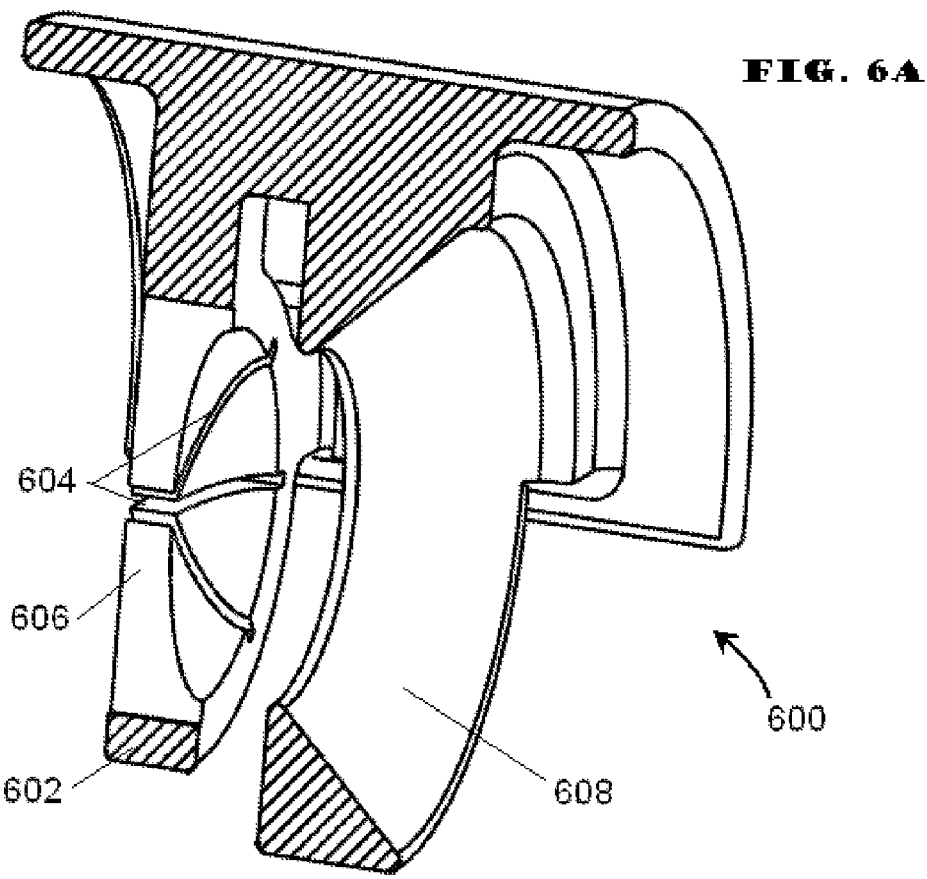
FIG. 6 shows schematic illustrations of details of various forms of diverters which may be utilized in the RSR device according to various embodiments of the present invention.
Figure 6B:
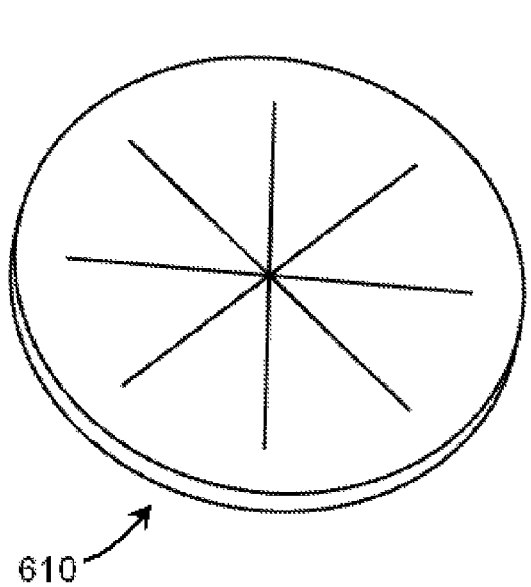
Figure 6C:
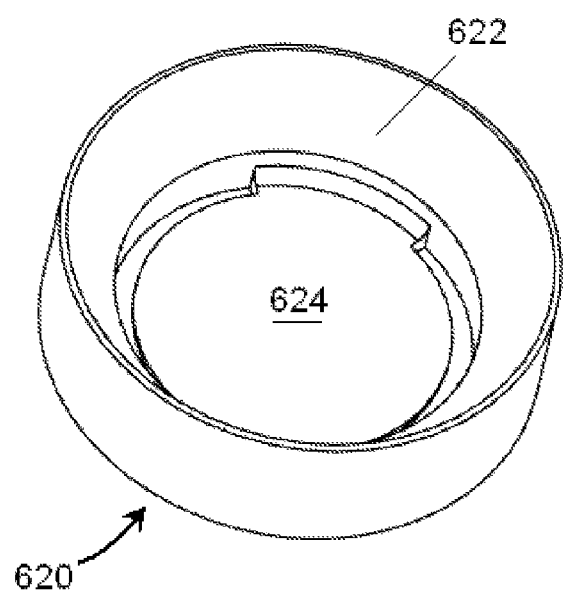

FIGS. 6A, 6B and 6C show schematic illustrations of various additional designs for diverters which allow for the passage of a suction catheter through the diverter portion of RSR devices according to certain configurations if this invention. FIG. 6A shows a cross-sectional illustration of a two-stage diverter. A first stage 602 of the diverter 600 is on the artificial airway port side of the diverter. Multiple slits 604 are shown perforating the first stage 602 of the diverter shown in the configuration of a star shaped, although various forms may be used within the concept of this invention. The first stage 602 may be thin at the center to decrease resistance and help guide passage of an instrument such as a suction catheter through the first stage. The first stage may use material which is flexible and allow deformation so that wedged shaped areas 606 formed by the perforations can bend out of the way of an instrument being passed through this stage of the diverter. The first stage 602 of the diverter 600 can be replaced with a simple flap 514, as is shown in FIG. 5A.

Diverter 600 has a second stage 608. Second stage 608 may have a larger outer diameter than the first stage 602 to enlarge the area of respiratory gas flow diverted. The second stage 608 of the diverter 600 is on the ventilation source side of a RSR device. Second stage 608 may have a funnel shape which can act as a guide for directing an instrument, such as a suction catheter, through the diverter.

FIG. 6B shows a diverter 610 with a star-shaped perforation. Other shapes, sizes and patterns of perforations could be utilized in different embodiments. FIG. 6C illustrates a diverter 620 with a funnel shaped outer ring 622, and a hinged flap valve 624. This diverter outer ring can have a sloped wall 622, which can help guide an instrument. These illustrations are not meant to in any way limit the type of diverter, which may be used to divert secretions or which can be used to allow an instrument to pass through this area of the RSR device, but rather to show some of the possible configurations. A diverter may have one or more stages and the stages may be of similar or different designs.

FIGS. 7A, 7B, 8A and 8B are schematic illustrations constructed in accordance with a further embodiment of the present invention showing an RSR device which allows conformational changes of the device.

FIG. 7A shows a perspective view of a configuration of another embodiment of the invention. RSR device 700 has a connector 710 which allows connection to an artificial airway port and a connector 720 that allows connection to a ventilation source. In a preferred configuration these connectors are standard 15 mm respiratory connectors. In embodiments, connector 710 is a female 15 mm swivel fitting and connector 720 is a male 15 mm fitting which can accept connection to a closed suction device or to a ventilator circuit. RSR device 700 has a ventilation housing 705. Housing 705 has a reservoir portion 750 for collecting secretions. Reservoir 750 can be integral to housing 705 or a separate component. Reservoir 750 may be suctioned through the ventilation housing or may be suctioned through a separate port in the reservoir itself. In embodiments, housing 705 can be flexible by being constructed of a non-rigid material, having thin walls, or by other means known to achieve flexibility. A flexible ventilation housing allows for a conformational change in terms of the alignment of the connector 720 with certain other parts of the structure of the RSR device 700. This conformational change may be achieved through methods such as rotation, bending, translation, etc. A bellows area 715 in the ventilation housing 705 is shown as a way to implement a conformational change.

FIG. 7A RSR device 700 can include a support structure 725. Support structure 725 can interface with connector 710, connector 720 and/or ventilation housing 705. Support structure 725 can be integral to one of these components, such as connector 710. In embodiments, support structure 725 can contain a track 736 for interacting with key 735 to allow the RSR device 700 to be held in at least two different conformational positions. Key 735 may extend from connector 720 on a support arm 740. Key 735 can move through track 736. In another embodiment, a key feature or its mating detail in the support structure 725 can deflect to allow for movement and placement into different conformational positions. Various techniques such as tracks, snaps, ratchets, detents, etc. are known for maintaining conformational positions. Support structure 725 also can have a cage 730. Cage 730 can protect a reservoir portion 750 of the housing 705 from inadvertent compression, while allowing for compression with finger pressure, for example, when desired by the user to help evacuate the contents of the reservoir 750.

FIG. 7A shows RSR device 700 in a straight position, which would be used when the device is in normal use, and during suctioning of the artificial airway with a closed suction unit, or when introducing an instrument into the artificial airway as shown in a cutaway view in FIG. 7B.

Figure 8A:
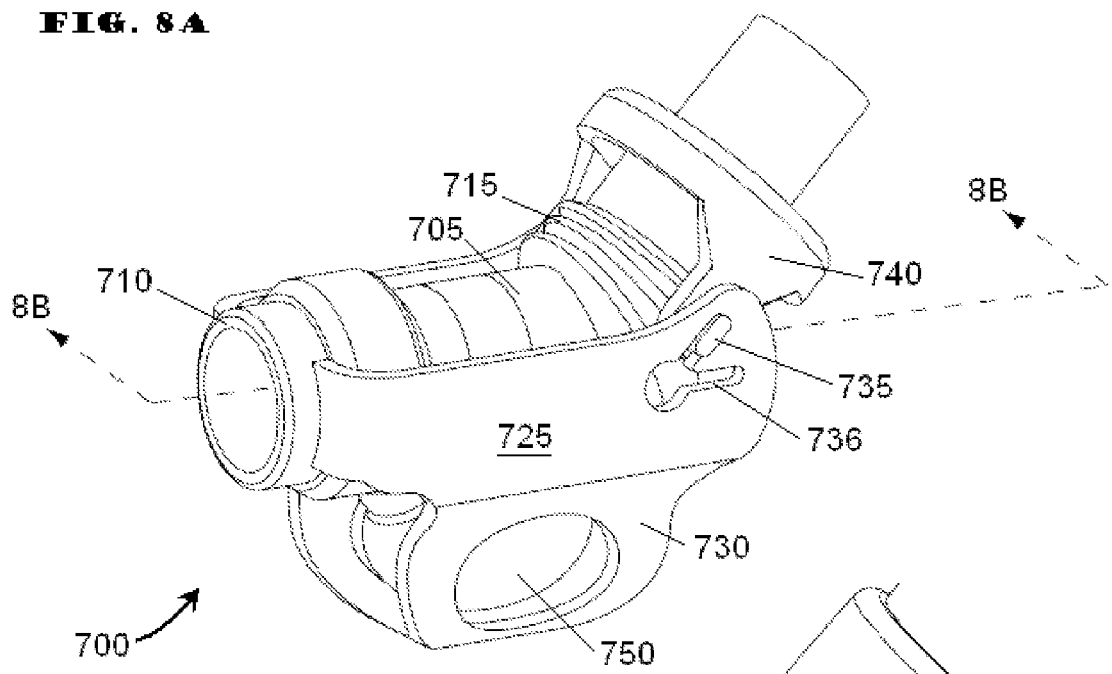
FIG. 8 shows additional schematic illustrations of the RSR device shown in FIG. 7 according to a certain embodiment of the present invention.
Figure 8B:
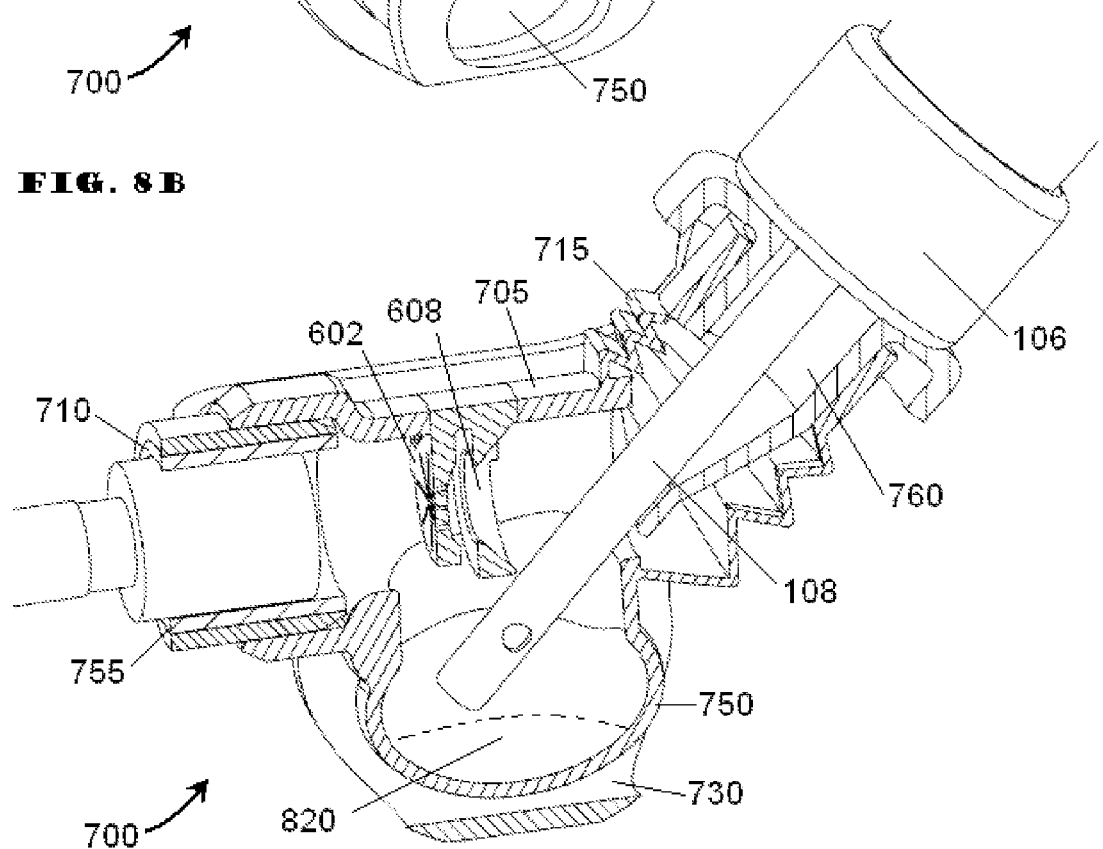

FIG. 8A shows device 700 in a secondary position. In the secondary position, the control key 735 is in a secondary position and the bellows area 715 section of ventilation housing 705 is in a flexed position. This secondary position allows a suction catheter to be inserted into the reservoir area 750 for evacuation of the pooled secretions as shown in FIG. 8B. The reservoir area 750 may be made of a flexible material and may be squeezed by the operator during suctioning to help remove collected respiratory secretions.

FIG. 7B shows a cutaway view of RSR device 700. The catheter 108 can be seen supported by instrument guide 760, and passing through the second stage 608 of diverter 600, which also acts as an instrument guide due to its funnel like shape. The catheter then passes through the first stage 602 of the diverter 600 which acts as a valve, diverting respiratory secretions when closed but allowing passage of the instrument.

FIGS. 8A and 8B show the position for the RSR device in a secondary conformational position for use during suctioning of the reservoir.

FIG. 8B illustrates the RSR device 700 in a cross-sectional view in a secondary conformational alignment which may be used to remove respiratory secretions 820 from reservoir 750 using an instrument such as closed suction catheter 108. Catheter guide 760 can help guide a flexible instrument.

Figure 9:
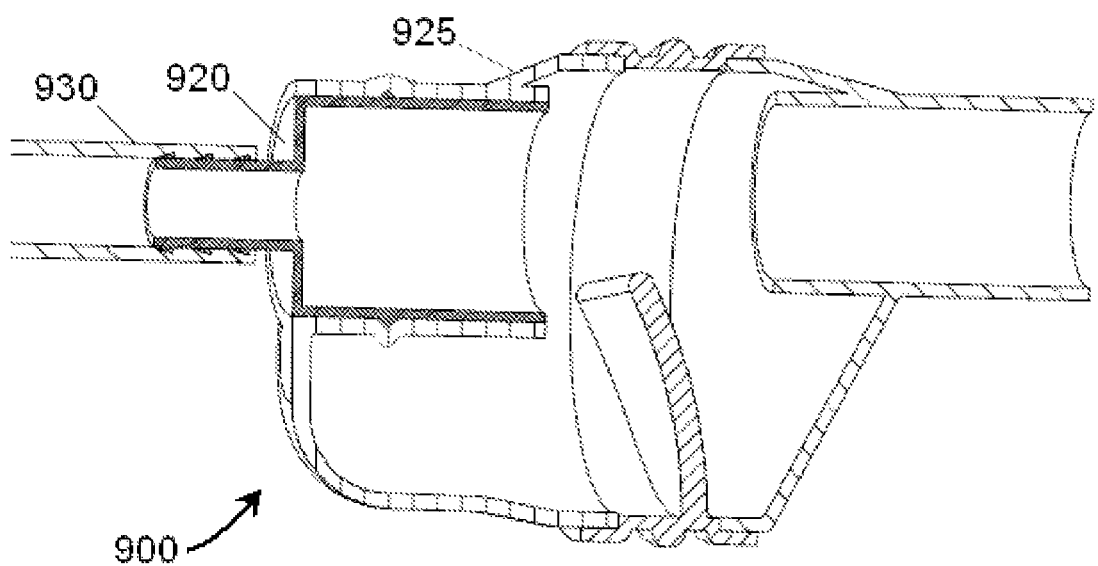
FIG. 9 shows cross-sectional schematic illustrations of variations of the RSR device shown according to a certain embodiment of the present invention.

FIG. 9 is a cross-sectional schematic illustration in accordance with a certain embodiment of the present invention configured with a connecter 920 shown as a Christmas tree or male barbed connector, for connection directly to an endotracheal tube 930. The connector 920 may also connect to the endotracheal tube without the barbs. This configuration replaces the fitting commonly used as the attachment to artificial airway as shown herein in other illustrations, for example the male fitting of artificial airway 102 and port 302 as illustrated in FIG. 3A. A connector such as shown in FIG. 9 allows the RSR device to be integrated as a single unit with the patient artificial airway. FIG. 9 also illustrates that connector 920 can act as a swivel within housing section 925 which allows the device to be rotated in relation to the endotracheal tube. This allows for positioning of the reservoir area of the RSR in a dependent orientation, and also decreases the strain and traction of the artificial airway upon the patient.

In other embodiments, the RSR device 900 can be directly attached to a tracheotomy tube, as RSR device 900 functions to replace the adapter that is standard with ET and tracheotomy tubes. In embodiments, RSR device 900 can be packaged and sterilized with the artificial airways.

Figure 10A:
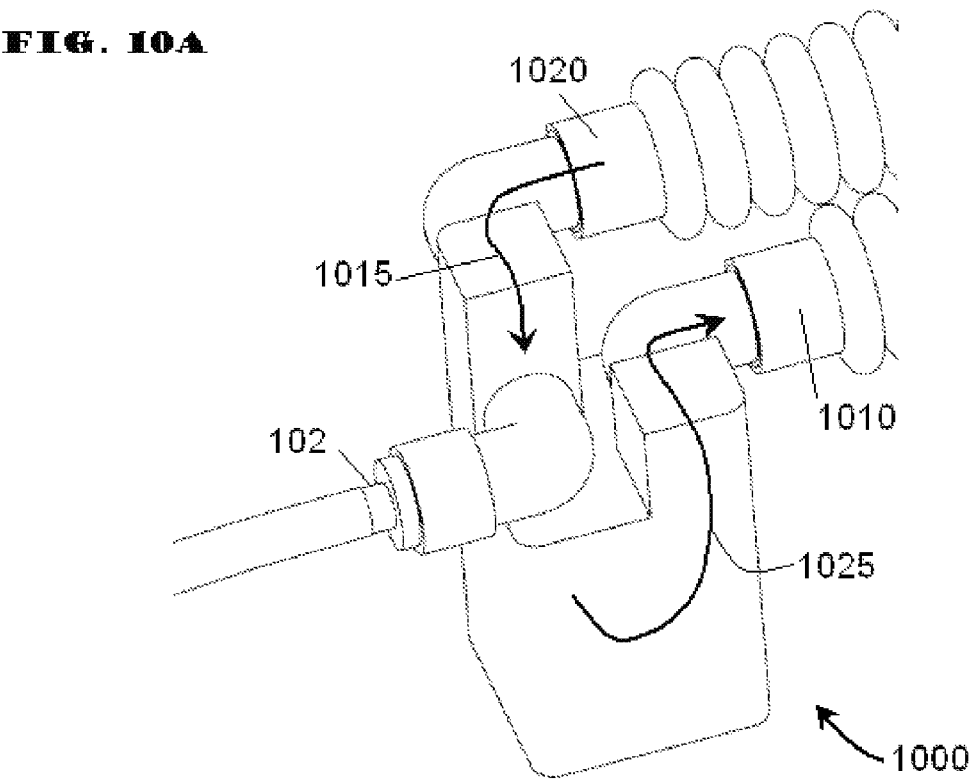
FIG. 10 shows cross-sectional schematic illustrations of variations of the RSR device shown according to a certain embodiment of the present invention.
Figure 10B:
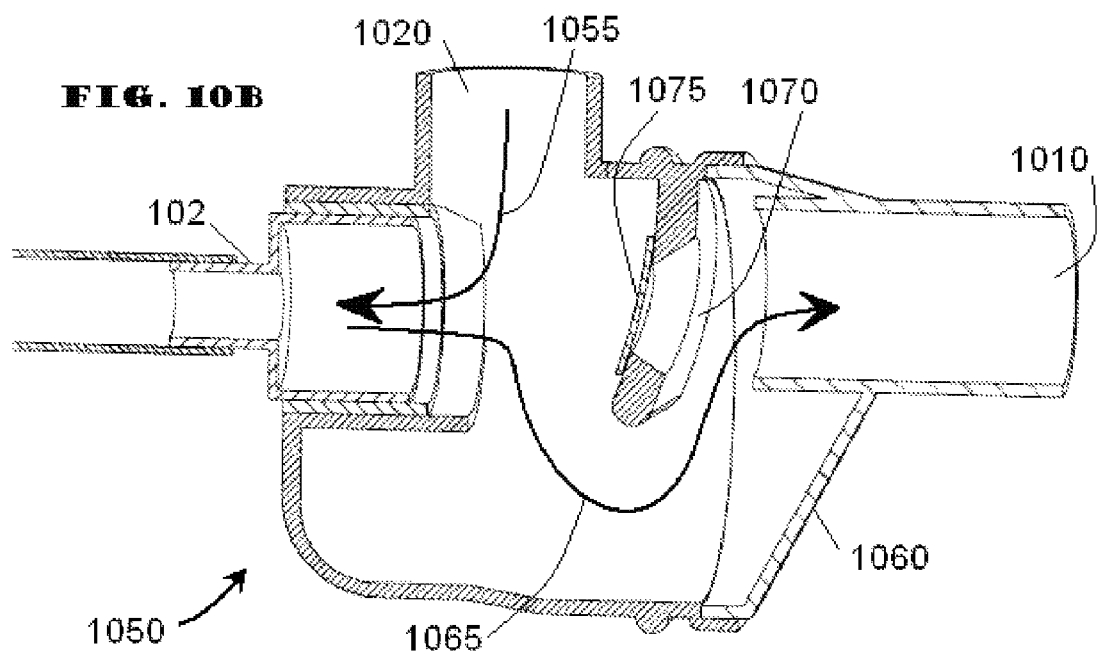

FIGS. 10A and 10B are yet other schematic illustrations of RSR device embodiments according to the present disclosure where the respiratory inflow tract enters at the patient end of the RSR device, and the exhaled gasses pass through the RSR device. This has the added advantage of greatly reducing the volume of dead air space while still providing a larger reservoir. This inspiratory bypass that allows a larger reservoir area, and can be used alone or in combination with valves to prevent efflux of respiratory secretions back into the airway. FIG. 10A illustrates an RSR device 1000 similar to device 200 shown in FIG. 2A. FIG. 10B illustrates an RSR device 1060 similar to RSR device 500. In FIG. 10A, the gas supply enters through delivery port 1020 close to the artificial airway. In device 200, the gas flow is bi-directional and reverses direction during the respiratory cycle. In contrast, in device 1000 flow though the RSR body passes in one direction; away from the patient. Arrow 1015 illustrated the direction of delivery of respiratory gas to the subject from the delivery arm of the ventilator circuit. During expiration breath passes through the RSR device 1000 as shown by arrow 1025 and into the exhalation arm of the ventilator circuit.

In FIG. 10B, the gas supply enters the RSR device through delivery port 1020 and flows to the subject near to the artificial airway 102 as shown by arrow 1055. In similar device 500, the gas flow is bi-directional and reverses direction during the respiratory cycle. In contrast, in RSR device 1050, flow thought the RSR body passes in one direction; away from the patient, as shown by arrow 1065, and flows towards expiratory port 1010.

Another advantage to having a gas inflow tract on the patient side is that if the reservoir side is opened for suctioning, negative pressure is unlikely to occur, and there is less likelihood of patient contamination from the environment. Alternative to having a patient end inflow port configured integral into the RSR, a Tee can be added on the patient end which is placed between the artificial airway and the RSR device. A disadvantage of this that the suction catheter must be extended further to suction the artificial airway.

Figure 11A:
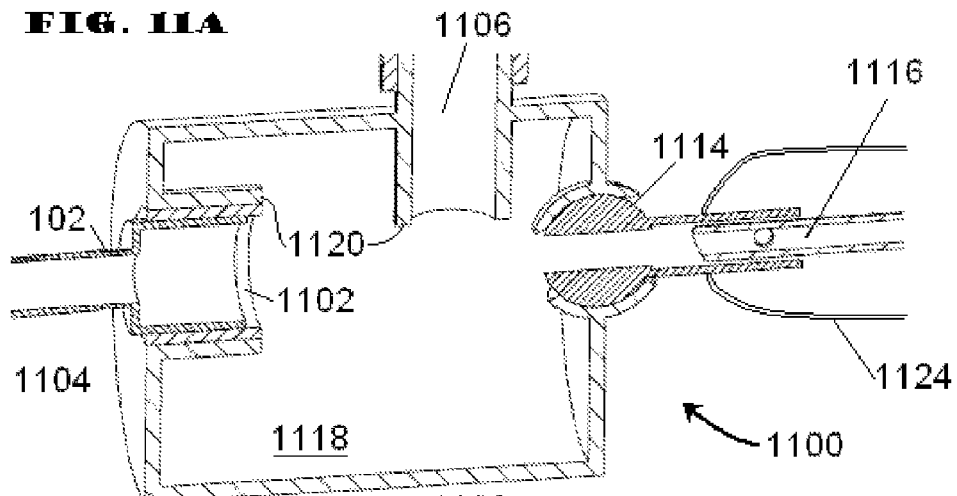
FIG. 11 shows cross-sectional schematic illustrations of variations of the RSR device shown according to a certain embodiment of the present invention.
Figure 11B:
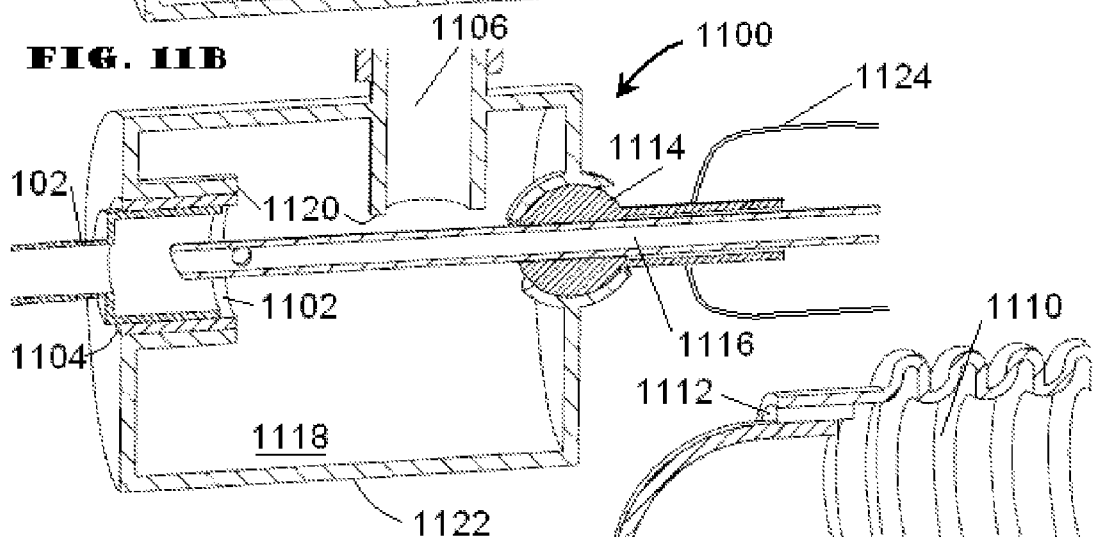
Figure 11C:
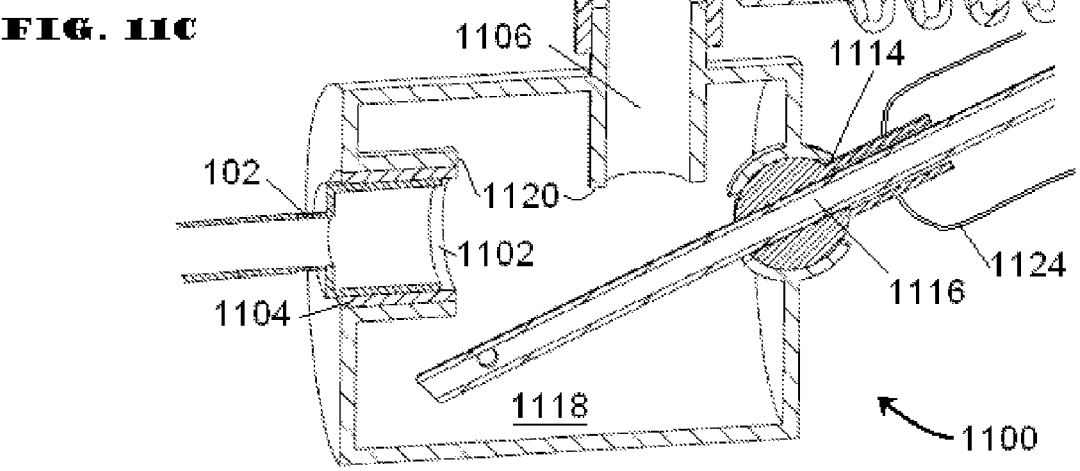

FIGS. 11A and 12A illustrate additional embodiments of the current invention, wherein closed suction allows clearance of respiratory secretions from the artificial airway and from the RSR device. FIG. 11A shows a RSR device 1100 with an integrated closed suction catheter. In RSR device 1100, a suction catheter 1116 can be connected by a fitting 1114. Fitting 1114 allows the suction catheter 1116 to be advanced and withdrawn into and through the body 1122 of RSR device 1100. Fitting 1114 also can pivot to allow the catheter 1116 to enter into the artificial airway for suctioning as shown in FIG. 11B or to enter the reservoir area 1118 for evacuation of accumulated respiratory secretions from the RSR device as illustrated in FIG. 11C. Catheter 1116 is sealed within a protective sheath 1124, which is only partially visible in FIGS. 11A, 11B and 11C. Sheath 1124 is flexible and allows the catheter to be advanced into and retracted from the housing of the RSR device, and prevents contamination of the catheter from the external environment.

FIG. 12A illustrates yet another embodiment of the invention showing an RSR device with an integrated fitting for a closed suction connection. Device 1200 is configured to attach to artificial airway 102 with connector port 1202. A swivel connector, such as 1204 allows a connection, which places less stress on the artificial airway. Stress on the artificial airway may be injurious to the patient, may cause damage to the trachea, and may induce leaking of seal of the balloon of the endotracheal balloon. This may allow upper airway secretions to enter the lung, which is considered to be a risk factor for ventilator associated pneumonia.

FIGS. 12A and 12B show a gas flow path diverter 1206. Diverter 1206 contains a valve 1208 and bevels 1210 which act an instrument guide. A suction catheter 108 is illustrated in FIG. 12B through the diverter. The diverter 1206 is shown as being supported by support arms 1212. In other configurations, the diverter could be attached to an interior wall, a swivel connector, or to the ventilation source side of the RSR device.

FIGS. 12B and 12C show device 1200 illustrated with a fitting 1214 to allow for connection to a closed suction device 106. The fitting 1214 is designed to allow flow of gas. Fitting 1214 can pivot to allow the catheter 108 to enter into the artificial airway for suctioning as shown in FIG. 12B or to enter the reservoir area 1216 for evacuation of accumulated respiratory secretions from the RSR device 1200 as illustrated in FIG. 12C. The catheter 108 would be withdrawn into the closed suctioning device during its typical use.

Figure 13A:
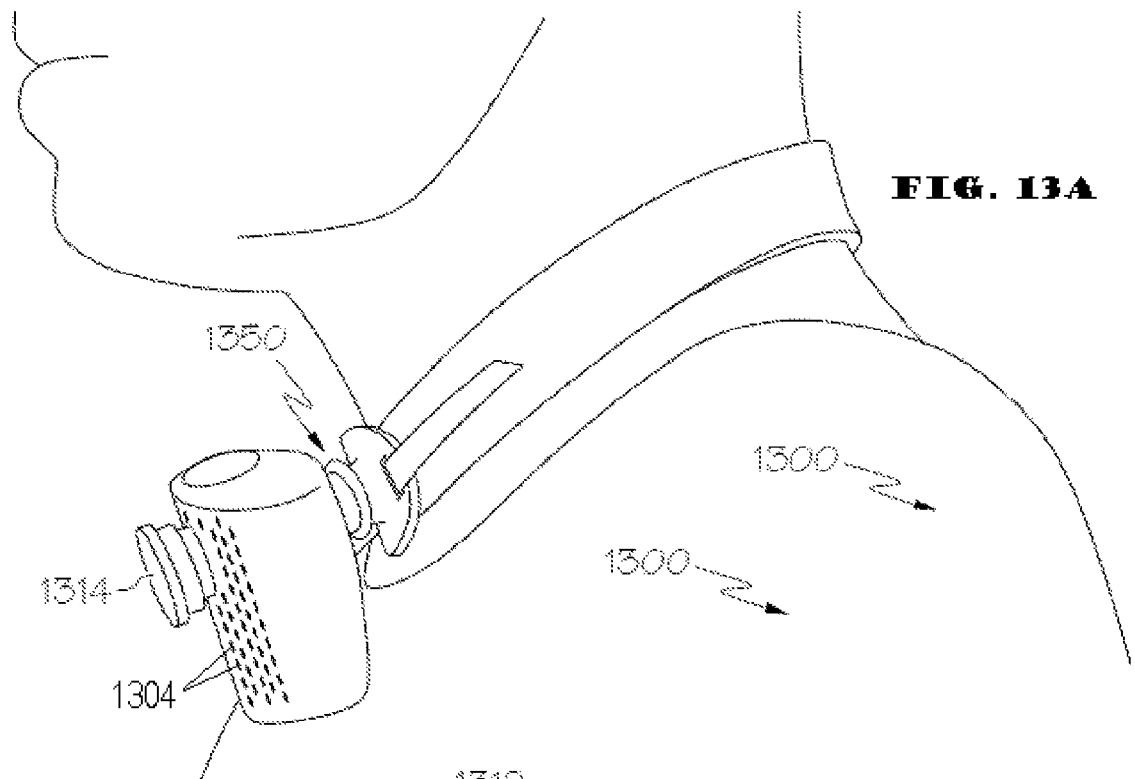
FIG. 13A shows lateral schematic view of a configuration of an RSR device shown according to a certain embodiment of the present invention.
Figure 13B:
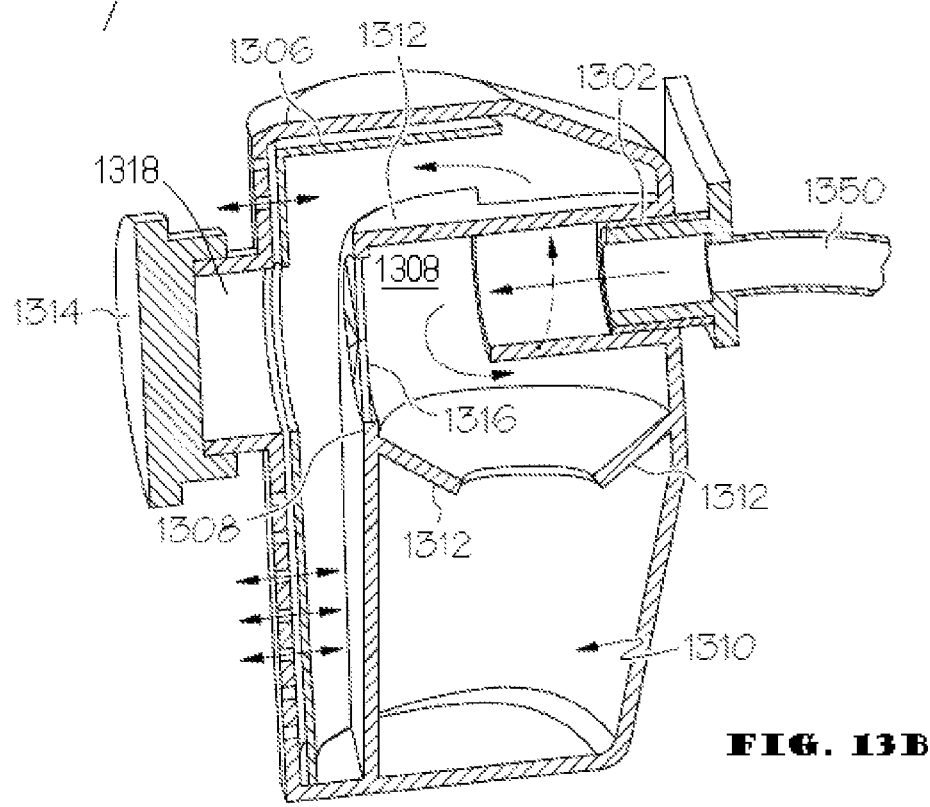
FIG. 13B shows a frontal schematic view of the RSR device shown in FIG. 13A.

FIG. 13 illustrates yet another embodiment of an RSR device according to the present invention. RSR device 1300 is configured to fit to a tracheostomy tube 1350. A connector 1302, e.g., a swivel connector, is shown in FIG. 13A which allows orientation of the reservoir area 1320 in a dependent position for collection of respiratory secretions. In contrast to having a single gas flow vent (e.g., exhalation port) configured to couple with another device, device 1300 is an example of a configuration of an RSR device with multiple perforations or vents 1304 for direct flow to and from the device to the atmosphere. Vents are illustrated on the anterior surface, but can be on other surfaces. The anterior and upper portion is shown containing heat and moisture exchange (HME) material 1306 which acts as a filter helping to protect the patient's airway from airborne pathogens. The HME material also acts to capture heat and humidity from the patient's exhaled breath, and release it back to the patient upon inhalation, thus avoiding drying of the airways and avoiding energy loss from the patient. A large total vent area is advantageous in that it provides low flow resistance and efficient heat and moisture exchange. FIG. 13B illustrates that within device 1300, an airflow diverter wall 1308 helps capture respiratory secretions and guide them towards the reservoir area 1310 and towards the lower internal surface of the housing. Diverter wall 1308 helps to separate respiratory secretions from the gas flow. RSR device 1300 also has spill guards 1312 which help retain secretions in the reservoir area and help prevent spillage of retained respiratory secretions in the event that the patient's position is moved.

The exhaled breath flows first towards the deflector and then flows through the HME material 1306 where heat and moisture is captured and the remaining exhaled gas can pass to the atmosphere through vents 1304. On inspiration, atmospheric gas enters through vents 1304 is filtered, heated and humidified before flowing into the patient airway.

The device in FIG. 13B shows an orifice 1318 with a cap 1314 on the front surface of device 1300 which may be opened if suctioning is desired. Deflector wall 1308 is illustrated in FIG. 13B with a valve 1316 that allows a suction catheter or other instrument to be introduced into the artificial airway 1350 with access being given by opening cap 1314. In certain embodiments, RSR device 1300 may be configured so that a suction catheter or other instrument may be directed to enter reservoir area 1310. This allows for removal of respiratory secretions from the device. In other configurations, the RSR device 1300 can be configured without these features.

Not shown in the illustration, the cap may cover a second valve at the surface of the RSR device 1300. Such a valve would help prevent sputum from entering the room during suctioning, and limit inhalation of unfiltered air. Valve 1316 can have, for example a conformation similar to valve 610 shown in FIG. 6B. In another embodiment, the device can be made with a valve without a cap. In a configuration of the invention, one or more valves can be configured as an anti-asphyxiation valve which would open in the case that the resistance to flow through HME material and surface vents became higher than desirable.

Device 1300 may be preferentially constructed with a housing made of a flexible material, such as silicone, to make wearing the device more comfortable for the patient. The device may also be configured so that it may be cleansed and the HME material or HME section may be replaced.

Figure 14:
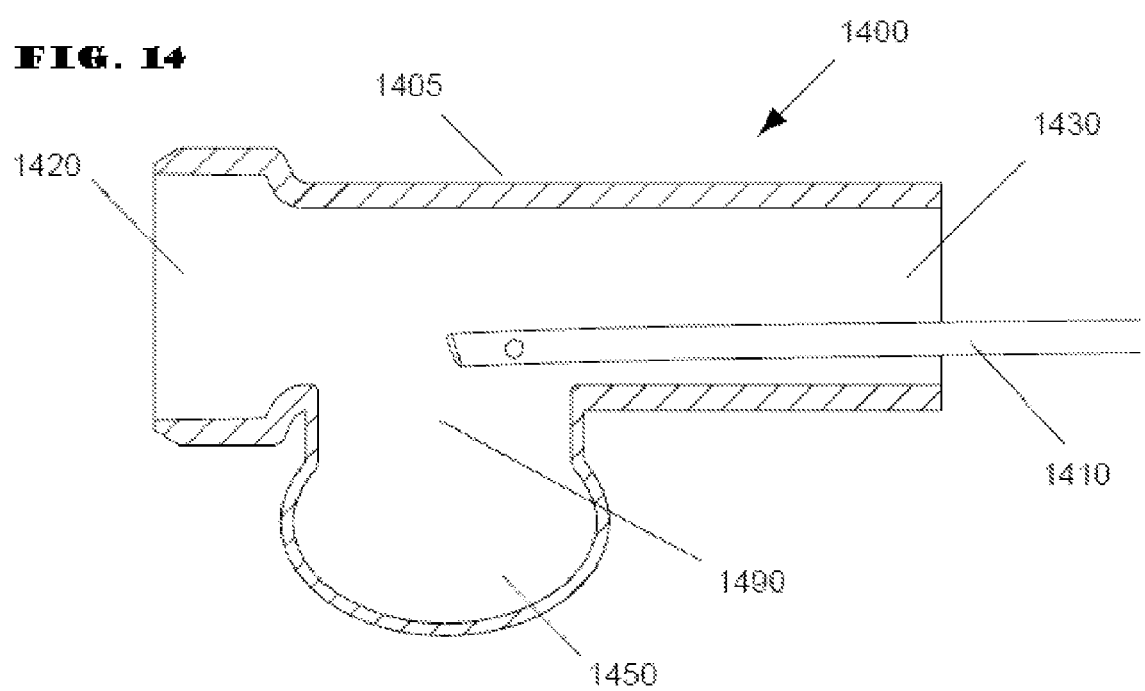
FIG. 14 shows a cross-sectional schematic illustration of the RSR device according to a certain embodiment of the present invention.

FIG. 14 illustrates another embodiment of an RSR device 1400 according to the present invention. Housing 1405 has a patient port 1420 for connection to an artificial airway and a ventilation port 1430 for connection to a closed suction device and/or ventilation source (not shown). The ports can have swivel connectors to facilitate orientation of the RSR device. Housing 1405 also has a reservoir 1450 for collection of respiratory secretions. Opening 1490 allows secretions to enter the reservoir as they pass through the housing. The opening may be sized large enough to maximize the entry of the secretions. Features such as a diverter, which were described in other embodiments of this invention, can also be located in RSR device 1400 to further separate secretions from the gas flow and direct them into the reservoir. The RSR device 1400 may be disposed of with the contained secretions, or the secretions may be removed by a variation of methods such as removing the reservoir, draining the reservoir, or suctioning the reservoir and/or housing, etc. In embodiments, the reservoir may be flexible. A flexible reservoir may be collapsed, for example by squeezing, or translated into the housing in order to move the secretions into main section of the housing. Once the secretions are moved there, the secretions may be removed, for example by a suction catheter 1410.

Figure 15A:
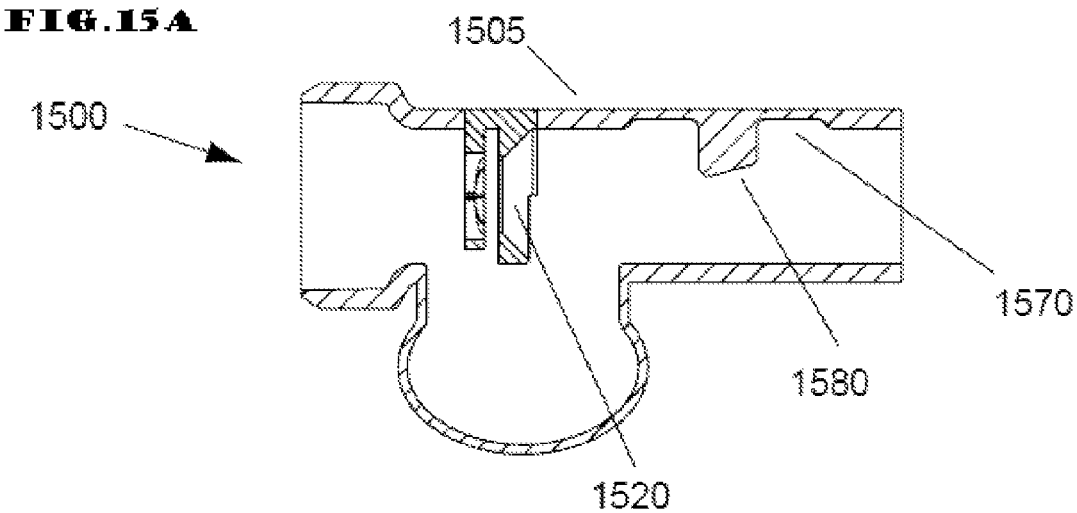
FIG. 15 shows cross-sectional schematic illustrations of variations of the RSR device shown according to a certain embodiment of the present invention.
Figure 15B:
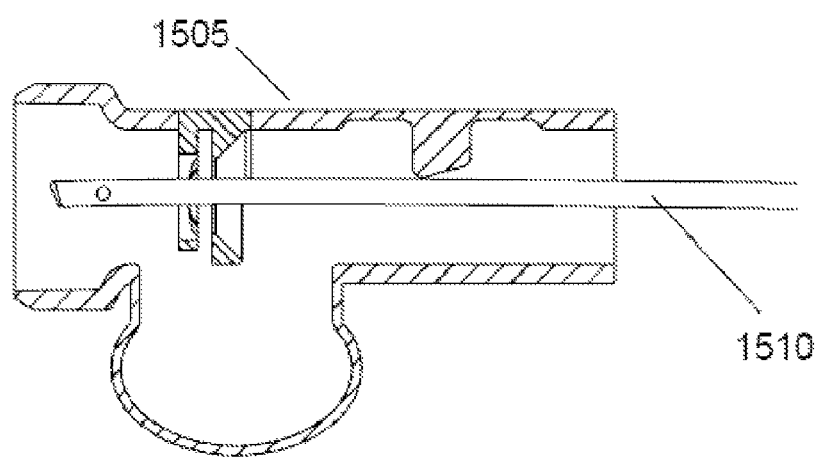
Figure 15C:
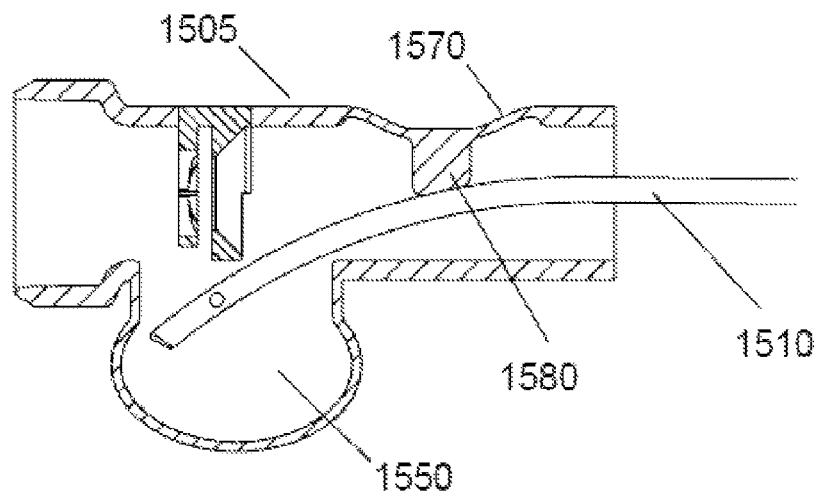

FIG. 15A illustrates a RSR device 1500 similar to RSR device 1400. Housing 1505 can include a diverter 1520 as shown. Housing 1505 further can include a flexible portion 1570 with a guide 1580. The flexible portion 1570 can provide the guide to translate with respect to the interior of the housing. In FIG. 15B, a suction catheter 1510 is shown passing through the housing in order to suction an artificial airway of a patient. In FIG. 15C, the guide is shown translated further into the housing and therefore directing the suction catheter into a reservoir 1550 in order to remove secretions.

Figure 16A:
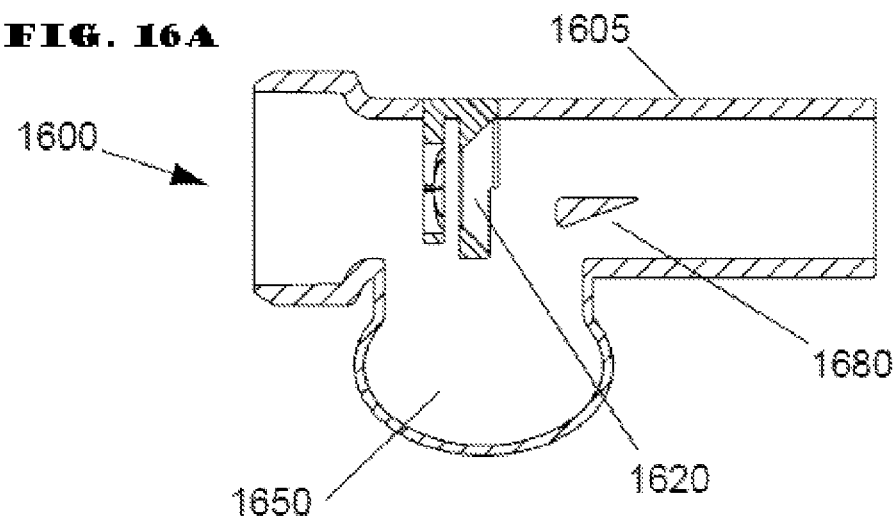
FIG. 16 shows cross-sectional schematic illustrations of variations of the RSR device according to a certain embodiment of the present invention.
Figure 16B:
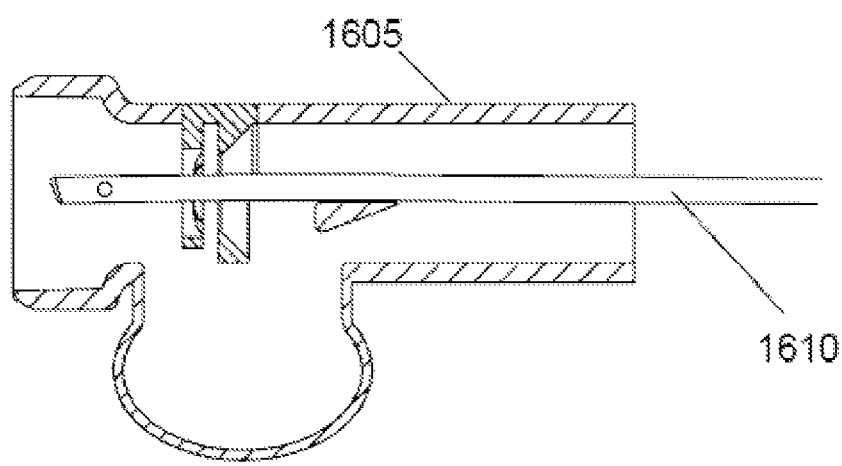
Figure 16C:
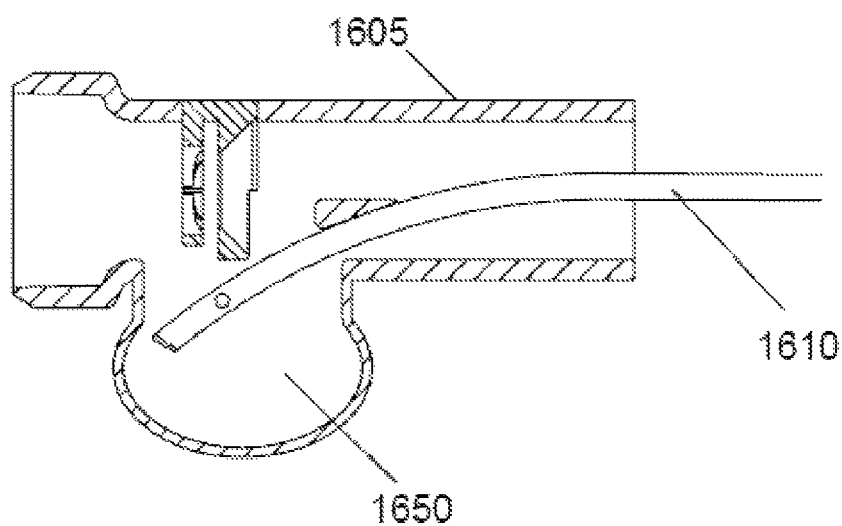

FIG. 16A illustrates a RSR device 1600 similar to RSR device 1400. Housing 1605 has a diverter 1620 as shown. Housing 1605 has a guide 1680 that can direct an instrument, such as a suction catheter, towards the diverter or towards a reservoir 1650. Guide 1680 can be integral to housing 1605 or it could be a separate piece. If a separate piece, guide 1680 may pivot within housing 1605 allowing for increased directional control of a suction catheter. A pivoting guide may extend through the housing in a sealed manner to allow a user to externally control the angle of the guide. An external knob or similar detail could be attached to the extended part of the guide to allow the user to pivot the guide. In FIG. 16B, a suction catheter 1610 is shown passing above the guide in the housing in order to suction an artificial airway of a patient. In FIG. 16C, a suction catheter 1610 is shown passing below the guide directing the suction catheter into a reservoir 1650 in order to remove secretions.

FIGS. 17A and 17B illustrate another embodiment of and RSR device 1700 according to the present invention. Housing 1705 has a patient port 1720 for connection to an artificial airway and a ventilation port 1730 for connection to a closed suction device and/or ventilation source (not shown). The ports may have swivels to facilitate orientation of the RSR device. Housing 1705 also has a reservoir 1750 for collection of respiratory secretions. The reservoir 1750 may be flexible or have a flexible extension, which allows the size of the reservoir to be controlled. Features such as a diverter, which were described in other embodiments of this invention, may also be located in the RSR device 1700 to further separate secretions from the gas flow and direct them into the reservoir 1750. A drain or vacuum port 1760 may be included which allows for emptying the contents of the reservoir. In one embodiment, a RSR device 1700 can include a drain port 1760 and a fluid instillation port 1765. Instillation port 1765 can be used to instill saline or other fluid to help clear the respiratory secretions which have collected in the reservoir, especially if these secretions are thick or tenacious.

A clip 1770 can be applied to the reservoir 1750 to divide the volume of the reservoir to an upper area 1752 above the clip 1770 and a lower area 1754 below the clip 1770. A smaller reservoir volume is advantageous to limit dead space volume, especially for example in smaller patients and in patients with certain respiratory diseases. A larger reservoir volume is advantageous to allow for less frequent clearing of the secretions in the RSR device 1700. The position of the clip 1770 may be adjustable on the reservoir and therefore limiting the volume in the upper area 1752 as desired by the user.

As shown in FIG. 17B, clip 1770 could be removed and then attached above the fluid instillation port 1765, allowing the reservoir to be cleared while maintaining a minimum deadspace in the upper area 1752, maintaining a closed air circuit, and preventing the patient from experiencing the effects of the clearing, such as with a vacuum. When the reservoir 1750 begins to fill with respiratory secretions during use, the clip position may be adjusted to enlarge the upper area 1752. The clip 1770 also can be removed to allow the secretions to pool in the lower area 1754 of the reservoir, and then the clip may be reattached to again limit the reservoir volume. The clip 1770 could then also be used as a tool to force the secretions lower into the lower area 1754 of the reservoir. The secretions now in the lower area 1754 of the reservoir may be drained through a port 1760 or may be maintained there until the device or reservoir is disposed.

Several other possible configurations of this invention can easily come to mind by those skilled in the art, which are within the scope of this invention. For example, the route for passage of a suction catheter in most configurations may as well be used for passage of a stylette for use in facilitating intubation, for passage of a bronchoscope or the like. The connection port for the artificial airway for RSR devices can have a 15 mm inner diameter (ID); however, it could be any ID necessary to connect with various artificial airway tubes or the like. The connection port of the ventilation source can have 15 mm outer diameter; however, it could be any ID necessary to connect with a ventilator circuit, closed suction device, or similar device, or may be used open to the atmosphere.

All RSR device embodiments of this invention could be integrated into other components found in breathing circuits, such as artificial airways, medical instruments (for example suction catheters), HMEs, medication delivery devices, tubing, fittings, etc. Tubing could also be connected between any ports described in all RSR device embodiments of this invention and other components found in breathing circuits. For example, tubing, such as flexible tubing, can be connected between the RSR device and the artificial airway and/or a HME. It is also understood that many of the RSR device embodiments of the inventions are bi-directional and will function to trap liquid coming from either side of the RSR device. In fact, with slight modification, all of the disclosed embodiments could function bi-directionally as would be apparent to one skilled in the art.

Many of the respiratory secretion retention (RSR) devices discussed above include an instrument port for receiving a medical instrument, e.g., a catheter of a closed suction device, a catheter of an open suction device, a bronchoscope, a drug delivery device, and the like. In embodiments, the instrument port can be configured on a RSR device so that the artificial airway is still closed to the atmosphere even when the medical instrument is not present. For example, plugs 320 and 322 shown in FIGS. 3A and 3B respectively can accomplish this. Alternatively, a valve could be used to maintain a closed system. For example, when a medical instrument is not present, a valve can be configured so it remains in a closed state. When a medical instrument is inserted, the valve can open to allow the medical instrument to enter into and/or through the RSR device. Various valve types configured to allow passage in one direction can be utilized, e.g., a flapper valve, a check valve, a biased valve, a pucker valve, a duckbill valve and the like. Also, valves that open when a certain pressure is reached (i.e. "cracking pressure") can be utilized, such as a valve that activates when medication is introduced via a syringe that is connected to an RSR device.

Figure 18A:
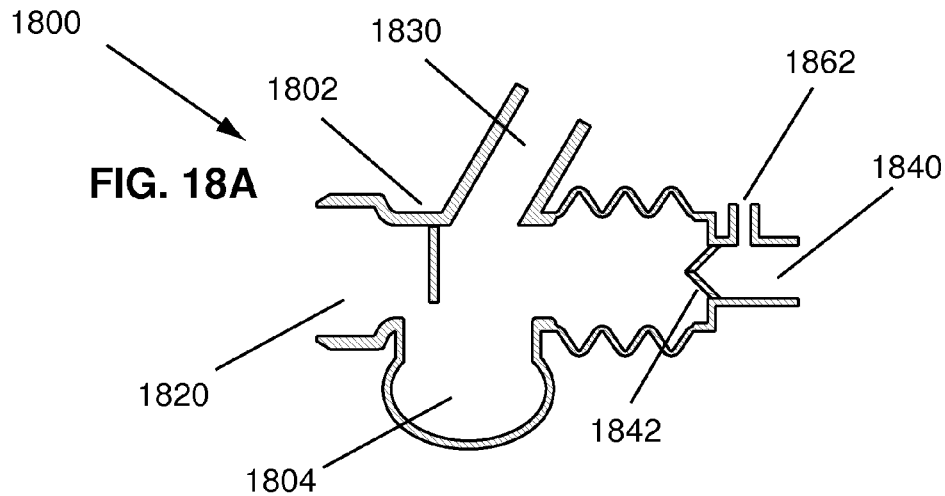
FIG. 18 shows cross-sectional schematic illustrations of variations of the RSR device shown according to a certain embodiment of the present invention.
Figure 18B:
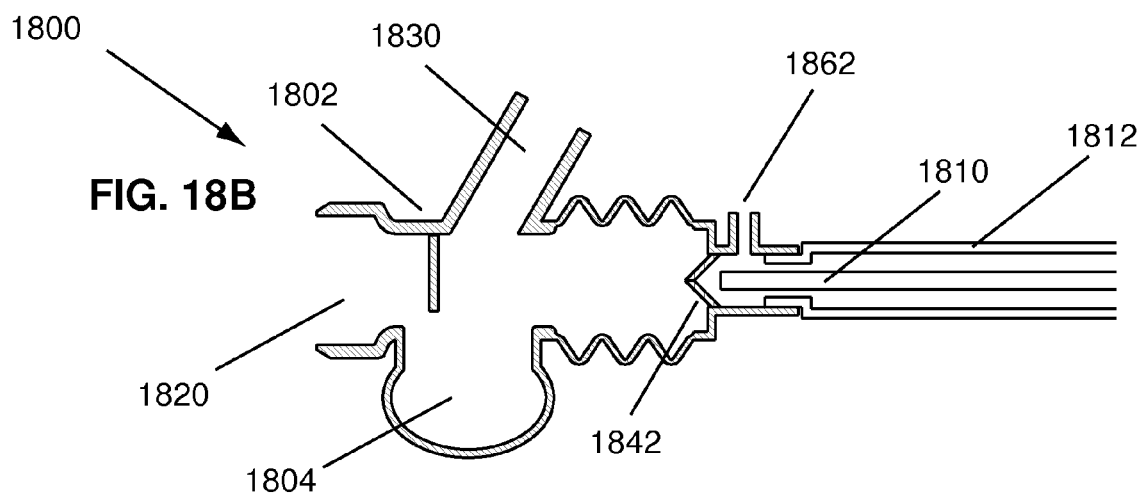
Figure 18C:
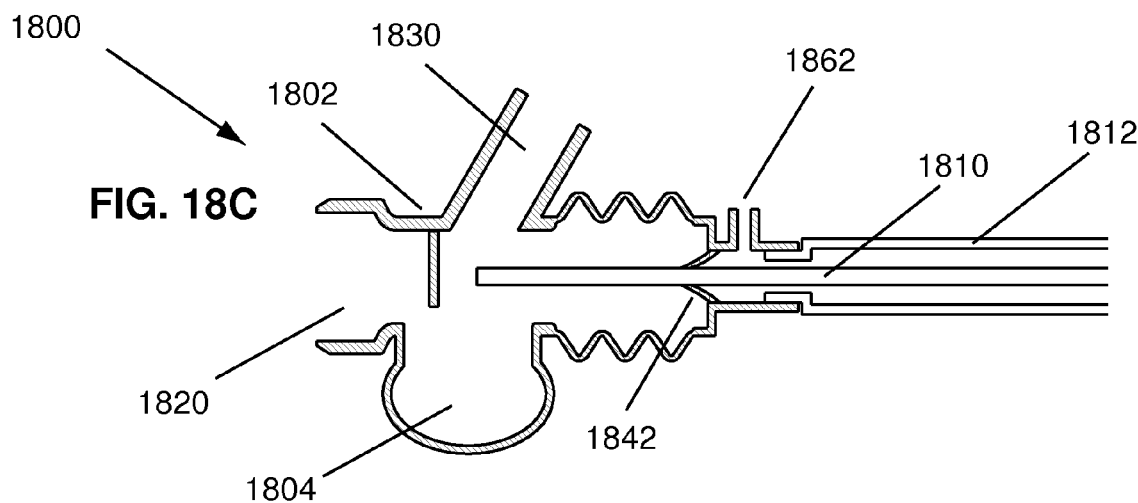

In illustration, FIG. 18A is a cross-sectional view of another embodiment of an RSR device 1800 according to the present invention. Housing 1802 can include an instrument port 1840 for receiving a medical instrument, a patient port 1820 for connection to an artificial airway and a ventilation port 1830 for connection to a closed suction device and/or ventilation source (not shown). Housing 1802 also can have a reservoir 1804 for collection of respiratory secretions. In embodiments, housing 1802 can be similar to housing 705 of RSR device 700 to allow for conformational change in terms of the alignment of the instrument port 1840 with certain other parts of the structure of the RSR device 1800. RSR device 1800 further can include a valve 1842 located in the instrument port 1840. In FIG. 18A, the valve 1842 is shown in a closed position or state. FIG. 18B illustrates a medical instrument 1812, e.g., a closed suction device connected to the instrument port 1840. FIG. 18C illustrates catheter 1810 of the closed suction device 1812 inserted through valve 1842. Valve 1842 is shown in an open position or state. Referring again to FIG. 18B, RSR device 1800 also can have a fluid instillation port 1862. Fluid may be instilled through port 1862 to lavage or clean a portion of the medical instrument 1812, such as a portion of catheter 1810 of a closed suction device 1812. Closed valve 1842 prevents the fluid from entering portions of the RSR device that are closed to the atmosphere during this cleaning process. Referring again to FIG. 18A, ventilation port 1830 could be at an angle, for example 45 or 90 degrees, or could be parallel to the patient port 1820. Any of the ports 1820, 1830, or 1840 could have swivels as discussed in previous RSR device embodiments. Features such as a diverter, which were described in other embodiments of this invention, may also be located in the RSR device 1800 to further separate secretions from the gas flow. Features and methods for clearing an RSR device of respiratory secretions described in other embodiments of this invention, drain ports, and/or or suction ports may also be located in the RSR device 1800. Also, other RSR device embodiments discussed in the present invention could have a valve, a fluid instillation port, and/or ventilation port.

FIG. 19A illustrates another embodiment of an RSR device. RSR device 1900 can include a housing 1902, which can include a patient port 1920, a ventilation port 1930, an instrument port 1940 and a rotatable housing section 1904. All three ports 1920, 1930 and 1940 can have swivel connectors. The instrument port 1940 can include a control valve 1942, as described in other embodiments, which controls access to reservoir 1950 and maintains a closed system to atmosphere. The patient port 1920 and the ventilation port 1930 are configured to extend sufficiently far into reservoir 1950 of RSR device 1900 to prevent the unintended emptying or displacement of liquid contents from the reservoir 1950 into an artificial airway of a patient or into the ventilation delivery branch or limb. In FIG. 19A, the ventilation port 1930 and the instrument port 1940 are shown parallel to each other. The instrument port 1940 and the patient port 1920 can be aligned so a medical instrument 1910 can enter into the reservoir 1950 of RSR device 1900 and travel through to the patient port 1920. Instrument port 1940 can be repositioned as shown in FIG. 19B, to enable a medical instrument 1910 to enter the reservoir 1950 at a different angle. The different angle can facilitate the removal of the fluid contents 1956 by use of medical instrument 1910, such as a suction catheter. FIG. 19C further illustrates a cross-sectional perspective view of RSR device 1900. The rotatable housing section 1904 can include a first connecting section 1906 and a second connecting section 1908. In operation, as rotatable housing section 1904 is rotated downward from a first position to a second position, the two connecting sections 1906 and 1908 maintain a sealed connection with the inner wall of housing 1902. The sealed connection will insure that no fluid contents 1956 escape from reservoir 1950.

Figure 20A:
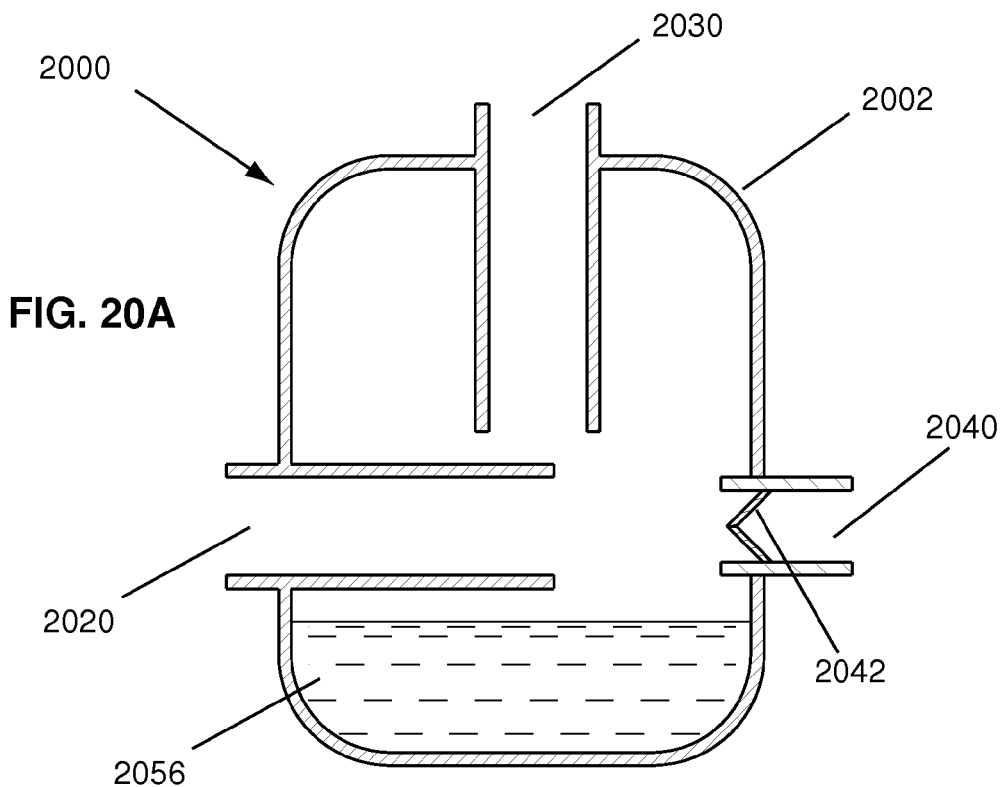
FIG. 20 shows cross-sectional schematic illustrations of variations of the RSR device shown according to a certain embodiment of the present invention.
Figure 20B:
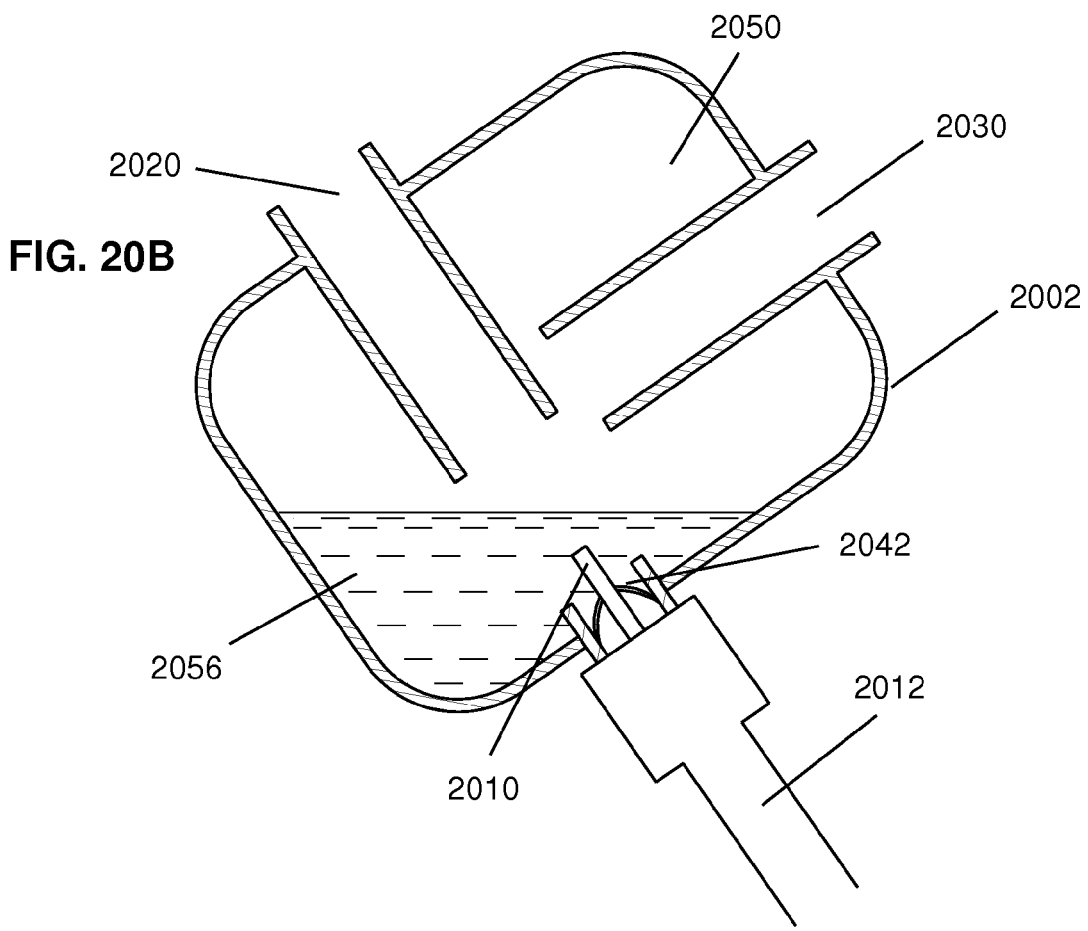

FIG. 20A illustrates another embodiment of an RSR device. RSR device 2000 can include a housing 2002, which can include a patient port 2020, a ventilation port 2030 and an instrument port 2040. All three ports 2020, 2030 and 2040 can have swivel connectors. The instrument port 2040 can include a control valve 2042 as described in other embodiments. The patient port 2020 and the ventilation port 2030 are configured to extend sufficiently far into reservoir 2050 of the RSR device 2000 to prevent the unintended emptying or displacement of liquid contents from the reservoir 2050 into an artificial airway of a patient or into the ventilation delivery branch. Patient port 2020 and ventilation port 2030 may be on the same plane as shown in FIG. 20A or may be on different planes similar to the patient and ventilation ports of RSR device 1900. In this embodiment, it is preferred that the ventilation port 2030 and the instrument port 2040 be angled relative to each other to allow adequate clearance between a medical instrument 2012 and a ventilator circuit (not shown). This angle may facilitate the setup of the ventilator circuit. For example, as illustrated in FIG. 20A, the ventilation port 2030 and the patient port 2020 are at a substantially 90 degree angle of orientation to each other. The instrument port 2040 and the patient port 2020 can be aligned so the medical instrument 2010 could enter into RSR device 2000 and move through the patient port 2020. FIG. 20B illustrates RSR device 2000 in a tilted position, which can allow the fluid contents 2056 to shift towards the instrument port 2040. A catheter 2010 of suction device 2012 is illustrated removing the fluid contents 2056 from the reservoir 2050. If additional secretions enter the reservoir 2050 through the patient port 2020 and splash the top surface of the fluid contents, the angled relationship between the ventilation port 2030 and the patient port 2020 makes it less likely that any liquid contents will splash into the ventilation port 2030. In embodiments, a drain or an additional port can be included in another portion of the RSR device 2000 to allow for further removal of the liquid contents of reservoir 2050. In embodiments, a flexible tube (not shown) may be connected between the patient port 2020 and the artificial airway. In embodiments, a flexible tube (not shown) may be connected between ventilation port 2030 and the ventilation circuit (not shown). Flexible tubes connected to a RSR device can facilitate the setup of the ventilator circuit, as well as facilitate repositioning a RSR device.

Figure 21:
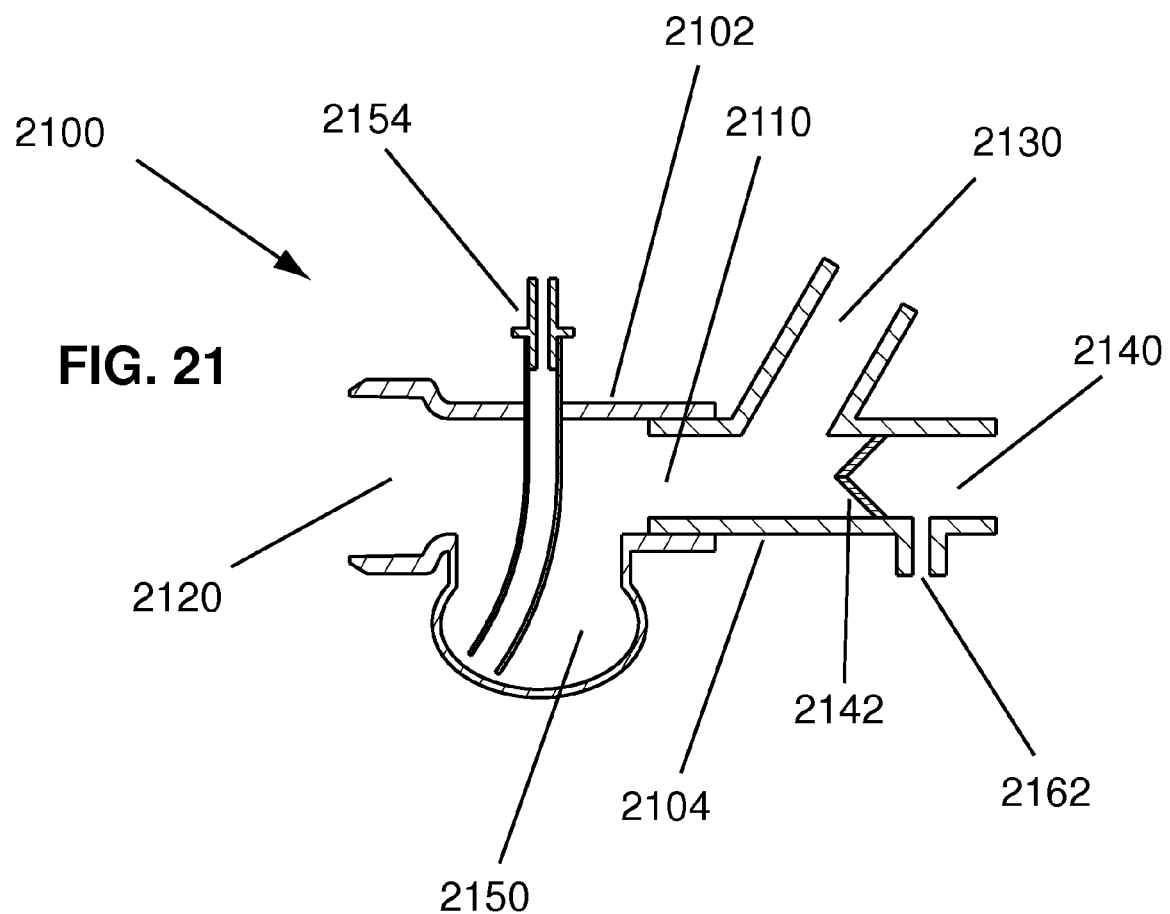
FIG. 21 shows a cross-sectional schematic illustration of variations of the RSR device shown according to a certain embodiment of the present invention.

Each of the RSR device embodiments described in this specification can have a housing portion with a fitting portion. FIG. 21 illustrates a RSR device 2100 that is similar to RSR device 1800. RSR device 2100 includes a housing portion 2102 and a fitting portion 2104. Housing 2102 can include a patient port 2120 and a connection port 2110. The housing 2102 is designed to retain secretions as described in previous embodiments. In embodiments, the patient port 2120 and the connection port 2110 can have swivel connectors. Connected to the connection port 2110 is a fitting portion 2104 of RSR device 2100. The fitting portion 2104 can include an instrument port 2140 for receiving a medical instrument. The fitting portion 2104 also can include a ventilation port 2130. Ventilation port 2130 can be affixed to the fitting portion 2104 at an angle, for example 30 or 90 degrees, or can be parallel to any other port. One or more of ports 2110, 2130, 2140 on the fitting portion 2104 can have swivel connectors as discussed in previous RSR device embodiments. Similar to RSR device 1800, RSR device 2100 may include a valve 2142 located within the instrument port and can include a fluid instillation port 2162. In embodiments, fitting portion 2104 could be a separate part. In embodiments, a tube may be positioned between or instead of the fitting portion 2104 of RSR device 2100. Additional features such as a diverter (not shown), which are described in other embodiments of this invention, also can be located in the RSR device 2100 to further separate secretions from the gas flow. FIG. 21 also illustrates a suction tube assembly 2154 that serves as a drain port for RSR device 2100. Suction tube assembly 2154 can be connected to a suction device to clear the RSR device of any contained respiratory secretions. Suction tube assembly 2154 may be capped or plugged externally (not shown) when suction is not required. Suction tube assembly 2154, which is mounted to housing 2102, may be repositioned by translation, rotation, or both to facilitate removal of secretions from reservoir 2150. Suction tube assembly 2154 may have an angled tip portion to allow it to access different areas of RSR device 2100 when suction tube assembly 2154 is repositioned. Any embodiment of this invention can have a drain port similar to the suction tube assembly 2154.

FIG. 22A illustrates another embodiment of an RSR device. RSR device 2200 can include a housing 2202, which can include a patient port 2220, a ventilation port 2230 and an instrument port 2240. Any of the ports 2220, 2230, or 2240 could have swivel connectors as discussed in previous RSR device embodiments. In embodiments, housing 2202 can include a side cavity 2252 configured to assist in the removal of liquid contents of reservoir 2250. In FIG. 22A, the instrument port 2240 is shown in a coaxial alignment with the patient port 2220; however, the two ports can be in a non-coaxial alignment as well. In this embodiment, the patient port 2220 and the ventilation port 2230 are provided with pivoting features, for example ball and socket joints, which allow for the rotation of the housing 2202 without exerting undue stress on any attached artificial airway tubing or ventilation tubing connected to patient port 2220 and ventilation port 2230, respectively. For example, as the housing 2202 is rotated downward, the side cavity 2252 translates to a substantially downward orientation, as illustrated in FIG. 22B, and the fluid contents 2256 of reservoir 2250 collect in side cavity 2252. A medical instrument 2210, e.g., a suction catheter, can be inserted through the instrument port 2240 and introduced to into side cavity 2252 to allow the removal of the liquid contents, e.g., secretions from the reservoir 2250. In FIG. 22B, repositioning of the RSR device 2200 is actuated by use of ball and socket joints at the patient and ventilation ports 2220, 2230. In other embodiments, repositioning can be actuated by use of translating fittings, swivels (single axis or multiple axes) and/or other rotational and translational mechanisms located at the patient and ventilation ports 2220, 2230. Even though the housing 2202 is shown repositioned in FIG. 22B, the patient port 2220 and the ventilation port 2230 are still oriented as in FIG. 22A and are still oriented at the same angle with respect to one another. This allows the housing 2202 to be repositioned without affecting the artificial airway or the ventilation circuit. In embodiments, patient port 2220, ventilation port 2230, and/or housing 2202 may have features to maintain a desired position with respect to one another, such as locking features, and/or features to limit range of repositioning.

FIG. 23A illustrates another embodiment of an RSR device. RSR device 2300 can include a housing 2302, which can include a patient port 2320 and an access port 2330 that can function as both a ventilation port and an instrument port. Any of the ports 2320 or 2330 could have swivel connectors as discussed in previous RSR device embodiments. In embodiments, housing 2302 can include a suction tube assembly 2354, which is mounted to the housing 2302 and connected to an actuation mechanism 2370, such as a knob, a dial, a button or the like, that provides for repositioning of the suction tube assembly 2354 within the housing 2302 by rotation, translation or other means of motion. Referring again to FIG. 23A, a medical instrument 2310, e.g., a catheter, passes through a passage 2372 of the suction tube assembly 2354 and through the patient port 2320 into an artificial airway. In a second position, the catheter 2310 can couple with a suction tube portion 2374 of the suction tube assembly 2354 such that suction is directed to the bottom of the reservoir 2350 to drain the fluid contents 2356. In embodiments, suction tube portion 2374 could have a funnel shaped entrance to facilitate entry of the catheter. In embodiments, suction tube portion 2374 could have a valve or membrane that seals around the catheter when it is inserted into the suction tube portion. FIG. 23B illustrates the suction tube assembly 2354 positioned to suction the reservoir 2350. Suction tube assembly 2354 and/or actuation mechanism 2370 may be locked into a certain position(s) if desired.

FIG. 24 illustrates another embodiment of an RSR device. RSR device 2400 can include a housing 2402, which can include a patient port 2420 and an access port 2430 that can function as both a ventilation port and an instrument port. Any of the ports 2420 or 2430 could have swivel connectors as discussed in previous RSR device embodiments. In embodiments, housing 2402 can include a suction tube assembly 2454, which is mounted within the housing 2402. Referring to FIG. 24A, a medical instrument 2410, e.g., a catheter, passes through a passage 2456 (FIG. 24B) and a valve 2442 of the suction tube assembly 2454 and through the patient port 2420 into an artificial airway. In a second position, as illustrated by FIG. 24B, the catheter 2410 can couple with a suction tube fluid removal portion 2458 of the suction tube assembly 2454 such that suction is directed to the bottom of the reservoir 2450 to drain the fluid contents 2456. In this embodiment, the medical instrument 2410 is not extended through the valve 2442, which remains closed, but is seated near the top of the suction tube fluid removal portion 2458 to suction the fluid contents 2456 of reservoir 2450. Suction tube assembly 2454 could have at least one additional valve or membrane 2444 that seals around the catheter when it is inserted into the suction tube assembly. In embodiments, suction tube assembly 2454 could have a funnel shaped entrance to facilitate entry of the catheter. An additional port may be included in the RSR device to remove secretions.

FIG. 25A illustrates another embodiment of an RSR device. RSR device 2500 can include a housing 2502, which can include a patient port 2520 and an access port 2530 that can function as both a ventilation port and an instrument port, and a tube 2560 coaxially aligned and positioned between the patient port 2520 and the access port 2530. Any of the ports 2520 or 2530 could have swivel connectors as discussed in previous RSR device embodiments. Tube 2560 can include a diverter 2514 that is attached to an inner bottom wall at a hinge point 2516 to the tube 2560. In embodiments, diverter 2514 can attach along any portion of the inner wall of tube 2560 at any hinge point or points. The tube 2560 further can include a first opening or aperture 2562 and second opening or aperture 2564 in the top and bottom walls, respectively, of tube 2560. First aperture 2562 and second aperture 2564 can be located near the midpoint of tube 2560 on opposing walls. In embodiments, the apertures could be located at any point and on any wall of tube 2560 as long as the apertures are on different sides of the diverter. As illustrated in FIG. 25A, the flow diverter 2514 is in a first position, where the fluid expirations from the patient port 2520 can strike flow diverter 2514 and exit tube 2560 via second aperture 2564 into reservoir 2550 where the liquids are retained while the gases flow around the outside of tube 2560 and reenter tube 2560 via first aperture 2562, and then flow on to access port 2530. FIG. 25B illustrates when a medical instrument 2510, e.g., a catheter, is inserted into access port 2530, to pass through tube 2560, the catheter can force the flow diverter 2514 into an open position allowing the medical instrument to access patient port 2520 and any artificial airway connected to patient port 2520. In embodiments, patient port 2520 and access port 2530 are coaxially aligned. In embodiments, flow diverter 2514 can be pushed into an open position via a manual operation. Manual operation could be accomplished by a button, switch, knob, or other means of mechanical operation. By pushing the flow diverter into an open position or going through the flow diverter, a medical instrument 2510, e.g., a suction catheter can be passed from the access port 2530 into the artificial airway. In embodiments, the flow diverter 2514 can also be configured in such a way so as to allow the medical instrument 2510 to pass through it as discussed in previous embodiments. For example, diverter 2514 could be a valve. In embodiments, the diverter 2514 may redirect the medical instrument into the reservoir 2550, for example to suction the reservoir of retained secretions. Other features and methods for clearing an RSR device of respiratory secretions described in other embodiments of this invention, including drain ports and/or or suction ports may also be located in the RSR device 2500.

FIG. 26A illustrates a cross-sectional perspective view of another embodiment of an RSR device. RSR device 2600 can include a housing 2602, which can include a patient port 2620, a ventilation port 2630, and an instrument port 2640. Any of the ports 2620, 2630, or 2640 could have swivel connectors as discussed in previous RSR device embodiments. In embodiments, housing 2602 can include a suction tube assembly 2654, which is mounted to the housing 2602 and connected to an actuation mechanism 2670, such as a knob, a dial, a button or the like, that provides for repositioning of the suction tube assembly 2654 within the housing 2602 by rotation. FIGS. 26B and 26C illustrate cross-sections through the patient port 2620. Referring to FIG. 26B, a medical instrument 2610, e.g., a catheter passes through a passage 2672 of the suction tube assembly 2654 and through the patient port 2620 into an artificial airway. In a second position as illustrated in FIG. 26C, the catheter 2610 can couple with a suction tube portion 2674 of the suction tube assembly 2654 such that suction is directed to the bottom of the reservoir 2650 to drain the fluid contents 2656. FIG. 26C illustrates the suction tube assembly 2654 rotated relative to its position in FIG. 26B in order to suction the reservoir 2650. Suction tube assembly 2654 and/or actuation mechanism 2670 may be locked into a certain position(s) if desired.

In the position illustrated in FIG. 26B, the suction tube assembly 2654 itself also can function as a diverter to further separate secretions from the gas flow. In all embodiments of this invention that have a feature to divert secretions from the gas flow, an actuation mechanism such as actuation mechanism 2670 could be provided to the RSR device to allow for repositioning of the diverter feature. For example, RSR device 1600 has a diverter 1620 that is shown in the gas flow path. An actuation mechanism may be connected to diverter 1620 that allows the diverter to be repositioned to a new position where it is not in the gas flow path. This new position could facilitate the insertion of a medical instrument through the RSR device by allowing the medical instrument to go around diverter 1620 instead of through diverter 1620.

Figure 27A:
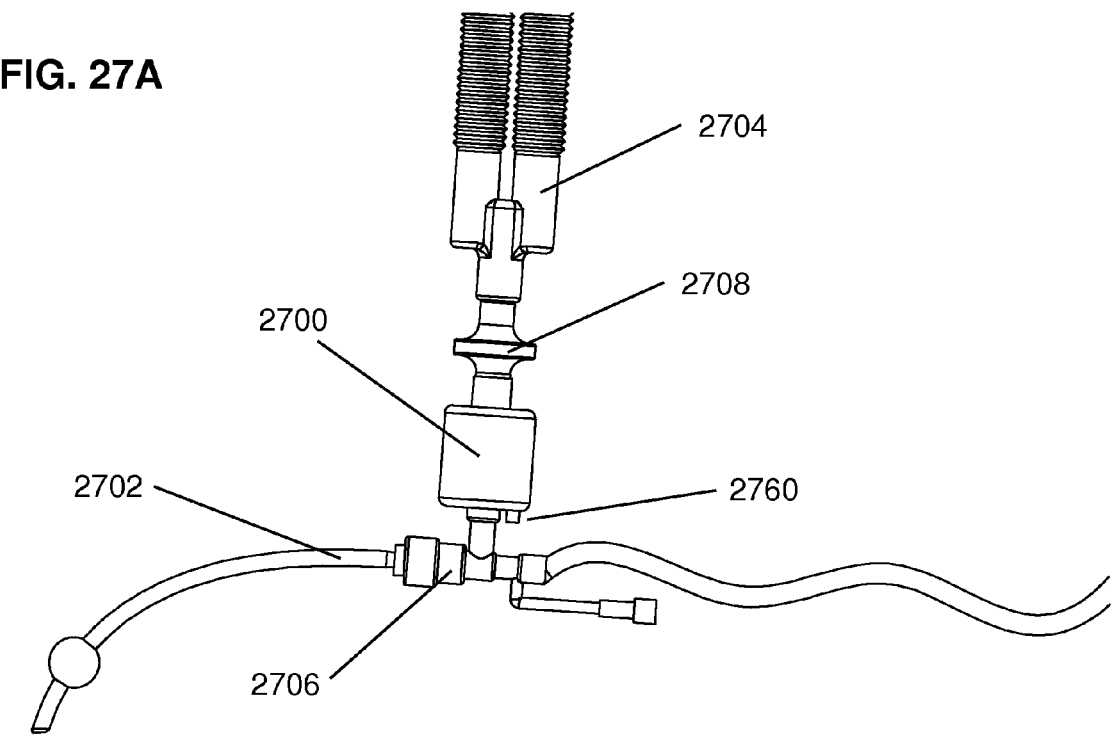
FIG. 27 shows cross-sectional schematic illustrations of variations of the RSR device shown according to a certain embodiment of the present invention.
Figure 27B:
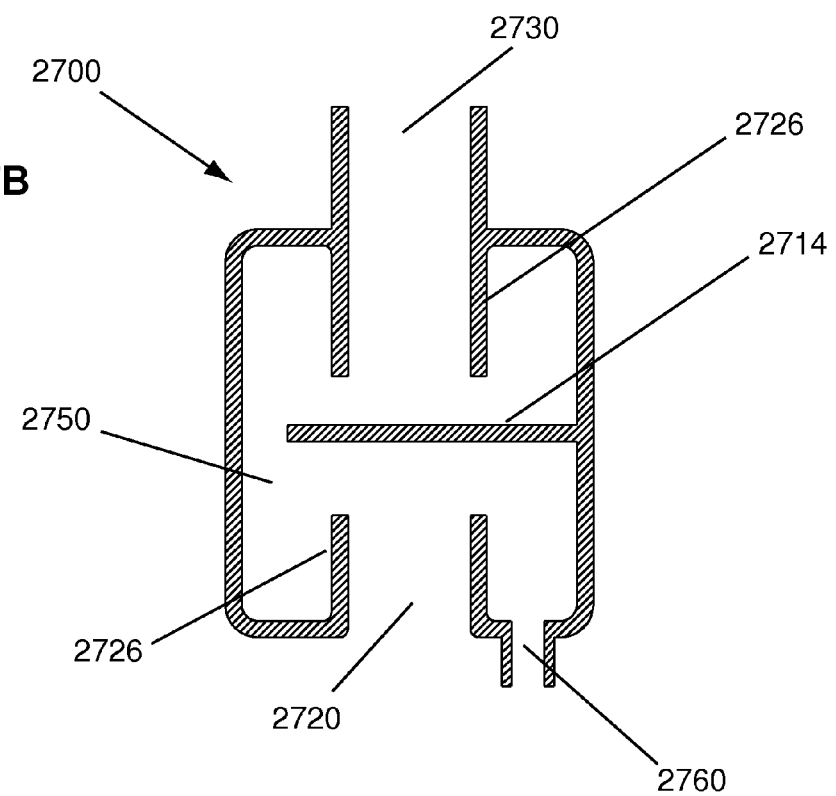

As previously discussed, all of the RSR device embodiments in this invention may be located at any point in the breathing circuit in order to protect either the downstream (towards the patient) or upstream (towards the ventilation source) circuit components from patient secretions or any other liquid in the circuit. For example, a RSR device can be placed between a closed suction system and an HME or ventilator circuit, as illustrated in FIG. 27A. RSR device 2700 is connected between closed suction system 2706 and HME 2708. It is understood that the RSR device can be connected to other components found in breathing circuits, such as tubing, fittings (e.g., wyes, tees, connectors, elbows, adapters and spacers), medication delivery device, etc. Also shown are an artificial airway 2702 and a ventilator circuit 2704. In this embodiment, RSR device 2700 may have a port 2760 located on the housing for the removal of fluids which have been trapped by the device. FIG. 27B, a cross-sectional view of RSR device 2700, illustrates that the RSR device may include a patient side port 2720, a ventilator side port 2730, and a reservoir 2750. The RSR device may also include a diverter 2714, similar to diverters described in other embodiments of this invention. RSR device 2700 may have spill guards 2726 which prevent patient secretions from reentering the circuit once they are trapped. Both ports 2720 and 2730 may include swivel connectors as discussed in previous RSR device embodiments.

As previously discussed, all of the RSR device embodiment of this invention may include drain ports to facilitate removal of respiratory secretions. Drain ports may include a valve for the application of suction. The actuation of the valve could be via insertion of a medical instrument, manual user operation as with a push button valve, by automated electrical operation as with a computer controlled solenoid valve, or any other suitable means of actuation.

FIG. 28 illustrates another embodiment of an RSR device. RSR device 2800 can include a housing 2802, a patient port 2820, a ventilation port 2830, a tube 2832, which can defined patient port 2820 and ventilation port 2830 and one or more drain ports 2860. Any of the ports 2820 or 2830 could have swivel connectors as discussed in previous RSR device embodiments. Housing 2802 can have a reservoir 2850 for collection of fluids. Housing 2802 can contain a tube 2832 that has a plurality of holes 2846. The holes 2846 can take any shape or configuration such that fluid may pass through the holes 2846 and into reservoir 2850. As secretions move through tube 2832, air pressure and/or gravity can force the secretions out through holes 2846 and into reservoir 2850. Housing 2802 can be configured in a conical shape, which can aid in the retention and clearance of secretions from the reservoir 2850. Gravity can aid in the movement of secretions through the reservoir towards a drain port 2860. Secretions can be drained or suctioned through the at least one drain port. In this embodiment, a plurality of drain ports increases the number of positions that RSR device 2800 may be cleared of secretions. As discussed previously, any or all of the drain ports could include a control valve (not shown). In embodiments, holes 2846 are positioned in such a way as to create an area above and below the holes for secretions to accumulate in reservoir 2850 for when RSR device 2900 is positioned with the axis of tube 2832 in a vertical orientation. This prevents unintended emptying of secretions from reservoir 2850 back into tube 2832.

FIG. 29A illustrates a cross-sectional perspective view of an embodiment of an RSR device. RSR device 2900 includes a tube 2932 (best shown in FIG. 29B), which defines a patient port 2920 and a ventilation port 2930. Any of ports 2920 or 2930 can have swivel connectors as discussed in previous RSR device embodiments. RSR device 2900 also includes housing 2902 attached to tube 2932, which defines drain port 2960 and fluid instillation port 2965. Housing 2902 can be comprised of a flexible material such as thin plastic. Sleeve 2942 surrounds tube 2932 and has sleeve slots 2944. Referring to the cross-section illustrated in FIG. 29B, tube 2932 is also shown to have slots, tube slots 2934. Slots 2934 and 2944 can take any shape or configuration such that fluid could pass through the slots and could be considered as holes or the like. RSR device 2900 is configured such that the sleeve 2942 may be rotated angularly with respect to the tube 2932. This rotation can allow sleeve slots 2944 to reposition relative to tube slots 2934 into two distinct configurations. FIG. 29B shows a configuration where sleeve slots 2944 and tube slots 2934 are aligned. FIG. 29C shows a configuration where sleeve slots 2944 and tube slots 2934 are not aligned. Referring to FIG. 29B, in this configuration is the RSR device 2900 can trap liquids such as patient secretions. As secretions travel through tube 2932, air pressure and/or gravity can force the secretions out through both tube slots 2934 and sleeve slots and into reservoir 2950. Referring to FIG. 29C, this configuration is configured to facilitate clearing retained secretions from the reservoir 2950. Sleeve 2942 blocks tube slots 2934 and therefore shields the interior of tube 2932 from the contents of the reservoir 2950. Secretions can be drained or suctioned through the drain port 2960. The instillation of fluid, such as saline, through the fluid instillation port 2965 can facilitate clearing of secretions. When tube slots 2934 are blocked, instilled fluids, liquids, secretions, atmosphere, etc., cannot enter the tube 2932. Housing 2902 may also be repositioned or manipulated, such as by squeezing, to aid in moving secretions through the reservoir and towards drain port 2960. In embodiments, a flexible housing 2902 may aid in clearing secretions when suction is applied as the reservoir 2950 may decrease in size and push the secretions towards drain port 2960. In embodiments, slots 2934 and 2944 are configured in such a way as to limit their length, thereby creating an area above and below the slots 2934 and 2944 for secretions to accumulate for when RSR device 2900 is positioned with the axis of tube 2932 in a vertical orientation. This further prevents unintended emptying of secretions from reservoir 2950 back into tube 2932. In embodiments, sleeve 2942 may be repositioned with respect to tube 2932 by any means such as translation, rotation, etc. In embodiments, sleeve 2942, tube 2932, and/or housing 2902 may have features that maintain a desired position with respect to one another, such as locking features, and/or features to limit the range of repositioning.

Figure 30A:
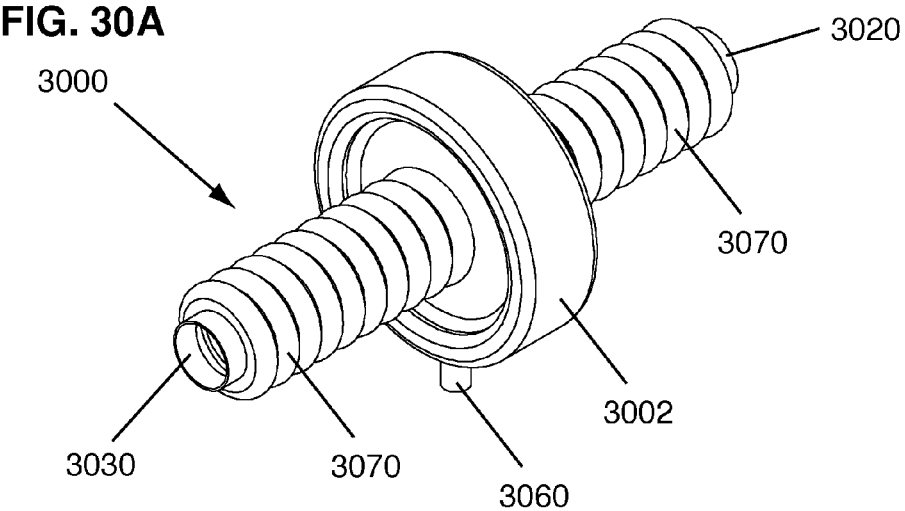
FIG. 30 shows cross-sectional schematic illustrations of variations of the RSR device shown according to a certain embodiment of the present invention.
Figure 30B:
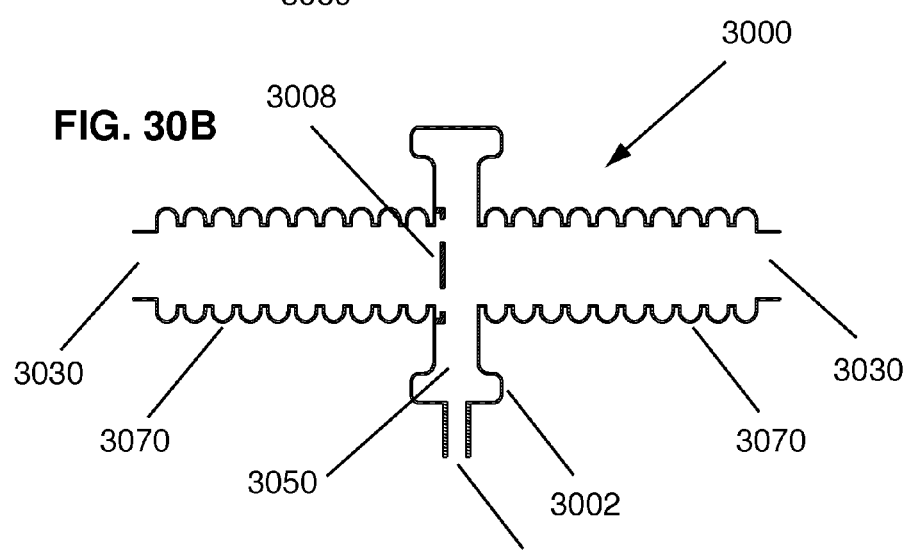
Figure 30C:
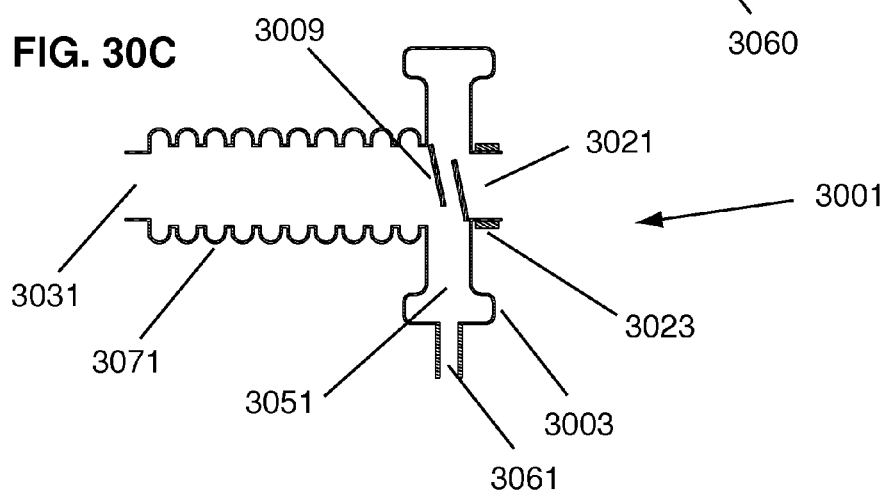

FIGS. 30A and 30B illustrate another embodiment of an RSR device. RSR device 3000 can include a housing 3002, which can include a patient port 3020, a ventilation port 3030, a reservoir 3050 defined by housing 3002, and a drain port 3060. RSR device 3000 can include tube portions 3070, which can be flexible to increase the utility of the device, e.g. by reducing the stresses in the circuit. Ports 3020 and 3030 can have swivel connectors as discussed in previous RSR device embodiments. In this embodiment, swivel connectors are particularly desirable, because the swivel connectors allow the positioning of the drain port 3060 in a downwards orientation thereby facilitating draining of trapped secretions or other fluids. In addition, if flexible tube portions 3070 are present, these flexible tube portions can also assist in positioning the device for draining. Tube portions 3070 may be integral to the housing 3002 or may be attached to housing 3002. If the tube portions 3070 are attached to the housing 3002, it is preferred for the attachment points to have swivel connectors. As discussed previously, drain port 3060 may include an integral valve to facilitate applying suction to the reservoir. As illustrated in the cross-sectional view FIG. 30B, the reservoir 3050 has a dog-bone shape to facilitate the entrapment of secretions. RSR device 3000 also may contain a diverter 3008 as described in previous embodiments. FIG. 30C illustrates another configuration similar to RSR device 3000. RSR device 3001 has a patient port 3021, a ventilation port 3031, a reservoir 3051 defined by housing 3003, and a drain port 3061. RSR device 3001 can include a single tube portion 3071. Ports 3021 and 3031 can have swivel connectors as discussed in previous RSR device embodiments. For example, port 3021 is shown having a swivel connector 3023. Having a single tube portion further reduces the deadspace of the RSR device. RSR device 3001 may have a diverter 3009 as described in previous embodiments. A baffle type of diverter system with more than one diverter, which can be angled, is shown as one example.

Figure 31A:
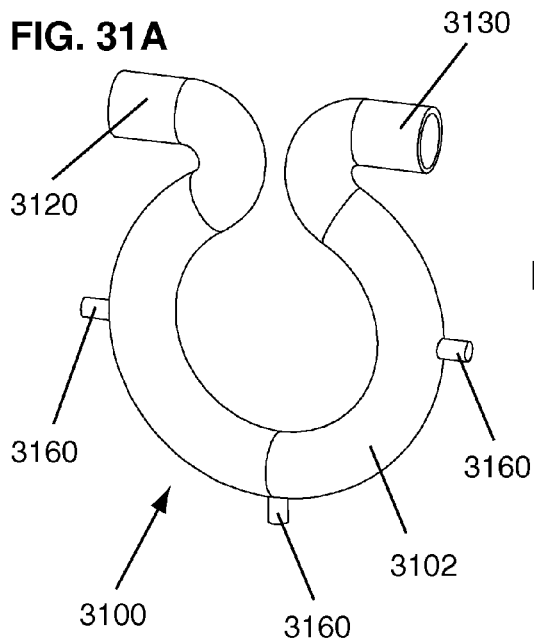
FIG. 31 shows cross-sectional schematic illustrations of variations of the RSR device shown according to a certain embodiment of the present invention.
Figure 31B:
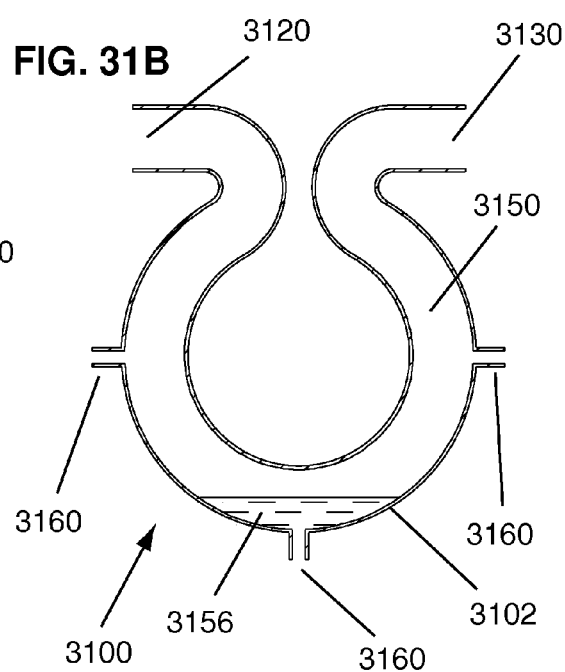
Figure 31C:
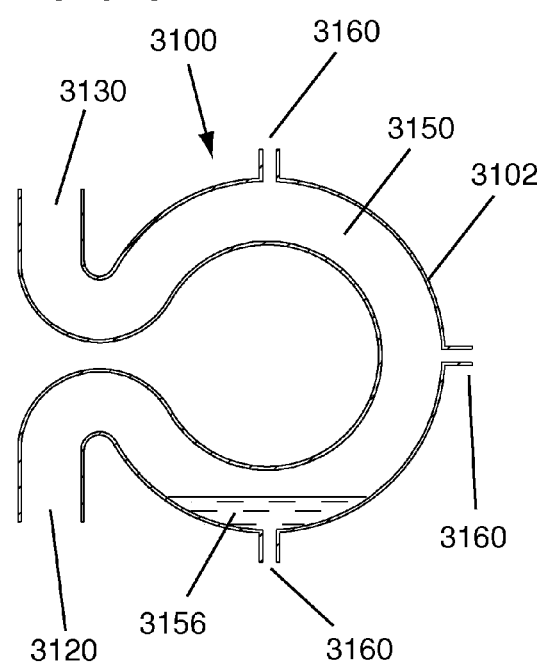
Figure 31D:
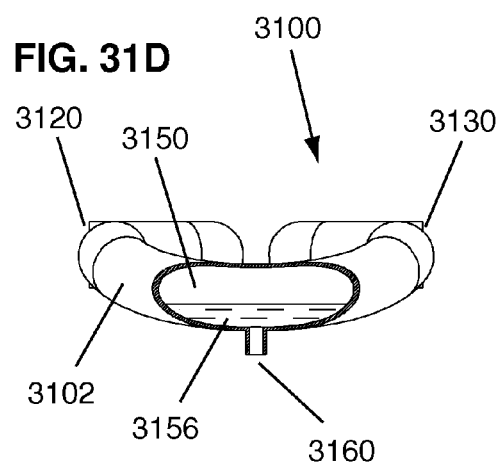

FIG. 31A illustrates another embodiment of an RSR device. RSR device 3100 has a housing 3102. Housing 3102 may be rigid to maintain a "horseshoe" shape whereby secretions can be trapped in several locations. Housing 3102 may also be flexible to allow for some repositioning or adjustability of shape. RSR device 3100 may include a patient port 3120, a ventilation port 3130, and one or more drain ports 3160. Ports 3120 and 3130 can have swivel connectors as discussed in previous RSR device embodiments. In this embodiment, swivel connectors are desirable as they allow positioning of the device to maximize secretion collection. FIG. 31B illustrates secretions 3156 trapped in RSR device 3100 in one orientation. FIG. 31C illustrates secretions trapped in RSR device 3100 in a second orientation. FIG. 31D illustrates secretions 3156 trapped in RSR device 3100 in a third orientation. As shown in FIG. 31D, RSR device 3100 can have a curved housing to further increase the retention of respiratory secretions within the RSR device.

Figure 32A:
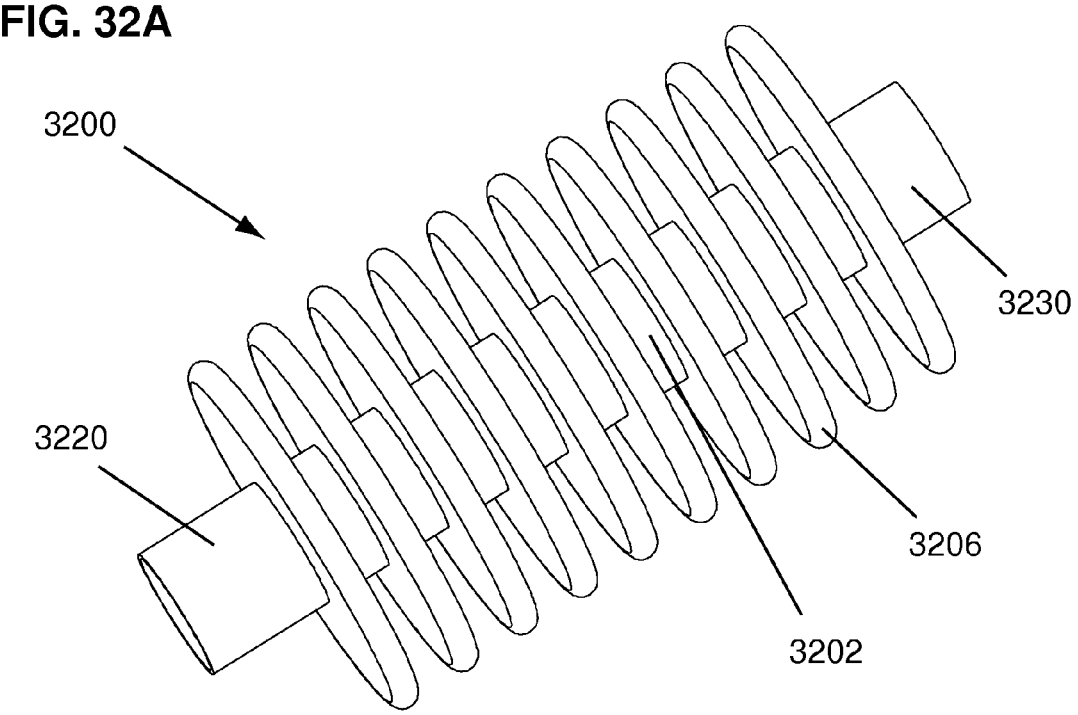
FIG. 32 shows cross-sectional schematic illustrations of variations of the RSR device shown according to a certain embodiment of the present invention.
Figure 32B:
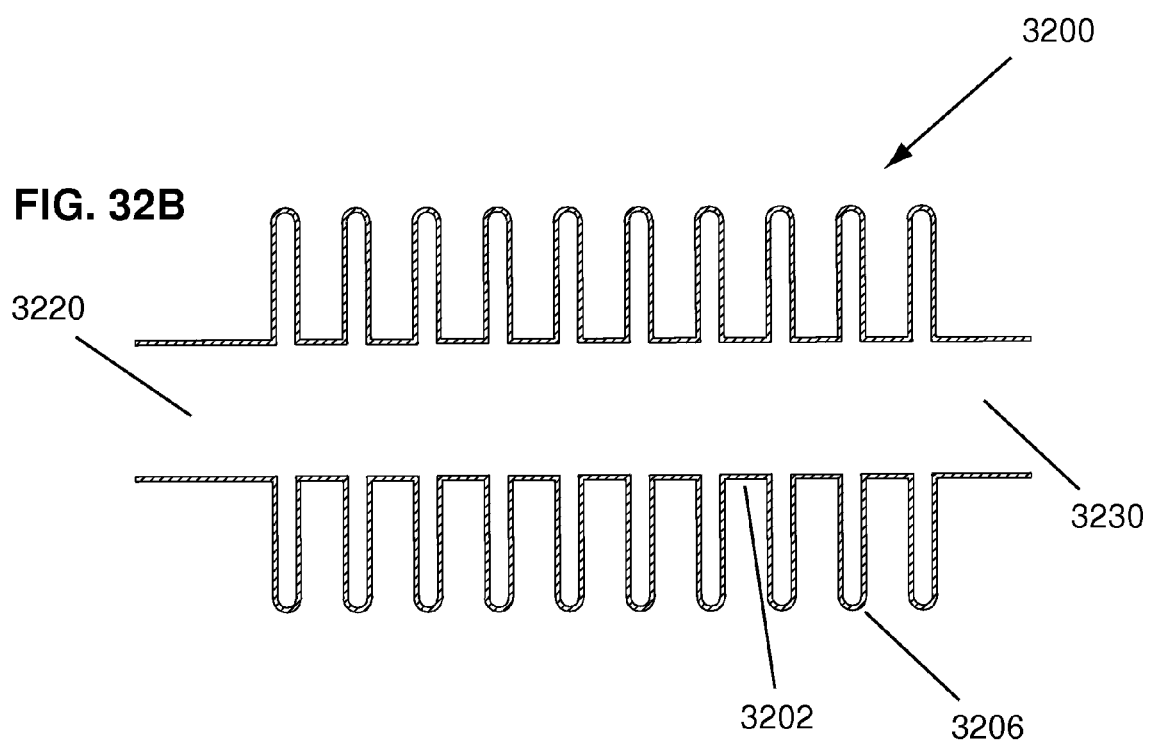

FIG. 32A illustrates another embodiment of an RSR device. RSR device 3200 can include a housing 3202 which defines a tube portion and a plurality of grooves 3206. The RSR device also includes a patient port 3220 and a ventilation port 3230, and one or more drain ports (not shown). Ports 3220 and 3230 can have swivel connectors as discussed in previous RSR device embodiments. As patient secretions advance within housing 3202, the secretions become trapped in the grooves 3206. Grooves 3206 can have a depth of 1 mm or greater to become effective fluid traps. It is also preferred to have at least two grooves if the grooves are individual features, such as circumferential grooves. In embodiments, the grooves may be formed by one helical feature. The configuration of the grooves also limits the resistance to flow in the main tube portion of housing 3202. RSR device 3200 may be flexible and/or may be comprised of a flexible material, such as polyethylene, silicone and the like. The flexibility of the RSR device can add to the utility of the device by relieving stresses in the circuit. In addition, the RSR device 3200 may also be comprised of rigid material such as polycarbonate or polypropylene. In embodiments, RSR device 3200 may have a curved housing to further increase the retention of respiratory secretions within the RSR device. FIG. 32B illustrates a cross-sectional view of RSR device 3200. The passive collection of secretions may function in any orientation and may be aided by flexibility in the RSR device 3200. In embodiments, RSR device 3200 can have no drain port and simply can be disposed of after becoming saturated with secretions.

In addition, although not required for function of this invention, the use of clear materials is desirable as it aids in determining the amount of fluid sequestered in the RSR device. In addition, the RSR device can be made of or coated with antimicrobial substances or materials to prevent the growth of bacteria, and other microbes, for example antimicrobial substances that prevent the formation of biofilms on or within the RSR device. Further coatings containing silver or a silver alloy may be used to prevent or decrease the formation of biofilms and/or inhibit the growth of bacteria on or within the RSR device. Further coatings or materials with hydrophilic properties may be used to improve the retention of secretions in a reservoir area. Further coatings or materials with hydrophobic properties may be used to decrease adhesion of secretions to the diverter or other surfaces in the RSR device. A hydrophobic diverter is more likely to shed tenacious secretions off the diverter and into the reservoir during high flow ventilation.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims, which are to be accorded with the broadest interpretation so as to encompass all such modifications and similar structures.

We claim:

1. A respiratory secretion retention device adapted to fluidly connect to an artificial airway, the device comprising:
    a housing, the housing defining a passageway for the flow of respiratory gases;
    a chamber defined by the housing, a portion of the chamber configured to retain exhaled respiratory particulate and liquid;
    a patient side port coupled with the housing, the patient side port in fluid communication with an artificial airway; and,
    at least one access port coupled with the housing, wherein the at least one access port includes a repositionable valve.

2. The device of claim 1, wherein the at least one access port includes an instillation port.

3. The device of claim 1, further comprising a ventilation port coupled with the housing.

4. The device of claim 3, wherein the ventilation port extends from the housing at an angle with respect to the patient side port.

5. The device of claim 3, further comprising a repositioning element coupled to one of the patient side port and the ventilation port.

6. The device of claim 1 wherein the at least one access port is mounted on a repositionable housing section, the repositionable housing section coupled with the housing and capable of being repositioned from a first position to a second position to facilitate fluid content removal from the chamber.

7. The device of claim 1, wherein the at least one access port and the control valve are located on a fitting portion.

8. The device of claim 7, wherein the fitting portion includes an instillation port.

9. The device of claim 7, wherein the fitting portion includes a ventilation port.

10. The device of claim 1, wherein at least one portion of an interior surface of the device includes one property selected from the group consisting of a hydrophilic property, a hydrophobic property and an antimicrobial property.

11. The device of claim 1, wherein the device includes one component selected from the group consisting of an artificial airway, a closed suction device, a heat and moisture exchange device, a fitting, tubing, a medication delivery device, and a respiratory gas device.

12. The device of claim 1, further comprising a side cavity defined by the housing for receiving fluid contents.

13. The device of claim 1, further comprising a repositioning element coupled to one of the patient side port and the at least one access port.

14. The device of claim 1, further comprising at least one flow diverter positioned in the flow passageway within the housing.

15. The device of claim 1, wherein the at least one access port is adapted to receive one of a medical device and a fitting while maintaining the respiratory secretion retention device closed to atmosphere.

16. The device of claim 1, wherein the at least one access port is adapted to receive a medical device for advancement into the housing while maintaining the respiratory secretion retention device closed to atmosphere.

17. The device of claim 1, further comprising a suction tube subassembly coupled to the housing.

18. The device of claim 1, wherein the at least one access port is a ventilation port.

19. The device of claim 1, wherein at least a portion of the housing is configured to provide for repositioning of the housing to allow removal of retained secretions from within the device.

20. A respiratory secretion retention device configured for fluidly connecting to an artificial airway, the device comprising:
    a housing, the housing defining a passageway for the flow of respiratory gases;
    a chamber defined by the housing, a portion of the chamber configured to retain exhaled respiratory particulate and liquid;
    a side cavity defined by the housing for receiving fluid contents;
    a patient side port coupled with the housing, the patient side port in fluid communication with an artificial airway;
    at least one access port coupled with the housing; and,
    a suction tube subassembly coupled to the housing.

21. The device in claim 20, wherein the suction tube subassembly is coupled to an actuation mechanism that provides for repositioning of the suction tube subassembly with respect to the housing.

22. The device in claim 20, wherein the suction tube subassembly is adapted to provide repositioning of the suction tube subassembly with respect to the housing.

23. The device in claim 20 further comprising at least one valve.

24. The device of claim 20, wherein the suction tube assembly defines a medical instrument passage and a suction tube portion.

25. The device of claim 20, further comprising a repositioning element coupled to one of a patient side port and an at least one access port.

26. The device of claim 20, further comprising at least one flow diverter positioned in the flow passageway within the housing.

27. The device of claim 20, wherein the at least one access port is a ventilation port.

28. The device of claim 20, wherein at least one portion of an interior surface of the device includes one property selected from the group consisting of a hydrophilic property, a hydrophobic property and an antimicrobial property.

29. The device of claim 20, wherein the device includes one component selected from the group consisting of an artificial airway, a closed suction device, a heat and moisture exchange device, a fitting, tubing, a medication delivery device, and a respiratory gas device.

30. A respiratory secretion retention device configured for fluidly connecting to an artificial airway, the device comprising:
    a housing, the housing defining a passageway for the flow of respiratory gases;

a chamber defined by the housing, a portion of the chamber configured to retain exhaled respiratory particulate and liquid;

a patient side port coupled with the housing, the patient side port in fluid communication with an artificial airway;

a ventilation side port coupled with the housing, the ventilation side port in fluid communication with an artificial airway; and, a tube portion, the tube portion defining a passage between the ventilation side port and the patient side port.

31. The device of claim 30, further comprising at least one flow diverter positioned in the flow passageway.

32. The device of claim 31, wherein the at least one flow diverter is repositionable.

33. The device of claim 31, wherein the at least one flow diverter includes an aperture, the aperture defining an instrument passage.

34. The device of claim 30, wherein the housing includes an instillation port.

35. The device of claim 30, further comprising a repositioning element coupled to one of the patient side port and the ventilation side port.

36. The device of claim 30, wherein the ventilation side port is adapted to receive a medical device for advancement into the housing.

37. The device of claim 30, wherein at least a portion of the housing is adapted for repositioning of the housing to allow for removal of retained secretions from within the device.

38. The device of claim 30, wherein at least a portion of the tube portion is adapted to provide for repositioning of the tube portion to allow for removal of the retained secretions from within the device.

39. The device of claim 30, wherein at least one portion of an interior surface of the device includes one property selected from the group consisting of a hydrophilic property, a hydrophobic property and an antimicrobial property.

40. The device of claim 30, wherein the device includes one component selected from the group consisting of an artificial airway, a closed suction device, a heat and moisture exchange device, a fitting, tubing, a medication delivery device, and a respiratory gas device.

41. The device of claim 30, wherein at least a portion of the device is shaped to assist in the removal of the retained secretions from within the device.

42. The device of claim 30, wherein at least a portion of the device is flexible to assist in the removal of retained secretions from within the device.

43. A respiratory secretion retention device configured for fluidly connecting to an artificial airway, the device comprising:

a housing, the housing defining a passageway for the flow of respiratory gases;

a chamber defined by the housing, a portion of the chamber configured to retain exhaled respiratory particulate and liquid;

a patient side port coupled with the housing, the patient side port in fluid communication with an artificial airway;

a ventilation side port coupled with the housing; wherein the ventilation side port is adapted to receive a medical device for advancement into the housing and, a tube portion, the tube portion defining a passage between the ventilation side port and the patient side port.

* * * * *